(12) United States Patent
Ergün et al.

(10) Patent No.: US 11,154,730 B2
(45) Date of Patent: Oct. 26, 2021

(54) MEDICAL DEVICE WITH CMUT ARRAY AND SOLID STATE COOLING, AND ASSOCIATED METHODS AND SYSTEMS

(71) Applicant: Ultra HOM LLC, Stamford, CT (US)

(72) Inventors: Arif Sanli Ergün, Ankara (TR); Andre Khoury, Purchase, NY (US); Butrus T. Khuri-Yakub, Palo Alto, CA (US); John N. Irwin, III, Greenwich, CT (US)

(73) Assignee: Ultra HOM, LLC, Stamford, CT (US)

( * ) Notice: Subject to any disclaimer, the term of this patent is extended or adjusted under 35 U.S.C. 154(b) by 76 days.

(21) Appl. No.: 16/130,896

(22) Filed: Sep. 13, 2018

(65) Prior Publication Data

US 2019/0076674 A1    Mar. 14, 2019

Related U.S. Application Data

(60) Provisional application No. 62/558,200, filed on Sep. 13, 2017, provisional application No. 62/654,765, (Continued)

(51) Int. Cl.
*A61N 7/02* (2006.01)
*A61B 18/02* (2006.01)
(Continued)

(52) U.S. Cl.
CPC .............. *A61N 7/022* (2013.01); *A61B 8/12* (2013.01); *A61B 8/488* (2013.01);
(Continued)

(58) Field of Classification Search
CPC .......... A61B 17/22004; A61B 17/2202; A61B 18/02; A61B 2018/00047;
(Continued)

(56) References Cited

U.S. PATENT DOCUMENTS 7,314,447 B2   1/2008  Park et al.
9,707,414 B2   7/2017  Kardosh et al.
(Continued)

FOREIGN PATENT DOCUMENTS

EP    0643982 A1   3/1995
EP    2403603      1/2012
(Continued)

OTHER PUBLICATIONS

International Patent Application No. PCT/US18/50943; International Search Report and Written Opinion dated Nov. 16, 2016; 16 pgs.
(Continued)

*Primary Examiner* — Baisakhi Roy
(74) *Attorney, Agent, or Firm* — Onello & Mello LLP

(57) ABSTRACT

A medical device includes a capacitive micromachined ultrasonic transducer (CMUT) array configured to emit ultrasound to target tissue, and at least one thermoelectric cooler mechanically coupled with the CMUT array and configured to cool non-target tissue heated by the ultrasound. The medical device may be implemented in a catheter together with a solid thermal conductor coupled to the thermoelectric cooler and extending along the catheter, to conduct heat away from the thermoelectric cooler. A catheter or catheter sleeve includes a tubular wall for insertion into a body channel, and at least one thermoelectric cooler coupled to the tubular wall for cooling the body channel wall. A catheter sleeve includes tubular casing for insertion into a body channel and capable of encasing a catheter, and at least one sensor coupled to the tubular casing for sensing one or more properties of the body channel wall, such as temperature and pressure.

16 Claims, 32 Drawing Sheets

Related U.S. Application Data filed on Apr. 9, 2018, provisional application No. 62/728,616, filed on Sep. 7, 2018.

(51) Int. Cl.
| | | |
|---|---|---|
| *B06B 1/02* | (2006.01) | |
| *A61B 17/22* | (2006.01) | |
| *A61B 8/08* | (2006.01) | |
| *A61B 8/12* | (2006.01) | |
| *A61B 18/00* | (2006.01) | |
| *A61N 7/00* | (2006.01) | |
| *A61B 90/00* | (2016.01) | |

(52) U.S. Cl.
CPC .... *A61B 17/2202* (2013.01); *A61B 17/22004* (2013.01); *A61B 18/02* (2013.01); *B06B 1/0292* (2013.01); *A61B 2018/00047* (2013.01); *A61B 2018/00547* (2013.01); *A61B 2018/00577* (2013.01); *A61B 2018/00791* (2013.01); *A61B 2018/0212* (2013.01); *A61B 2090/064* (2016.02); *A61N 2007/0004* (2013.01); *A61N 2007/0043* (2013.01); *A61N 2007/0078* (2013.01)

(58) Field of Classification Search
CPC . A61B 2018/00547; A61B 8/12; A61B 8/445; A61B 8/546; A61B 8/00; A61B 8/4488; A61N 7/022
See application file for complete search history.

(56) References Cited

U.S. PATENT DOCUMENTS

| | | | | |
|---|---|---|---|---|
| 2004/0002655 | A1* | 1/2004 | Bolorforosh | A61B 8/00 600/459 |
| 2004/0236223 | A1* | 11/2004 | Barnes | A61B 5/0048 600/459 |
| 2005/0075573 | A1* | 4/2005 | Park | A61B 8/00 600/459 |
| 2006/0173344 | A1* | 8/2006 | Marian | A61B 8/00 600/459 |
| 2008/0188755 | A1 | 8/2008 | Hart | |
| 2010/0168583 | A1* | 7/2010 | Dausch | A61B 8/12 600/466 |
| 2011/0077558 | A1* | 3/2011 | Ostrovsky | A61N 7/022 601/2 |
| 2012/0095371 | A1* | 4/2012 | Sverdlik | A61N 7/022 601/2 |
| 2012/0095372 | A1* | 4/2012 | Sverdlik | A61B 17/320068 601/2 |
| 2013/0204167 | A1* | 8/2013 | Sverdlik | A61N 7/022 601/3 |
| 2013/0211292 | A1* | 8/2013 | Sverdlik | A61B 17/2202 601/2 |
| 2013/0296743 | A1 | 11/2013 | Lee et al. | |
| 2014/0005521 | A1* | 1/2014 | Kohler | A61B 5/064 600/411 |
| 2014/0058294 | A1* | 2/2014 | Gross | A61B 8/12 601/2 |
| 2015/0289750 | A1* | 10/2015 | Stigall | A61B 1/00087 600/427 |
| 2019/0060613 | A1* | 2/2019 | Sharman | A61B 5/026 |
| 2019/0307420 | A1* | 10/2019 | Minas | A61B 8/445 |

FOREIGN PATENT DOCUMENTS

| | | |
|---|---|---|
| EP | 2455133 | 5/2012 |
| WO | WO 2013/130655 A1 | 9/2013 |
| WO | WO 2014/141052 A1 | 9/2014 |

OTHER PUBLICATIONS

Rouviere et al. (2011), "Prostate cancer ablation with transrectal high-intensity focused ultrasound: assessment of tissue destruction with contrast-enhanced US", Radiology. May 2011, vol. 259, issue 2, pp. 583-591.

Diederich et al. (1996), "Transurethral Ultrasound Array for Prostate Thermal Therapy: Initial Studies", IEEE Transactions on Ultrasonics, Ferroelectrics, and Frequency Control. vol. 43. No. 6. Nov. 1996.

Chin et al. (2016), "Magnetic Resonance Imaging-Guided Transurethral Ultrasound Ablation of Prostate Tissue in Patients with Localized Prostate Cancer: A Prospective Phase 1 Clinical Trial," European Urology vol. 70, pp. 447-455.

International Patent Application No. PCT/US18/50943; International Preliminary Report on Patentability dated Mar. 26, 2020; 10 pgs.

Chang et al. "Acoustic lens for capacitive micromachined ultrasonic transducers", Journal of Micromechanics and Microengineering, Institute of Physics Publishing, Bristol, GB, vol. 24, No. 8, Jul. 15, 2014.

Extended European Search Report dated May 27, 2021 issued in corresponding European Application No. 18855671.6.

\* cited by examiner

MEDICAL DEVICE WITH CMUT ARRAY AND SOLID STATE COOLING, AND ASSOCIATED METHODS AND SYSTEMS

CROSS-REFERENCE TO RELATED APPLICATIONS

The present application claims the benefit of priority from U.S. Provisional Patent Application Ser. No. 62/558,200 filed on Sep. 13, 2017, U.S. Provisional Patent Application Ser. No. 62/654,765 filed on Apr. 9, 2018, and U.S. Provisional Patent Application Ser. No. 62/728,616 filed on Sep. 7, 2018. All of the aforementioned applications are incorporated herein by reference in their entireties.

BACKGROUND

The normal male urethra passes through the prostate gland. The portion of the urethra located within the prostate is referenced herein as the prostatic urethra.

Benign prostate hyperplasia (BPH), an overgrowth of cells within the prostate often causing enlargement of the prostate, is quite common. According to Wikipedia, 50% of men show BPH histology by age 50 and 75% by age 80; of these as many as half may develop symptoms. The most common symptoms of BPH include interference with urine flow caused by an enlarged prostate applying pressure to the urethra, interference with urine flow leads to incomplete voiding, urine retention, frequent urination, and urinary tract infections which can lead to bladder and kidney damage.

Roughly 80% of men develop prostate cancer by age 80. Although most of these prostate cancers are slow growing, prostate cancer killed approximately 250,000 men worldwide in 2010. Even slow-growing prostate tumors can compromise the urethra by mass effect and tumor invasion and obstruct urine flow, similarly to obstruction in BPH.

BPH and prostate cancer can coexist in a prostate; the combination also can enlarge the prostate sufficiently to interfere with urine flow. High pressure in the prostate, whether from mass effect of a tumor or from BPH, causes the urethra to partially or fully collapse, thus constricting urine flow.

Interference with urine flow caused by prostate glands enlarged by BPH often needs treatment to improve urine flow. This interference has been treated in several ways, including medications that interfere with testosterone, or surgical procedures such as open prostatectomy, transurethral resection of the prostate (TURP), and transurethral laser ablation of the prostate. Transurethral procedures are favored because infection risk, pain, and healing times are typically reduced compared to open surgical procedures.

Transurethral microwave therapy (TUMT), where the prostate is heated using a microwave antenna placed within the prostatic urethra, is among known treatments. TUMT side effects can include urethral damage due to excess heating of the urethra. Laser ablation suffers from similar side effects.

Ultrasonic treatment of the prostate intended to heat portions of the gland sufficient to ablate some of the excess tissue of BPH has been proposed in, for example "Prostate cancer ablation with transrectal high-intensity focused ultrasound: assessment of tissue destruction with contrast-enhanced US", Rouviere et al., Radiology. 2011 May, volume 259, issue 2, pp 583-91, and "Transurethral Ultrasound Array for Prostate Thermal Therapy: Initial Studies", Chris J. Diederich, and Everette C. Burdette, IEEE Transactions on Ultrasonics, Ferroelectrics, and Frequency Control. Vol. 43. No. 6. November 1996 (Diederich). Diederich proposes a catheter having two lumens; coolant water flows into the catheter through one lumen and exits over 7 MHz piezoceramic transducers through a second lumen. Diederich, experimenting in pig muscle, reported significant temperature increases in tissue one and a half centimeters from the transducers; these temperature increases are believed sufficient to kill prostate tissue.

High intensity ultrasound for heating tissue of localized prostate cancer, using piezoceramic transducers is proposed by SonaCare Medical, Alpinion Medical Systems, and Profound Medical (as seen at http://www.profound-medical.com/new-tulsa/). As reported in Magnetic Resonance Imaging—Guided Transurethral Ultrasound Ablation of Prostate Tissue in Patients with Localized Prostate Cancer: A Prospective Phase 1 Clinical Trial, Joseph Chin et al., European Urology vol. 70, pp 447-455 (2016), the Profound Medical device, named MRI-TULSA, relies on external nuclear magnetic resonance imaging (MRI) for precise location of the array for treatment, uses a rigid urethral catheter having ten directional piezoelectric transducers, and employs water cooling by a rectal catheter to avoid destruction of the prostatic urethra. A clinical trial of MRI-TULSA reached internal prostate temperatures of 55 C, sufficient to damage or ablate tissue.

Capacitive micromachined ultrasonic transducers (CMUTs) operate on principles different from those of piezoelectric transducers. Piezoelectric transducers are based on piezoelectric crystals that bend or contract/expand in response to applied electric fields. A CMUT has a cavity formed in a silicon-based substrate. A thin membrane equipped with an electrode is suspended atop of the cavity. Another electrode is positioned below the cavity, fixed on a substrate. Then, when a voltage is applied between the two electrodes, electrostatic attractive forces pull the membrane downwards, shrinking the cavity. When the voltage drop is removed, the membrane rebounds. If the applied voltage is a sinusoid at sufficiently high frequency, the membrane vibrates at the same frequency and sends acoustic energy into the medium with which it is in contact. As opposed to piezoelectric transducers, CMUTs have no significant internal loss mechanism and essentially lack self-heating.

SUMMARY

In an embodiment, a medical device includes a capacitive micromachined ultrasonic transducer (CMUT) array configured to emit ultrasound to target tissue, and at least one thermoelectric cooler mechanically coupled with the CMUT array and configured to cool non-target tissue heated by the ultrasound.

In an embodiment, a catheter for ultrasound treatment with solid state cooling includes (a) a CMUT array configured to emit ultrasound to target tissue, (b) a thermoelectric cooler configured to cool non-target tissue heated by the ultrasound, the ultrasound transducer being disposed at a distal end of the catheter, and (c) a solid thermal conductor coupled to the thermoelectric cooler and extending along the catheter away from the distal end toward a proximal end of the catheter, to conduct heat away from the thermoelectric cooler.

In an embodiment, a system for enhanced ultrasound treatment with solid state cooling includes the catheter, mentioned in the preceding paragraph, and two acoustic mirrors. Each of the two acoustic mirrors is configured to cooperate with the CMUT array to form a respective acoustic cavity, to increase intensity of the ultrasound within the acoustic cavity.

In an embodiment, a medical device includes a catheter for exposing target tissue to ultrasound. The catheter includes (a) a CMUT array disposed at a distal end of the catheter and configured to emit the ultrasound to the target tissue, (b) a thermoelectric cooler configured to cool non-target tissue heated by the ultrasound, and (c) a solid thermal conductor coupled to the thermoelectric cooler and extending along the catheter away from the distal end toward a proximal end of the catheter, to conduct heat away from the thermoelectric cooler. The medical device further includes a catheter handle mechanically coupled to a proximal end of the catheter and configured to be positioned outside a body channel into which the catheter is inserted, to at least partly control the catheter.

In an embodiment, a system for enhanced ultrasound treatment includes a catheter including an ultrasound transducer array and configured to position the ultrasound transducer array in a channel of a body to expose target tissue of the body to ultrasound, and at least one acoustic mirror. Each acoustic mirror is configured for positioning externally to the channel on a side of the target tissue that is opposite the ultrasound transducer array, to form an acoustic cavity that enhances intensity of the ultrasound at the target tissue by creating a standing acoustic wave between the ultrasound transducer array and the acoustic mirror.

In an embodiment, a system for enhanced ultrasound treatment includes a first ultrasound transducer array, and a second ultrasound transducer array cooperatively configured with the first ultrasound transducer array to form an acoustic cavity that enhances intensity of ultrasound, generated by the first ultrasound transducer array and the second ultrasound transducer array, at the target tissue by creating a standing acoustic wave within the acoustic cavity.

In an embodiment, a catheter or catheter sleeve with solid state cooling includes a tubular wall for insertion into a channel of a body, and at least one thermoelectric cooler coupled to the tubular wall for cooling tissue of the channel.

In an embodiment, a catheter sleeve with integrated sensing includes tubular casing for insertion into a channel of a body and capable of encasing a catheter, and at least one sensor coupled to the tubular casing and configured to sense one or more properties of tissue of the channel Each of the one or more properties is selected from the group consisting of temperature and pressure.

In an embodiment, a system for ultrasound treatment with solid state cooling includes ultrasound driving circuitry configured to generate drive signals to drive a CMUT array, so as to expose target tissue to ultrasound. The system further includes Peltier driving circuitry configured to drive at least one thermoelectric cooler, to cool non-target tissue heated by the ultrasound.

In an embodiment, a method for ultrasound treatment with solid state cooling includes (a) exposing target tissue to ultrasound generated by a CMUT array, (b) cooling non-target tissue using one or more thermoelectric coolers to prevent damage to the non-target tissue, and (c) removing heat from the one or more thermoelectric coolers and away from the non-target tissue.

In an embodiment, a method for ultrasound treatment with ultrasound imaging feedback includes (a) obtaining an image of target tissue from an ultrasound transducer array to determine a spatially resolved clutter signal for the target tissue, and (b) based upon the clutter signal and a predetermined correspondence between the clutter signal and treatment efficacy, determining one or more properties of subsequent generation of ultrasound by the ultrasound transducer array to treat the target tissue.

In an embodiment, a product for controlling ultrasound treatment using ultrasound imaging feedback includes machine-readable instructions encoded in non-transitory memory. The machine-readable instructions include (a) a correspondence between an ultrasound clutter signal and efficacy of the ultrasound treatment, and (b) treatment control instructions that, when executed by a processor, evaluate spatially resolved clutter signals obtained from ultrasound imaging of target tissue and utilize the correspondence to determine one or more properties of subsequent ultrasound exposure of the target tissue.

In an embodiment, a method for manufacturing a CMUT array with solid state cooling includes fabricating the CMUT array on a first thermal conductor of a thermoelectric cooler. The thermoelectric cooler includes (a) the first thermal conductor, (b) a second thermal conductor, and (c) disposed between the first thermal conductor and the second thermal conductor, a plurality of n-type semiconductors and a plurality of p-type semiconductors electrically coupled in series such that the series alternates between the n-type semiconductors and the p-type semiconductors.

DETAILED DESCRIPTION OF THE EMBODIMENTS

Figure 1:
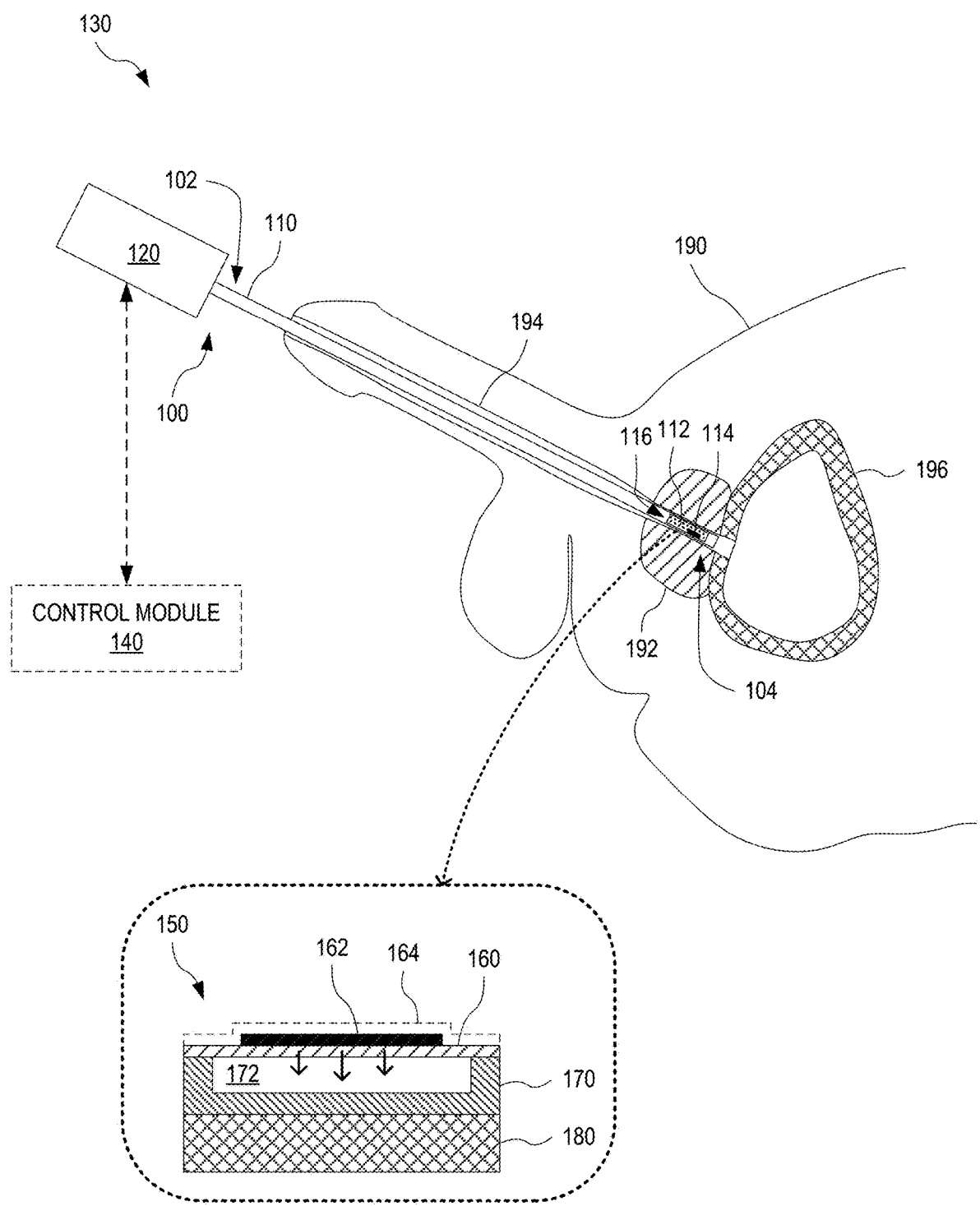
FIG. 1 illustrates a medical device with a capacitive micromachined ultrasonic transducer (CMUT) array and solid state cooling, according to an embodiment.

FIG. 1 illustrates one medical device 100 with a capacitive micromachined ultrasonic transducer (CMUT) array and solid state cooling. Device 100 is configured to treat body tissue from a body cavity, duct, or vessel; herein collectively referred to as a "body channel".

In the embodiment of FIG. 1, medical device 100 includes a catheter 110 configured for insertion into a body channel, such as a urethra 194. Medical device 100 further includes a handle 120 mechanically coupled to a proximal end 102 of catheter 110 and configured to be positioned outside the body channel to at least partly control catheter 110. Catheter 110 includes, at or near a distal end 104 thereof, a CMUT-thermoelectric cooler device 116 having a CMUT array 112 and at least one thermoelectric cooler (TEC) 114 providing solid state cooling). By wielding catheter 110, CMUT-TEC device 116 may be positioned within working distance of target tissue of a subject 190 to be treated by ultrasound.

In operation, CMUT array 112 emits ultrasound to target tissue, such as a prostate 192, for example to induce necrosis of the target tissue, and thermoelectric cooler 114 cools non-target tissue that is heated by the ultrasound, to prevent heat-induced damage to the non-target tissue. The non-target tissue may be heated by direct exposure to the ultrasound and/or by heat propagating to the non-target tissue from the target tissue or other tissue exposed to the ultrasound.

FIG. 1 shows medical device 100 in one exemplary scenario, to expose a prostate, or a portion thereof, to ultrasound from the urethra. In this exemplary scenario, medical device 100 may treat benign prostate hyperplasia (BPH), for example to improve flow of urine from bladder 196; or device 100 may treat prostate cancer. Certain embodiments of medical device 100 may treat a combination of BPH and prostate cancer. Regardless of which of these conditions is being treated, CMUT array 112 may operate to emit ultrasound to tissue of the prostate, while thermoelectric cooler 114 cools at least a portion of the urethral wall to prevent heat-induced damage to the urethra. However, without departing from the scope hereof, medical device 100 may be used in other scenarios to treat other types of body tissue from a different body channel than the urethra.

CMUT array 112 includes an array of CMUT cells 150. In one embodiment, CMUT cells 150 are organized in an array of CMUT elements. Each CMUT element includes a plurality of CMUT cells 150 configured to be driven in unison to cooperatively function as a single larger CMUT cell. FIG. 1 schematically illustrates one exemplary embodiment of a CMUT cell 150. In this embodiment, each CMUT cell 150 includes a substrate 180, an electrically insulating layer 170 having a cavity 172 formed therein, a membrane 160 with an electrode 162 disposed thereon, and, optionally, a protective/electrically insulating layer 164 disposed over electrode 162 and membrane 160. Together, layer 170 and membrane 160 may contain a vacuum in cavity 172; or layer 170 and membrane 160 may contain a gas at less than atmospheric pressure in cavity 172. When a time-varying voltage drop of an appropriate frequency is applied between electrode 162 and substrate 180, functioning as a bottom electrode, the resulting electric field between electrode 162 and substrate 180 will cause membrane 160 to vibrate and generate ultrasound. In certain embodiments, substrate 180 is a silicon substrate, and each of electrically insulating layer 170 and membrane 160 is silicon-based. Alternatively, membrane 160 may be a nanotube-based membrane. Without departing from the scope hereof, CMUT cell 150 may be of a different configuration. For example, CMUT cell 150 may include additional layers, and/or cavity 172 may be formed in a glass substrate with an electrode disposed on the bottom of cavity 172.

CMUT cell 150 generates very little heat, if any at all. In contrast, about 40% of the electrical energy delivered to a typical piezoelectric transducer is lost to friction in the piezoelectric material (as dictated by the imaginary part of the dielectric constant of the piezoelectric transducer), thus generating a substantial amount of heat at the piezoelectric transducer itself. Consequently, when using piezoelectric transducers to heat target tissue a distance away from the piezoelectric transducers (e.g., prostate tissue), the heat generated at the piezoelectric transducers is generally as great as, if not greater than, the heat induced by the ultrasound in the target tissue. Therefore, if the tissue near the piezoelectric transducers is not part of the target tissue, and undesirable damage would result from heating of this tissue, substantial cooling must be applied at the site of the piezoelectric transducers to cool the piezoelectric transducers and/or the adjacent tissue. In the case of a urethral catheter intended for ultrasound treatment of the prostate using piezoelectric transducers, liquid cooling of the piezoelectric transducers and/or the urethral wall near the piezoelectric transducers must accompany the ultrasound treatment to prevent damage to the urethral wall. As a result, such a catheter must be equipped with a cooling fluid circuit carrying cold liquid through the urethral catheter to the site of the piezoelectric transducers, where the cold liquid may absorb some of the heat before being transported back out of the urethra through the catheter. Such a cooling fluid circuit adds complexity and bulkiness to the catheter, and is further associated with safety regulatory requirements relating to introducing a foreign liquid to a patient. Advantageously, the presently disclosed ultrasound transducer 116, by virtue of the negligible heat generation of CMUT cells 150, may operate safely with much lower cooling capacity. Solid state cooling, as provided by thermoelectric cooler 114, is sufficient. Solid state cooling offers a high degree of temperature control. Since the cooling provided by thermoelectric coolers is governed by the Peltier effect, thermoelectric coolers may be turned on and off instantaneously and the degree of cooling is easily adjustable. In contrast, cooling based upon passive heat exchange with a thermal reservoir, e.g., water-cooling or other liquid cooling, is associated with slower on/off transitions due to the thermal mass of the coolant. Thus, the operation of thermoelectric cooler 114 may be easily and rapidly adjusted as needed during ultrasound treatment by CMUT array 112. It is even possible to run thermoelectric cooler 114 in reverse to heat the non-target tissue if necessary, for example to prevent or compensate for over-cooling.

In the embodiment of FIG. 1, medical device 100 is communicatively coupled with a control module 140 in an ultrasound treatment system 130, and handle 120 includes electronic circuitry associated with operation of CMUT array 112 and thermoelectric cooler 114. Control module 140 controls the electronic circuitry of handle 120 to operate CMUT array 112 and thermoelectric cooler 114 according to a treatment procedure. Without departing from the scope hereof, the electronic circuitry of handle 120 may instead be integrated in or with control module 140 externally to handle 120, or control module 140 may be implemented in handle 120 together with the electronic circuitry of handle 120.

In addition to generating ultrasound to treat the target tissue (e.g., prostate 192), CMUT array 112 may perform ultrasound imaging of the target tissue (or other tissue in the field of view of CMUT array 112). In one example, control module 140 utilizes ultrasound images of the target tissue recorded by CMUT array 112 to evaluate the progress of ultrasound treatment of the target tissue and adjust ultrasound exposure of target tissue by CMUT array 112 according to this evaluation. In one treatment protocol example, control module 140 commands CMUT array 112 to alternate between (a) emitting ultrasound at a high energy level to heat the target tissue and (b) imaging the target tissue (and/or other tissue in the field of view of CMUT array 112) by emitting ultrasound at a lower energy level and detecting ultrasound reflected back to CMUT array 112 by the tissue.

Figure 2:
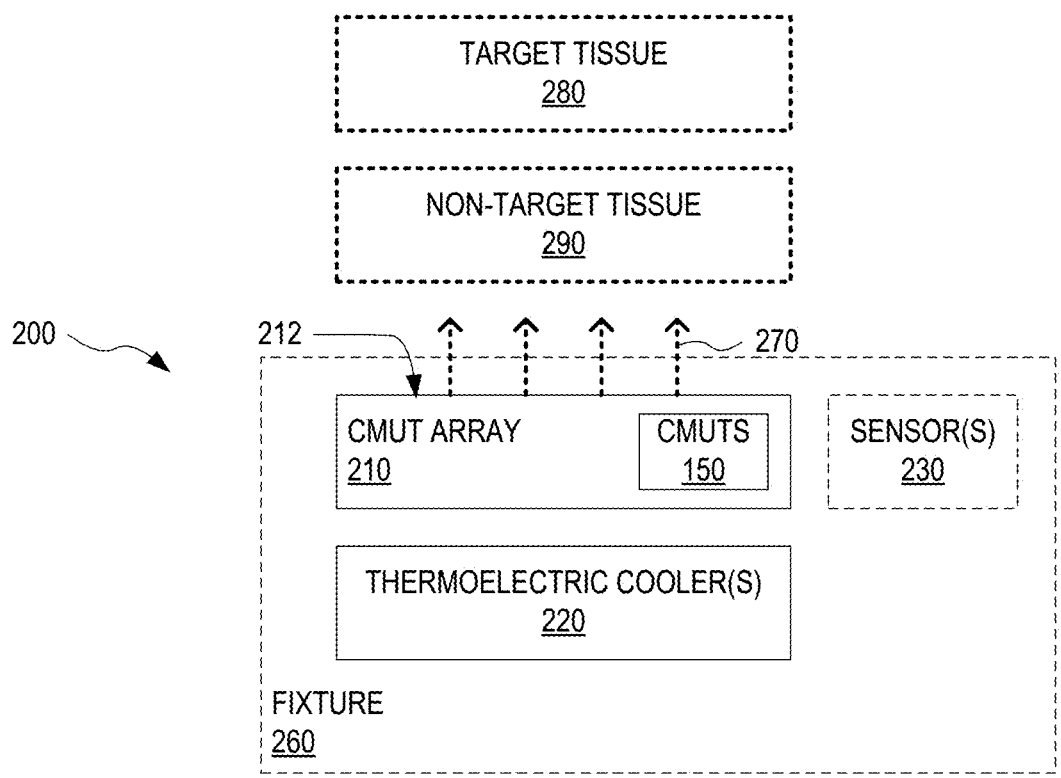
FIG. 2 illustrates a CMUT-thermoelectric cooler (TEC) device having a CMUT array and at least one thermoelectric cooler, according to an embodiment.

FIG. 2 illustrates one CMUT-TEC device 200 having a CMUT array 210 and at least one thermoelectric cooler 220. CMUT-TEC device 200 is, for example, an embodiment of ultrasound transducer 116, FIG. 1. Alternatively, CMUT-TEC device 200 may be deployed in a different catheter. Or, CMUT-TEC device 200 may be configured for operation without a catheter, for example for placement on the skin or a surgically exposed surface of a patient.

CMUT array 210 includes an array of CMUTs 150 configured to emit ultrasound 270 from an ultrasound emission face 212 to target tissue 280. Thermoelectric coolers 220 are configured to cool, by the Peltier effect, non-target tissue 290 heated directly or indirectly by ultrasound 270.

In certain embodiments, CMUT-TEC device 200 includes one or more sensors 230 that sense one or more properties of non-target tissue 290 and/or target tissue 280. Sensor(s) 230 may, for example, sense temperature, pressure, or both. Each sensor 230 is for example a solid state sensor, such as a solid state temperature sensor or a solid state pressure sensor.

Accordingly, sensor(s) 230 may sense one or more properties indicative of the direct or indirect effect of ultrasound 270 on non-target tissue 290. For example, an operator or an automatic controller may at least temporarily cease, reduce, or redirect emission of ultrasound 270 by CMUT array 210 when sensor(s) 230 sense that a property of non-target tissue 290 is outside an acceptable range, such as a temperature that exceeds a threshold temperature or a pressure that exceeds a threshold pressure. In one use scenario associated with ultrasound treatment of prostate 192 from urethra 194, the threshold temperature is in the range between 41 and 45 degrees Celsius (C), such as 42 degrees C., to prevent damage to urethra 194. Heating of target tissue 280, and potentially also non-target tissue 290, may cause swelling of the tissue. An operator or automatic controller may at least temporarily cease, reduce, or redirect emission of ultrasound 270 by CMUT array 210 when sensor(s) 230 sense a pressure that exceeds a threshold pressure, so as to keep the degree of swelling below a certain level. An operator or automatic controller may also adjust the operation of thermoelectric cooler 114 based upon temperature measurements provided by sensor(s) 230.

In other embodiments, sensor(s) 230 sense one or more properties indicative of the progress of treatment of target tissue 280 by ultrasound 270. For example, sensor(s) 230 may sense the temperature of target tissue 280 to facilitate evaluation of the difference between a target temperature and the measured temperature of target tissue 280; sensor(s) 230 may sense the temperature of non-target tissue 290 to facilitate deduction of an at least approximate temperature of target tissue 280 from this measured temperature together with backpropagation to target tissue 280 using a thermal model; and/or sensor(s) 230 may sense the pressure of target tissue 280 and/or non-target tissue 290 to facilitate evaluation of heating of target tissue 280 from the measured pressure together with known characteristics of heat-induced swelling of tissue. In one use scenario, information obtained based upon measurements performed by sensor(s) 230 is combined with information obtained from ultrasound images to determine a property of target tissue 280, such as a necrosis, temperature, and/or volume of target tissue 280. The ultrasound images may be obtained using CMUT array 210.

FIG. 2 shows a fixture 260 that holds CMUT array 210, thermoelectric cooler(s) 220, and, when included, sensor(s) 230. Fixture 260 is, for example, a catheter jacket. Fixture 260 may include a window positioned over CMUT array 210, which at least partly transmits ultrasound 270.

Thermoelectric cooler(s) 220 may be (a) in direct thermal connection with non-target tissue 290, (b) in indirect thermal connection with non-target tissue 290 via fixture 260, or (c) in indirect thermal connection with non-target tissue 290 via CMUT array 210 and, optionally, fixture 260. Preferably, each thermoelectric cooler 220 is positioned outside the propagation region of ultrasound 270 from CMUT array 210 to target tissue 280. Sensors 230 are, for example, positioned on fixture 260 and/or on CMUT array 210.

Although not shown in FIG. 2, it should be understood that CMUT-TEC device 200 may be equipped with electrical connections that connect CMUT array 210 and each thermoelectric cooler 220 (and optionally also each sensor 230) to external electronic circuitry located outside CMUT-TEC device 200. When CMUT-TEC device 200 is implemented in catheter 110, electrical connections between CMUT-TEC device 200 and the external electronic circuitry may run through catheter 110 to handle 120. In one example, the external electronic circuitry drives CMUT array 210 and each thermoelectric cooler 220 (and optionally each sensor 230), and may also receive ultrasound imaging signals from CMUT array 210 and/or sensor signals from sensor(s) 230. Alternatively, a portion of the electronic circuitry is located onboard CMUT-TEC device 200.

Figure 3:
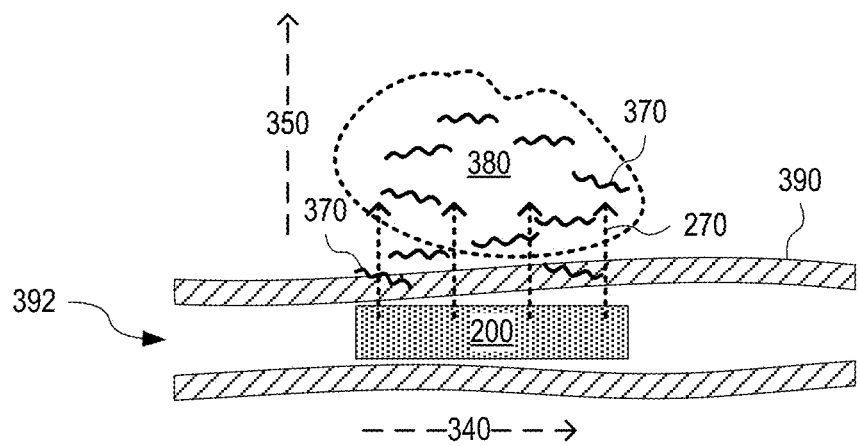
FIG. 3 illustrates the CMUT-TEC device of FIG. 2 in an exemplary use scenario and positioned in a body channel to treat target tissue.

FIG. 3 illustrates CMUT-TEC device 200 in an exemplary use scenario, wherein CMUT-TEC device 200 is positioned in a body channel 392 to treat target tissue 380. Body channel 392 has a wall 390. CMUT array 210 emits ultrasound 270 to target tissue 380. Ultrasound 270 is at least partly converted to heat 370 in target tissue 380. A portion of heat 370 may diffuse to adjacent non-target tissue. In addition, non-target tissue between CMUT-TEC device 200 and target tissue 380, such as wall 390, is directly exposed to ultrasound 270 resulting in direct generation of some amount of heat 370 in this non-target tissue. Thermoelectric cooler(s) 220 cool at least a portion of wall 390 to prevent heat-induced damage to wall 390.

Figure 4:
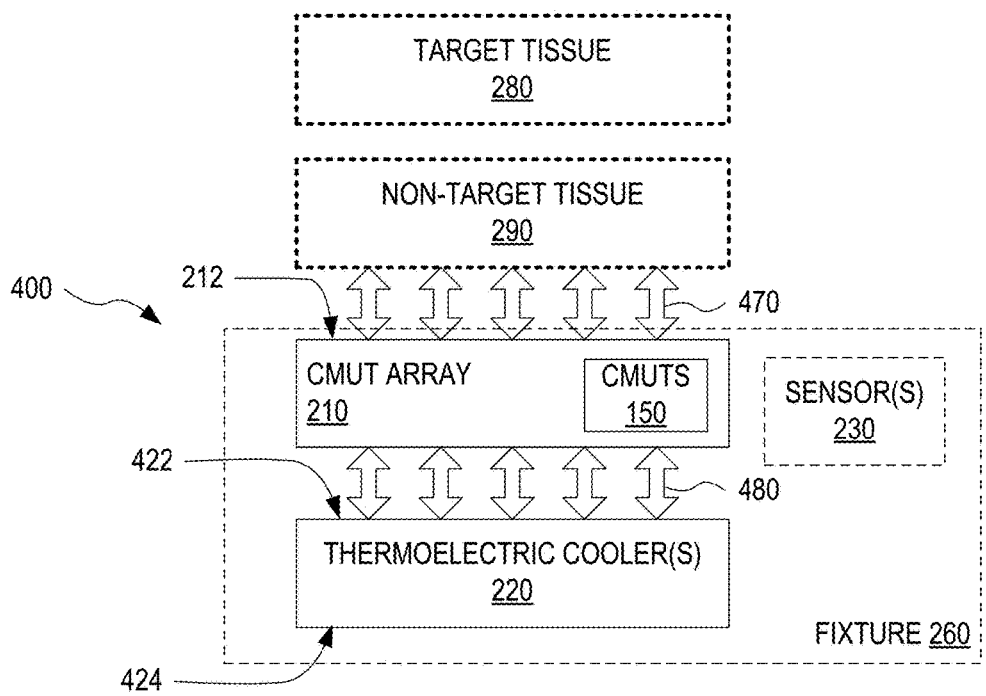
FIG. 4 illustrates a CMUT-TEC device that thermally couples one or more thermoelectric coolers to non-target tissue via a CMUT array, according to an embodiment.

FIG. 4 illustrates one CMUT-TEC device 400 that thermally couples thermoelectric cooler(s) 220 to non-target tissue 290 via CMUT array 210. CMUT-TEC device 400 is an embodiment of CMUT-TEC device 200, FIG. 2. Thermoelectric cooler(s) 220 are in direct or indirect thermal coupling 480 with CMUT array 210 which, when positioned to emit ultrasound 270 to target-tissue 280, has thermal coupling 470 with non-target tissue 290. CMUT array 210 may be in direct thermal coupling 470 with non-target tissue 290, or in indirect thermal coupling 470 with non-target tissue 290 via fixture 260. In one embodiment, ultrasound emission face 212 of CMUT array 210 is in thermal coupling 470 with non-target tissue 290, and thermoelectric cooler(s) 230 are in thermal coupling 480 with a side of CMUT array 210 opposite ultrasound emission face 212. Thus, CMUT array 210 provides a thermal pathway between thermoelectric cooler(s) 230 and non-target tissue 290.

In operation, a voltage drop is applied to thermoelectric cooler(s) 220 to generate a hot side 424 and a cold side 422 through the Peltier effect. The direction of the voltage drop is such that cold side 422 of each thermoelectric cooler 220 is in thermal coupling 480 with CMUT array 210, which is in thermal coupling 470 with non-target tissue 290.

Figure 5:
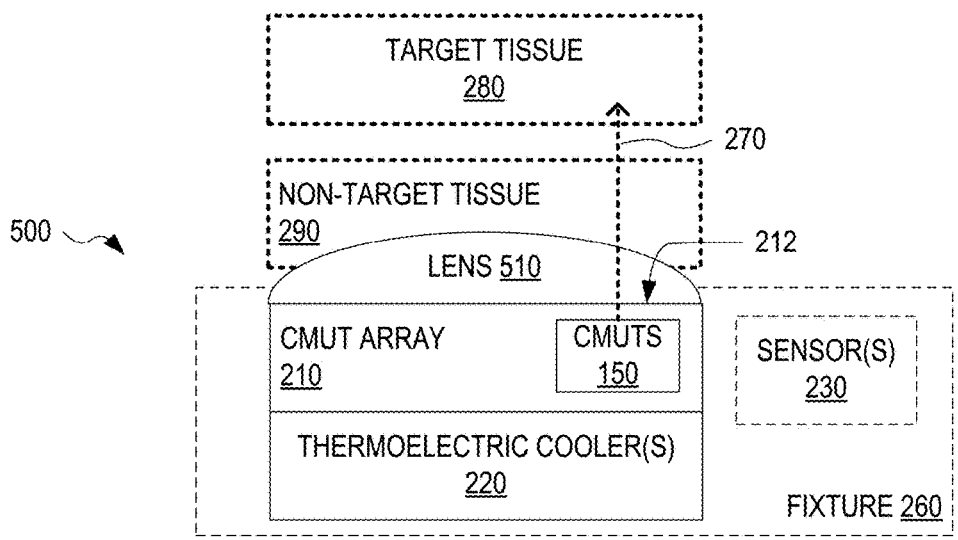
FIG. 5 illustrates another CMUT-TEC device that thermally couples one or more thermoelectric coolers to non-target tissue via a CMUT array, according to an embodiment.

FIG. 5 illustrates another CMUT-TEC device 500 configured to thermally couple thermoelectric cooler(s) 220 to non-target tissue 290 via CMUT array 210, such that thermoelectric cooler(s) 220 may cool non-target tissue 290 via a thermal pathway passing through CMUT array 210. CMUT-TEC device 500 is an embodiment of CMUT-TEC device 400, FIG. 4. CMUT-TEC device 500 includes a lens 510 coupled to ultrasound emission face 212 of CMUT array 210. Lens 510 focuses ultrasound 270, for example on target tissue 280. In one embodiment, CMUT-TEC device 500 is elongated and configured for implemention in a catheter, such as catheter 110, FIG. 1, with the elongated dimension (see elongated dimension 340 in FIG. 3) being aligned with the longitudinal axis of the catheter. In this embodiment, lens 510 focuses ultrasound 270 to a certain distance in the elevation direction (see elevation direction 350 in FIG. 3); that is, lens 510 manipulates emission of ultrasound 270 along the direction perpendicular to the elongated dimension 340 of CMUT-TEC device 500. In operation, lens 510 is in physical contact with non-target tissue 290, optionally via fixture 260, and therefore provides thermal coupling between CMUT array 210 and non-target tissue 290. Lens 510 forms part of the thermal pathway between thermoelectric cooler(s) 220 and non-target tissue 290. In the embodiment shown in FIG. 5, thermoelectric cooler(s) 220 are mounted to, or co-fabricated with, a side of CMUT array 210 that is opposite ultrasound emission face 212. However, without departing from the scope hereof, thermoelectric cooler(s) 220 may be mounted to or co-fabricated with (a) another side of CMUT array 210, (b) fixture 260, or (c) tubing of a catheter in which CMUT-TEC device 500 is implemented.

In an embodiment, thermoelectric cooler(s) 220 are bonded to CMUT array 210 by a thermal adhesive. In another embodiment, thermoelectric cooler(s) 220 are contact bonded to CMUT array 210. In yet another embodiment, fixture 260 holds thermoelectric cooler(s) 220 in physical contact with CMUT array 210. Without departing from the scope hereof, an intermediate substrate (for example containing electrical connections for one or both of CMUT array 210 and thermoelectric cooler(s) 220) may be positioned between CMUT array 210 and thermoelectric cooler(s) 220. In a further embodiment, CMUT array 210 is fabricated directly on thermoelectric cooler(s) 220.

Lens 510 may be substantially composed of silicone rubber, such as polydimethylsiloxane (for example Sylgard, e.g., Sylgard 160) or another silicone rubber having a lower ultrasound attenuation coefficient than polydimethylsiloxane (for example a room-temperature-vulcanizing silicone, e.g., Momentive RTV-615). A lens material characterized by a low ultrasound attenuation coefficient reduces the amount of ultrasound absorbed by lens 510, thus (a) maximizing ultrasound delivery to target tissue 280 and (b) minimizing heating of non-target tissue 290 from ultrasound-induced heating of lens 510. When CMUT-TEC device 500 is configured for implementation in a urethral catheter for ultrasound treatment of prostate 192 from urethra 194, the focal length of lens 510 may be in the range between 10 and 20 millimeters, such as 15 millimeters.

Figure 6:
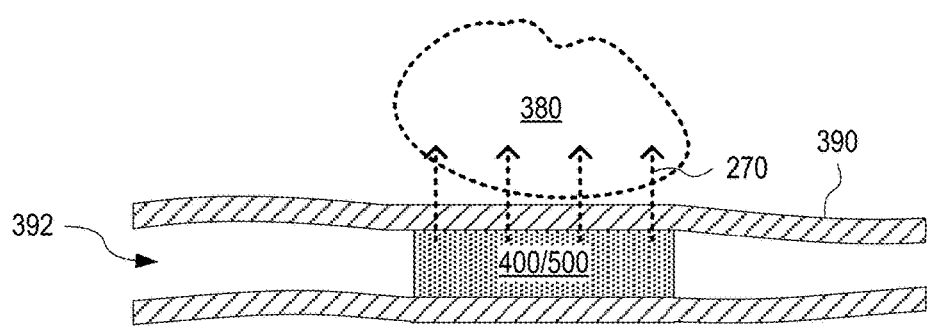
FIG. 6 illustrates an exemplary implementation of the CMUT-TEC devices of FIGS. 4 and 5 in an exemplary use scenario, sized such that the CMUT-TEC device is in physical contact with a wall of the body channel.

FIG. 6 illustrates one implementation of CMUT-TEC device 400 or 500 in an exemplary use scenario, wherein CMUT-TEC device 400/500 is sized such that, when positioned in body channel 392 to treat target tissue 380, CMUT-TEC device 400/500 is in physical contact with wall 390 to ensure physical contact between CMUT-TEC device 400/500 and wall 390. This implementation of CMUT-TEC device 400/500 ensures thermal coupling between thermoelectric cooler(s) 220's cold side 422 and wall 390 via CMUT array 210 and lens 510 (and optionally fixture 260).

Figure 7:
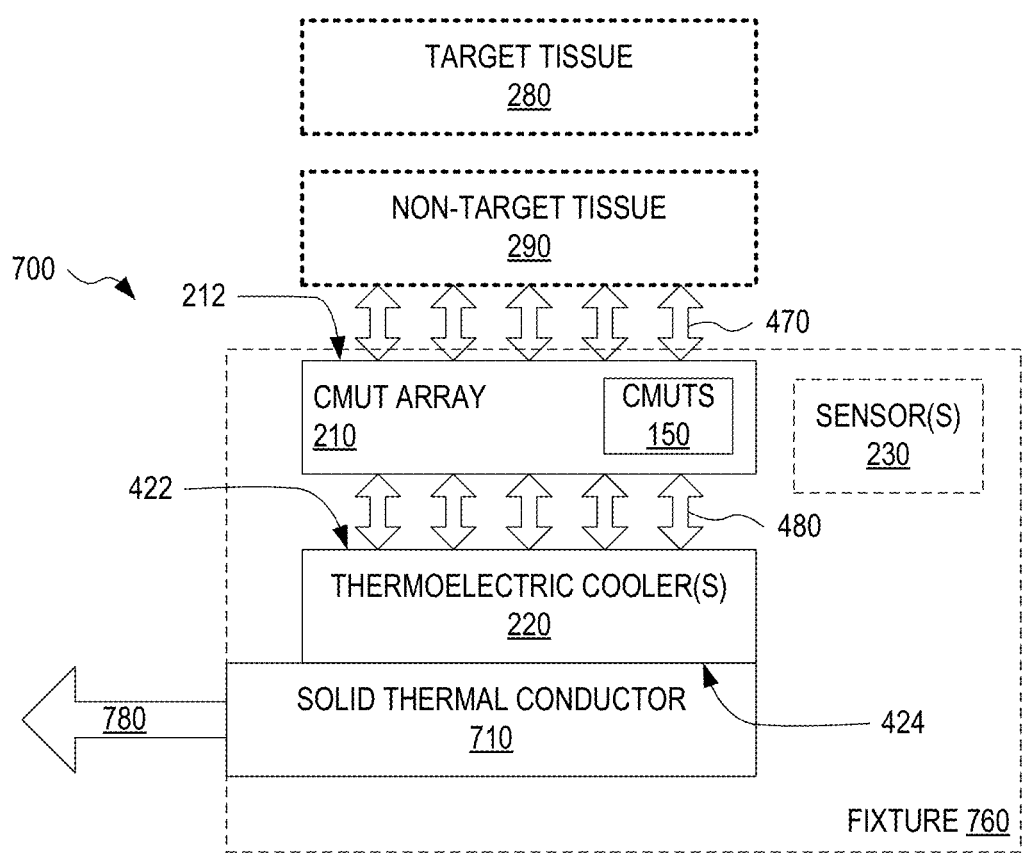
FIG. 7 illustrates a medical device that includes a CMUT-TEC device and a solid thermal conductor to conduct heat away from the CMUT-TEC device, according to an embodiment.

FIG. 7 illustrates one medical device 700 that includes CMUT-TEC device 200 (having CMUT array 210 and thermoelectric coolers 220) and a solid thermal conductor 710 that conducts heat away from CMUT-TEC device 200. Medical device 700 is an embodiment of CMUT-TEC device 400, FIG. 4. Solid thermal conductor 710 is thermally coupled to hot side 424 of each thermoelectric cooler 220. As thermoelectric cooler 220 cools non-target tissue 290, heat is transported to hot side 424, to be conducted away from thermoelectric cooler 220 by solid thermal conductor 710.

In one embodiment, solid thermal conductor 710 includes or is substantially composed of metal, such as copper, silver, and/or aluminum. In one example, solid thermal conductor 710 is a metal rod, such as a copper rod. In another example, solid thermal conductor 710 includes a plurality of braided metal wires, such as a plurality of braided copper wires. The braided metal wires may be configured to allow solid metal conductor 710 to flex, for example if the path available to solid metal conductor 710 is not straight. Such flexibility may advantageously improve patient comfort when solid thermal conductor 710 is positioned along a catheter passing through body channel 392, particularly in situations where solid metal conductor 710 is placed in body channel 392 for an extended period of time or if repositioning/reorientation of the catheter is required. In another embodiment, solid thermal conductor 710 includes or is substantially composed of a non-metallic thermal conductor, for example a thermally conductive nanomaterial such as thermally conductive nanofibers. In yet another embodiment, solid thermal conductor 710 includes or is substantially composed of a thermally conductive nanocomposite. In a further embodiment, solid thermal conductor 710 includes or is substantially composed of a metamaterial.

Solid thermal conductor 710 may extend beyond medical device 700 to conduct heat 780 further away from medical device 700. For example, when implemented in catheter 110, solid thermal conductor 710 may extend at least partway toward proximal end 102 to remove heat 780 from thermoelectric cooler(s) 220 and from non-target tissue 290. Heat 780 is then distributed along a portion of the length of catheter 110, and/or conducted by solid thermal conductor 710 to a heat exchanger (not shown) positioned outside catheter 110, for example in handle 120.

Figure 8:
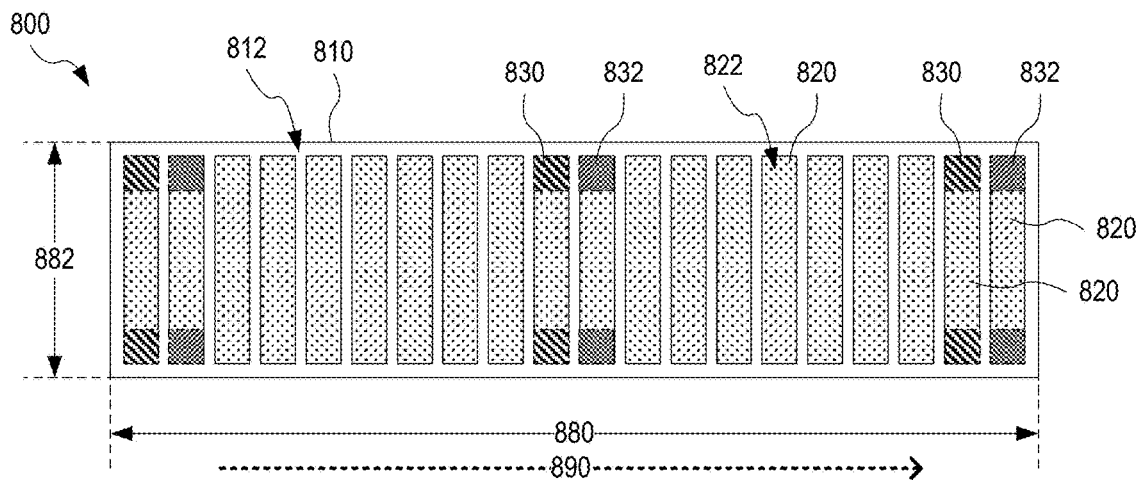
FIG. 8 illustrates a one-dimensional CMUT array, according to an embodiment.

FIG. 8 illustrates one one-dimensional (1D) CMUT array 800. FIG. 8 shows a top plan view of an ultrasound emission face 812 of 1D CMUT array 800. 1D CMUT array 800 is an embodiment of CMUT array 210 and of CMUT array 112. 1D CMUT array 800 includes a substrate 810 (e.g., a silicon substrate) having a 1D array of CMUT elements 820 arranged along an axis 890. For clarity of illustration, not all CMUT elements 820 are labeled in FIG. 8. Axis 890 refers to a direction that, when an associated device is implemented in catheter 110, is substantially parallel to the longitudinal axis of catheter 110. Herein, the longitudinal axis of catheter 110 refers to the general path described by catheter 110 from proximal end 102 to distal end 104. This path may or may not be a straight line, and the direction of the longitudinal axis of catheter 110 may therefore vary along the path between proximal end 102 and distal end 104.

1D CMUT array 800 has extent 880 along axis 890 and extent 882 in the direction perpendicular to axis 890. In one embodiment, extent 880 is greater than extent 882, such that 1D CMUT array 800 is elongated along axis 890. For embodiments of CMUT array 800 intended for insertion into body channel 392 with axis 890 generally oriented along the length of body channel 392 (see, for example, FIG. 3), extent 882 may be limited by the width of body channel 392, whereas extent 880 may be configured based upon a typical extent of target tissue 380 in the direction along the length of body channel 392. In one embodiment adapted for implementation in a urethral catheter, extent 882 is in the range between 2.5 and 3.5 millimeters or in the range between 3.0 and 3.2 millimeters, and extent 880 is in the range between 10 and 50 millimeters. For example, an embodiment with 128 CMUT elements 820 having a center-to-center spacing of 0.2 millimeters, extent 880 is approximately one inch. In another embodiment adapted for implementation in a urethral catheter, extent 882 is 5 millimeters or less.

The number of CMUT elements 820 may be different from that shown in FIG. 8, without departing from the scope hereof. For example, 1D CMUT array 800 may include 128 or 256 CMUT elements 820. Each CMUT element 820 may have the shape of an elongated rectangle, as shown in FIG. 8, or have a different shape such as square, circular, or oval.

Each CMUT element 820 includes one or more CMUT cells 150. In each CMUT cell 150 of CMUT element 820, membrane 160 has electrode 162 on a side 822 of CMUT element 820 facing in the same direction as ultrasound emission face 812. The electrical connection to electrode 162 of each CMUT cell 150 (for clarity not shown in FIG. 8) may be located on ultrasound emission face 812, or be passed through substrate 810 to a side of substrate 810 opposite ultrasound emission face 812. In each CMUT cell 150 of CMUT element 820, substrate 180 (see FIG. 1) may be a layer of substrate 810 that is shared between all CMUT cells 150 of 1D CMUT array 800 and has a single electrical connection. This layer may be interrupted by through-wafer electrical connections to electrodes 162 of CMUT elements 820 from the side of substrate 810 opposite ultrasound emission face 812. When 1D CMUT array 800 is implemented in catheter 110, a flex cable may connect electrical connections of 1D CMUT array 800 to electronic circuitry configured to drive CMUT elements 820. This electronic circuitry is, for example, located in handle 120 or integrated in CMUT-TEC device 116 in the form of an application-specific integrated circuit (ASIC).

1D CMUT array 800 is compatible with beamforming of ultrasound 270, wherein some of CMUT elements 820 receive an electrical drive signal that is phase shifted compared to that received by other CMUT elements 820. In one beamforming scenario, CMUT elements 820 are divided into eight different groups. All CMUT elements 820 belonging to the same group receives the same electrical drive signal, but different groups of CMUT elements 820 may receive different electrical drive signals. Although CMUT elements 820 may be divided into more or fewer groups, it is found that eight different groups provide sufficient spatial resolution of the beamformed ultrasound generated by 1D CMUT array 800.

In one use scenario, some of CMUT elements 820 are dedicated to generate ultrasound 270 to treat target tissue 280, while other CMUT elements 820 perform ultrasound imaging of target tissue 280. In another use scenario, at least some of CMUT elements 820 may, during some periods, generate ultrasound for treatment of target tissue 280 and, during other periods, perform ultrasound imaging of target tissue 280.

In certain embodiments, 1D CMUT array 800 further includes one or more sensors 830/832 disposed on ultrasound emission face 812 or formed in substrate 810 at or near ultrasound emission face 812. For clarity of illustration, not all sensors 830/832 are labeled in FIG. 8. Each sensor 830/832 is an embodiment of sensor 230 and senses a property of tissue near 1D CMUT array 800. In one embodiment, 1D CMUT array 800 includes one or more temperature sensors 830 and/or one or more pressure sensors 832. Sensors 830/832 may, as shown in FIG. 8, be positioned within the portion of ultrasound emission face 812 occupied by CMUT elements 820 or, alternatively, be positioned outside this portion of ultrasound emission face 812. In the embodiment shown in FIG. 2, the presence of sensors 830/832 shrinks the active area of some of CMUT elements 820. Without departing from the scope hereof, all CMUT elements 820 may be identically sized, and sensors 830/832 positioned on ultrasound emission face 812 without spatially restricting the size of some CMUT elements 820 compared to other CMUT elements 820.

1D CMUT array 820 may be implemented in CMUT-TEC device 500 such that lens 510 manipulates the extent of ultrasound 270 emitted by CMUT array 800 in the dimension perpendicular to axis 890. In this implementation, beamforming of ultrasound 270 may be combined with the action of lens 510 to achieve two-dimensional focusing of ultrasound 270.

Figure 9:
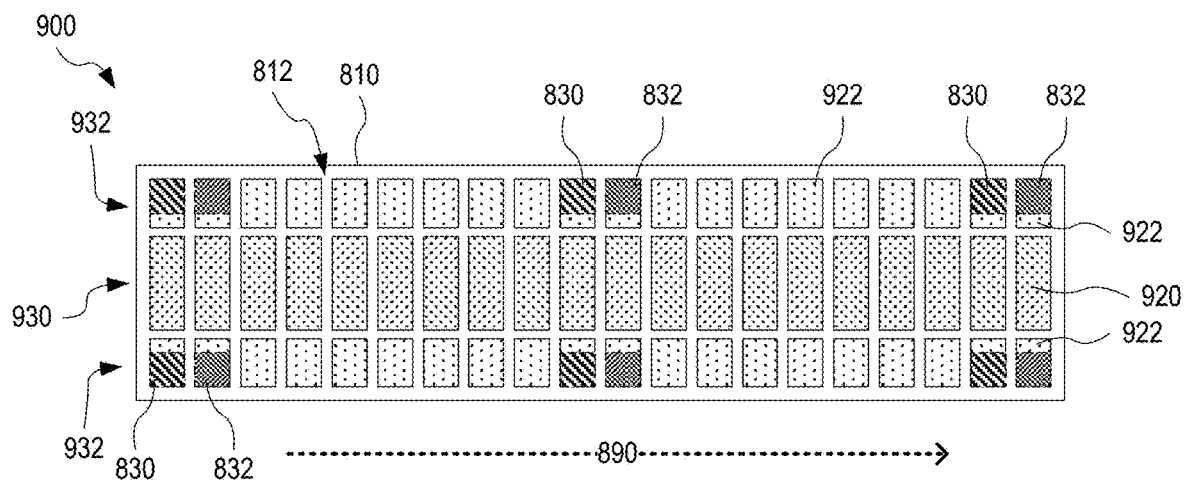
FIG. 9 illustrates a 1.5D CMUT array, according to an embodiment.

FIG. 9 illustrates a 1.5D CMUT array 900. FIG. 9 shows a top plan view of ultrasound emission face 812 of 1.5D CMUT array 900. 1.5D CMUT array 900 is an embodiment of CMUT array 210 and of CMUT array 112. "1.5D" is a term of art in the field of beamforming. A 1.5D transducer array is a two-dimensional transducer array that (a) has high spatial resolution in first dimension and much more limited spatial resolution in an orthogonal second dimension, and (b) is operated in a manner that is symmetrical about a line parallel to the first dimension and centered in the second dimension. For example, a 1.5D transducer array may have three rows, with 128 or 256 transducers in each row, to form an array with 3×128 or 3×256 transducers.

1.5D CMUT array 900 is similar to 1D CMUT array 800 except for the one-dimensional array of CMUT elements 820 being replaced by three rows of CMUT elements: a central row 930 of CMUT elements 920, and two outer rows 932 of CMUT elements 922. Each of rows 930 and 932 has N CMUT elements 920/922 (wherein N is an integer significantly greater than 3, such as 128 or 256) to form a 3×N array of CMUT elements 920/922. CMUT element 922 is similar to CMUT element 820, but may have smaller extent in the direction perpendicular to axis 890. CMUT element 920 is similar to CMUT element 920 except for having smaller extent than CMUT element 920 in the direction perpendicular to axis 890. Without departing from the scope hereof, 1.5D CMUT array 900 may include more rows of CMUT elements, such as a total of five rows. 1.5D CMUT array 900 allows for some degree of beamforming of ultrasound in the dimension perpendicular to axis 890, although the spatial resolution of beamforming in the dimension perpendicular to axis 890 is less than the spatial resolution of beamforming in the dimension parallel to axis 890. This beamforming may serve to electronically focus the ultrasound emitted by 1.5D CMUT array 900, in the dimension orthogonal to axis 890, to achieve focus at a desired distance away from the emission face of 1.5D CMUT array 900. 1.5D CMUT array 900 may be implemented with a lens, such as lens 510, for focusing of ultrasound in conjunction with electronic beamforming, or 1.5D CMUT array 900 may be implemented without lens 510 and rely on beamforming for focusing.

Figure 10:
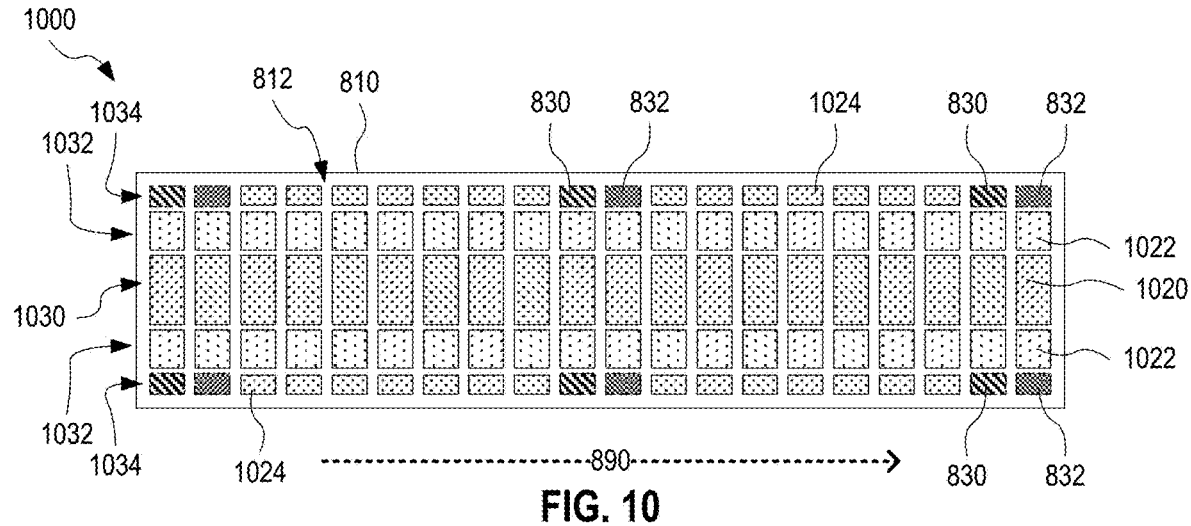
FIG. 10 illustrates a 1.75D CMUT array, according to an embodiment.

FIG. 10 illustrates a 1.75D CMUT array 1000. FIG. 10 shows a top plan view of ultrasound emission face 812 of 1.75D CMUT array 1000. 1.75D CMUT array 1000 is an embodiment of CMUT array 210 and of CMUT array 112. "1.75D" is a term of art in the field of beamforming. A 1.75D transducer array is a two-dimensional transducer array that (a) has high spatial resolution in first dimension and much more limited spatial resolution in an orthogonal second dimension, and (b) is operated in a manner that is asymmetrical about a line parallel to the first dimension and centered in the second dimension. For example, a 1.75D transducer array may have five rows, with 128 or 256 transducers in each row, to form an array with 5×128 or 5×256 transducers.

1.75D CMUT array 1000 is similar to 1.5D CMUT array 900 except for including additional rows of CMUT elements. 1.75D CMUT array 1000 includes five rows of CMUT elements: a central row 1030 of CMUT elements 1020, two rows 1032 of CMUT elements 1022 flanking row 1030, and two outer rows 1034 of CMUT elements 1024. Each of rows 1030, 1032 and 1034 has N CMUT elements 1020/1022/1024 (wherein N is an integer significantly greater than 5, such as 128 or 256) to form a 5×N array of CMUT elements 1020/1022/1024. CMUT element 1030 is similar to CMUT element 820, but may have smaller extent in the direction perpendicular to axis 890. CMUT element 1022 is similar to CMUT element 1020 except for having smaller extent than CMUT element 1020 in the direction perpendicular to axis 890, and CMUT element 1024 is similar to CMUT element 1022 except for having smaller extent than CMUT element 1022 in the direction perpendicular to axis 890. Without departing from the scope hereof, 1.75D CMUT array 1000 may include more rows of CMUT elements. 1.75D CMUT array 1000 allows for some degree of beamforming of ultrasound in the dimension perpendicular to axis 890, although the spatial resolution of beamforming in the dimension perpendicular to axis 890 is less than the spatial resolution of beamforming in the dimension parallel to axis 890. This beamforming may serve to electronically focus the ultrasound emitted by 1.75D CMUT array 1000, in the dimension orthogonal to axis 890, to achieve focus at a desired distance away from the emission face of 1.75D CMUT array 1000 as well as at a desired location along the dimension orthogonal to axis 890. 1.75D CMUT array 1000 may be implemented with a lens, such as lens 510, for focusing of ultrasound in conjunction with electronic beamforming, or 1.75D CMUT array 1000 may be implemented without lens 510 and rely on beamforming for focusing.

Figure 11:
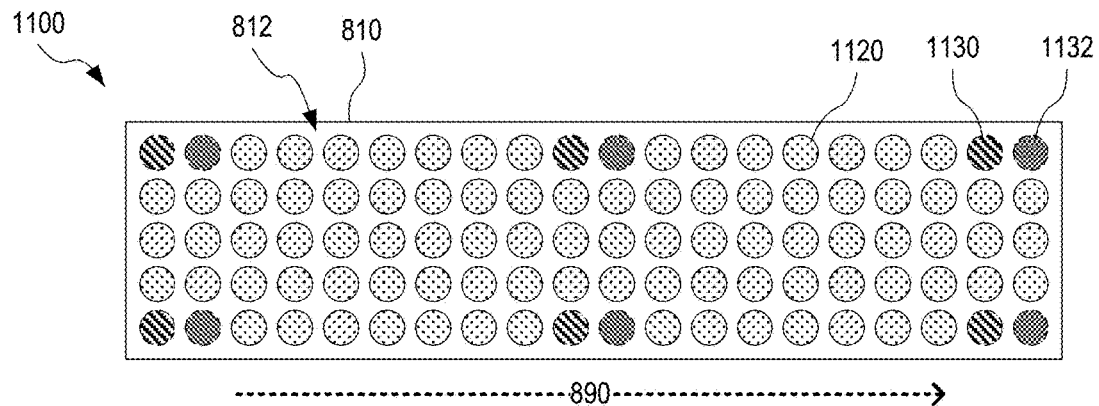
FIG. 11 illustrates a two-dimensional CMUT array, according to an embodiment.

FIG. 11 illustrates a two-dimensional (2D) CMUT array 1100 including a plurality of CMUT elements 1120 arranged in a 2D array. CMUT element 1120 is similar to CMUT element 820. FIG. 11 shows a top plan view of ultrasound emission face 812 of 2D CMUT array 1100. CMUT array 1100 is an embodiment of CMUT array 210 and of CMUT array 112. For clarity of illustration, FIG. 11 depicts 2D CMUT array 1100 as having 5×20 CMUT elements 1120, but 2D CMUT array 1100 may include a larger number of CMUT elements 1120, such as between 10×128 CMUT elements 1120 and 20×256 CMUT elements 1120. In certain embodiments, 2D CMUT array 1100 enables beamforming, in the dimension perpendicular to axis 890, of greater spatial resolution than the associate spatial resolution of beamforming provided by CMUT arrays 900 and 1000.

2D CMUT array 1100 may include sensors 1130 and/or sensors 1132. Sensor 1130 is similar to sensor 830, and sensor 1132 is similar to sensor 832. Each of sensors 1130/1132 may occupy one site in the array formed by CMUT elements 1120, such that this particular site has a sensor 1130/1132 instead of a CMUT element 1120. Alternatively, sensors 1130/1132 are positioned in locations that do not interfere with the 2D array of CMUT elements 1120. Without departing from the scope hereof, the shape of CMUT elements 1120 may be different from that shown in FIG. 11. For example, each CMUT element 1120 may be square, rectangular, or oval.

Figure 12A:
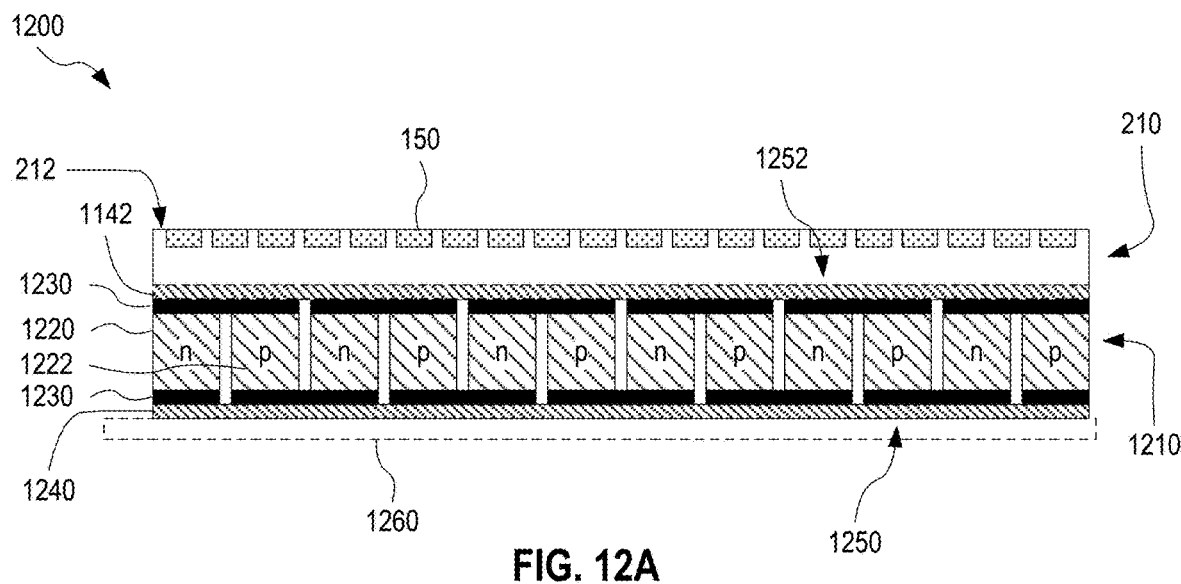
FIGS. 12A and 12B illustrate cross-sectional and top plan views, respectively, of a CMUT-TEC device, according to an embodiment.
Figure 12B:
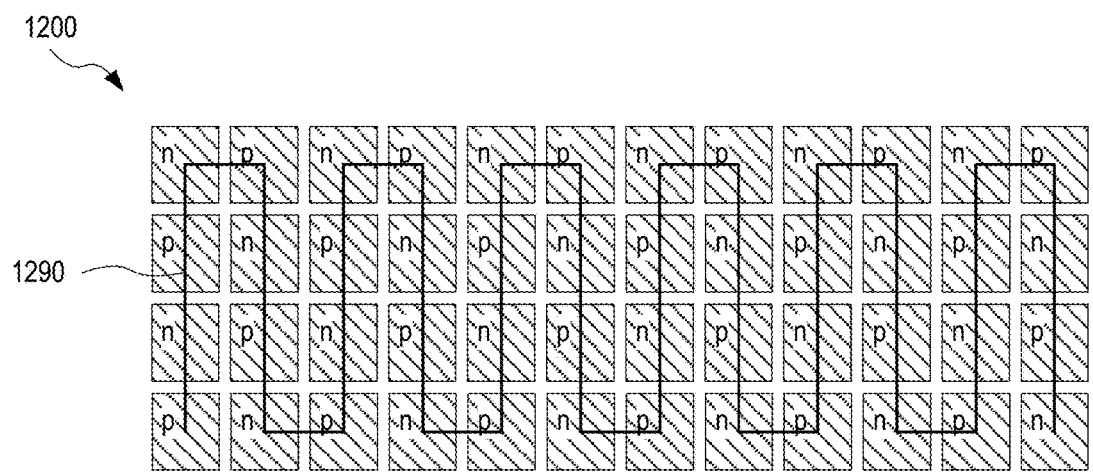

FIGS. 12A and 12B illustrate one CMUT-TEC device 1200. CMUT-TEC device 1200 is an embodiment of CMUT-TEC device 200. CMUT-TEC device 1200 includes a thermoelectric cooler 1210 with CMUT array 210 disposed or formed directly on thermoelectric cooler 1210. Thermoelectric cooler 1210 is an embodiment of thermoelectric cooler 220 or 114. FIG. 12A is a cross sectional view of CMUT-TEC device 1200, with the cross section taken in a plane perpendicular to ultrasound emission face 212 of CMUT array 210. FIG. 12B is a top plan view of the semiconductors of thermoelectric cooler 1210, with the view being in a direction from ultrasound emission face 212 toward the semiconductors of thermoelectric cooler 1210. FIGS. 12A and 12B are best viewed together in the following description.

Thermoelectric cooler 1210 includes a plurality of n-type semiconductors 1220 and a plurality of p-type semiconductors 1222 electrically coupled in series by electrodes 1230 such that the series alternates between the n-type semiconductors and the p-type semiconductors, as indicated by line 1290 in FIG. 12B. Without departing from the scope hereof, electrodes 1230 may be arranged differently from what is shown in FIGS. 12A and 12B, and line 1290 may take a different path. In addition, it should be understood that the number of n-type semiconductors 1220 and a plurality of p-type semiconductors 1222 may be different from what is shown in FIG. 12B. In operation, a voltage drop is applied across the series of n-type semiconductors 1220 and the plurality of p-type semiconductors 1222 to form a cold side 1252 of thermoelectric cooler 1210 facing CMUT array 210 and a hot side 1250 of thermoelectric cooler 1210 facing away from CMUT array 210. Thermoelectric cooler 1210 further includes a thermal conductor 1240 that thermally couples n-type semiconductors 1220 and p-type semiconductors 1222 on hot side 1250. Optionally, thermoelectric cooler 1210 also includes a thermal conductor 1242 that thermally couples n-type semiconductors 1220 and p-type semiconductors 1222 on cold side 1252. Alternatively, a portion of CMUT array 210 forms thermal conductor 1242. Each of thermal conductors 1240 and 1242 are electrical insulators. In one example, each of thermal conductors 1240 and 1242 are formed from a thin film of silicon dioxide, silicon nitride, or another thermally conductive dielectric.

CMUT-TEC device 1200 forms an embodiment of CMUT array 210 and thermoelectric cooler 220 as configured in CMUT-TEC device 500. Although not shown in FIG. 12A, CMUT-TEC device 1200 may further include lens 510 disposed on ultrasound emission face 212 of CMUT array 210.

In certain embodiments, CMUT-TEC device 1200 includes a solid thermal conductor 1260 that is thermally coupled to hot side 1250 and configured to conduct heat away from hot side 1250. Solid thermal conductor 1260 is an embodiment of solid thermal conductor 710.

Figure 13:
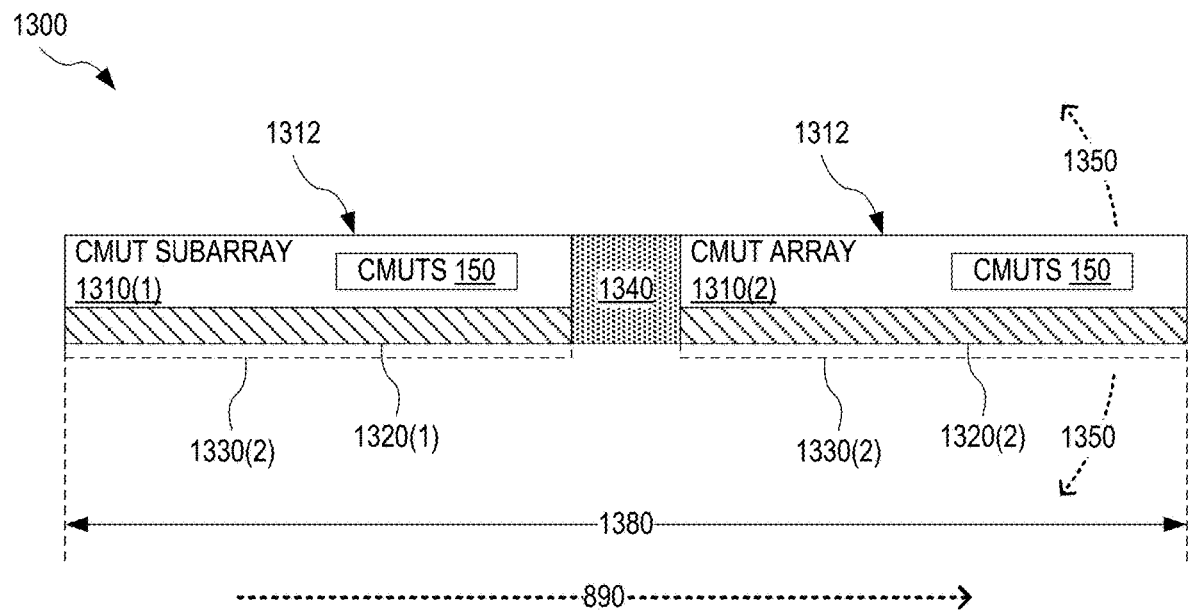
FIG. 13 illustrates a CMUT-TEC device with two planar CMUT subarrays having an adjustable angle therebetween, according to an embodiment.

FIG. 13 illustrates one CMUT-TEC device 1300 with two planar CMUT subarrays 1310(1) and 1310(2) having an adjustable angle therebetween. CMUT-TEC device 1300 is an embodiment of CMUT-TEC device 200. CMUT subarrays 1310(1) and 1310(2) are thermally coupled to respective thermoelectric coolers 1320(1) and 1320(2). Each instance of CMUT subarray 1310 paired with the respective thermoelectric cooler 1320 may be similar to CMUT-TEC device 1200. CMUT-TEC device 1300 may further include solid thermal conductors 1330(1) and 1330(2) that are thermally coupled to the hot sides of thermoelectric coolers 1320(1) and 1320(2), respectively.

CMUT-TEC device 1300 includes a hinge 1340 that enables pivoting of (a) CMUT subarray 1310(2) and associated thermoelectric cooler 1320(2) (and optionally solid thermal conductor 1330(2)) relative to (b) CMUT subarray 1310(1) and associated thermoelectric cooler 1320(1) (and optionally solid thermal conductor 1330(1)), as indicated by arrows 1350. This pivoting action may serve to direct ultrasound 270 generated by CMUT subarrays 1310 to target tissue 280 and/or improve the ability of CMUT-TEC device 1300 to conform to curvature of body channel 392.

CMUT-TEC device 1300 has extent 1380 in the direction along axis 890. Extent 1380 is, for example, in the range between 10 millimeters and 50 millimeters.

Figure 14:
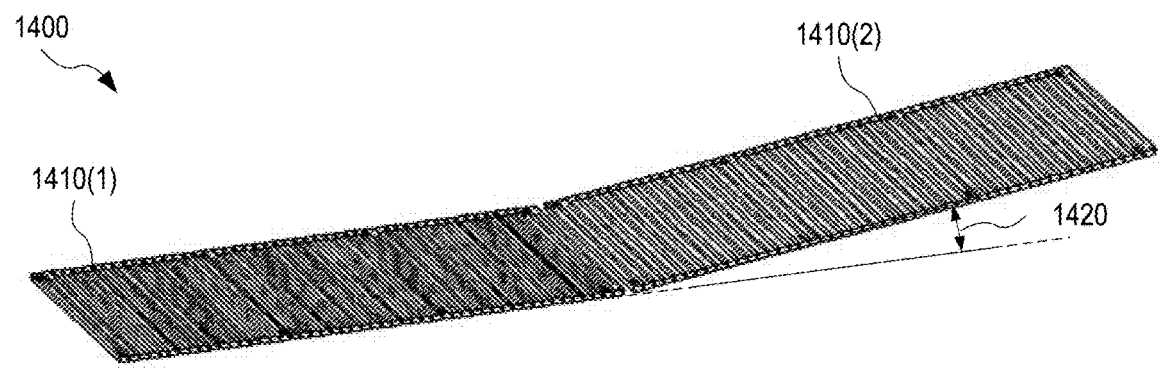
FIG. 14 illustrates a CMUT-TEC device with two planar CMUT subarrays having an adjustable angle therebetween, according to an embodiment.

FIG. 14 is a pictorial view of one CMUT-TEC device 1400 with two planar CMUT subarrays 1410(1) and 1410(2) having an adjustable angle therebetween. CMUT-TEC device 1400 is an embodiment of CMUT-TEC device 1300 that allows pivoting of CMUT subarray 1410(2) by an angle 1420 away from being coplanar with CMUT subarray 1410 (1). Angle 1420 is for example in the range up to 30 degrees, such as between 10 and 30 degrees.

Figure 15:
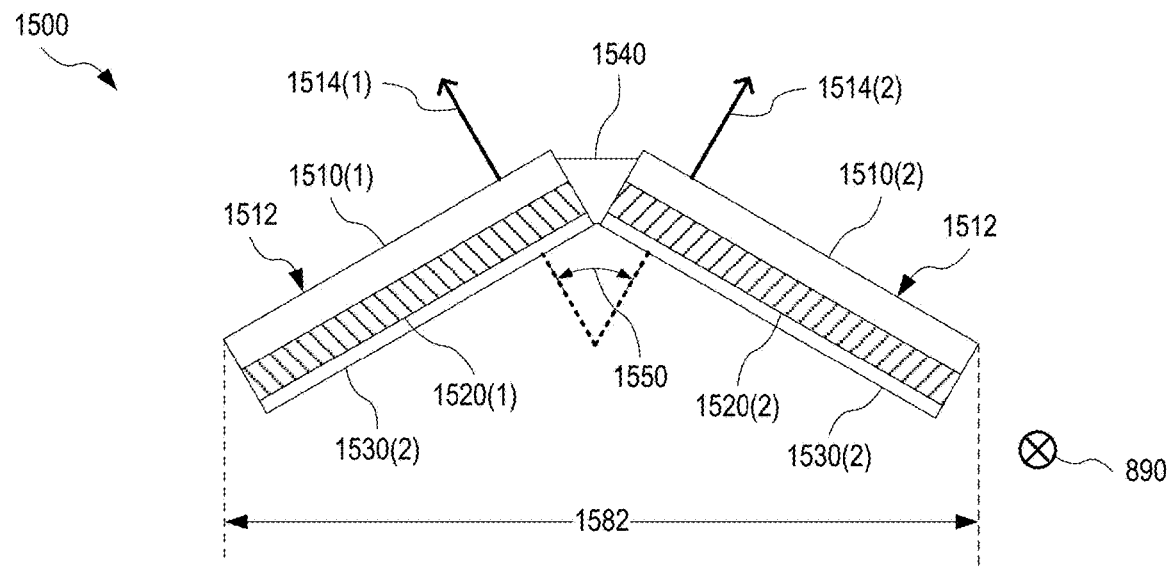
FIG. 15 illustrates a CMUT-TEC device with two planar CMUT subarrays angled away from each other, according to an embodiment.

FIG. 15 illustrates one CMUT-TEC device 1500 with two planar CMUT subarrays 1510(1) and 1510(2) angled away from each other. CMUT-TEC device 1500 is an embodiment of CMUT-TEC device 200. CMUT subarrays 1510(1) and 1310(2) are thermally coupled to respective thermoelectric coolers 1520(1) and 1520(2). Each instance of CMUT subarray 1510 paired with the respective thermoelectric cooler 1520 may be similar to CMUT-TEC device 1200. CMUT-TEC device 1500 may further include solid thermal conductors 1530(1) and 1530(2) that are thermally coupled to the hot sides of thermoelectric coolers 1520(1) and 1520(2), respectively. Without departing from the scope hereof, thermoelectric coolers 1520(1) and 1520(2) may be implemented as a single thermoelectric cooler that is thermally coupled to both CMUT subarray 1510(1) and 1510(2).

CMUT-TEC device 1500 includes a mechanical coupler 1540 that positions (a) CMUT subarray 1510(2) and associated thermoelectric cooler 1520(2) (and optionally solid thermal conductor 1530(2)) at an angle to (b) CMUT subarray 1510(1) and associated thermoelectric cooler 1520 (1) (and optionally solid thermal conductor 1530(1)), in such a manner that ultrasound emission faces 1512 of CMUT subarrays 1510 face away from each other to a certain extent. CMUT-TEC device 1500 thereby has greater angular range than that achievable by a single planar CMUT-TEC device. Each ultrasound emission face 1512 is substantially parallel to axis 890 such that, when implemented in catheter 110, CMUT-TEC device 1500 is oriented with each ultrasound emission face 1512 substantially parallel to the longitudinal axis of catheter 110. In implementations intended for ultrasound treatment of prostate 192 from urethra 194, the two ultrasound emission faces 1512 of CMUT-TEC device 1500 may facilitate simultaneous ultrasound exposure of a greater portion of prostate 192, for example such that less or no rotation of CMUT-TEC device 1500 is needed during ultrasound treatment of prostate 192.

In an embodiment, the angle between normal vectors 1514 of ultrasound emission faces 1512 is between 45 and 90 degrees, such as in the range between 60 and 65 degrees. Each CMUT subarray 1510 may be elongated in the dimension parallel to axis 890.

CMUT-TEC device 1500 has extent 1582 in a dimension orthogonal to axis 890. Extent 1582 is, for example, in the range between 2.5 millimeters and 3.5 millimeters or in the range between 2 and 5 millimeters, in an embodiment compatible with implementation in a urethral catheter.

Figure 16:
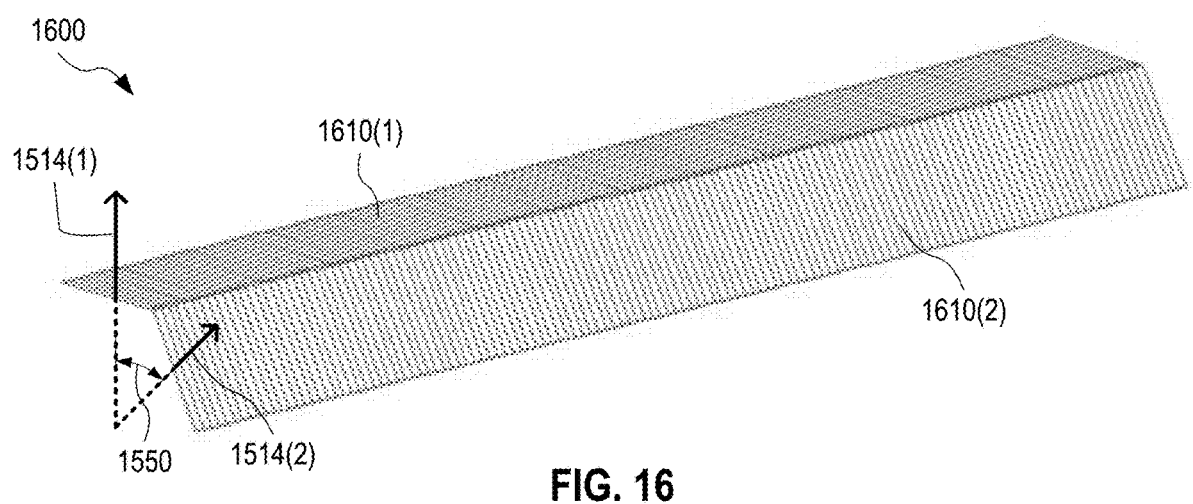
FIG. 16 illustrates a CMUT-TEC device with two planar CMUT subarrays angled away from each other, according to an embodiment.

FIG. 16 is a pictorial view of one CMUT-TEC device 1600 with two planar CMUT subarrays 1610(1) and 1610(2) angled away from each other. CMUT-TEC device 1600 is an embodiment of CMUT-TEC device 1500, wherein each CMUT subarray 1610 is elongated in the dimension parallel to axis 890.

Figure 17:
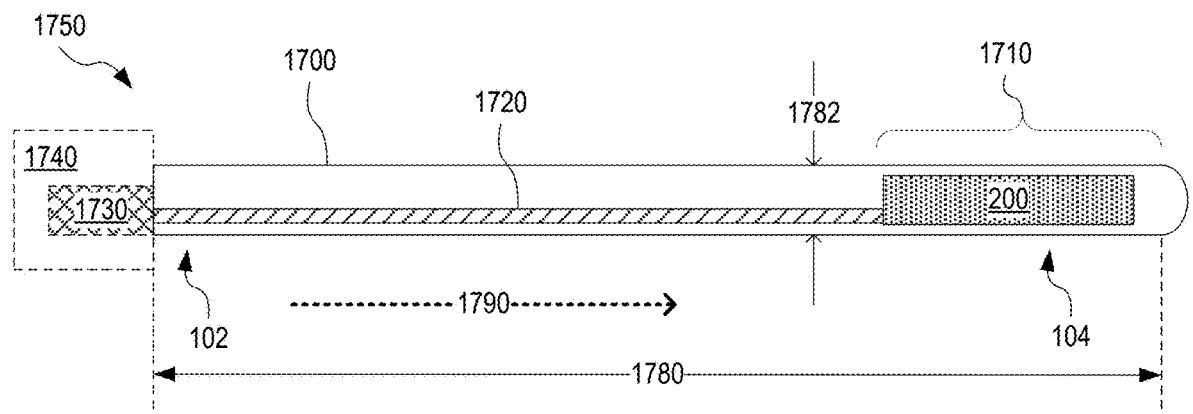
FIG. 17 illustrates a catheter with a CMUT-TEC transducer device, according to an embodiment.

FIG. 17 illustrates one catheter 1700 with a CMUT-TEC transducer device. FIG. 17 is a cross sectional view of catheter 1700 with the cross section being parallel to a longitudinal axis 1790 of catheter 1700. In one embodiment, catheter 1700 is rigid and straight such that the direction of longitudinal axis 1790 is always constant along the length of catheter 1700. In another embodiment, catheter 1700 is pliable and may be bent such that the direction of longitudinal axis 1790 may vary along the length of catheter 1700. In relation to this embodiment, the cross sectional view of FIG. 17 corresponds to a view of catheter 1700 in its straight configuration. Without departing from the scope hereof, catheter 1700 may be configured to always be bent, either in a rigid manner or a pliable manner. In this case, the cross sectional view of FIG. 17 corresponds to a straightened version of catheter 1700.

Catheter 1700 is an embodiment of catheter 110. Catheter 1700 includes CMUT-TEC device 200 and a solid thermal conductor 1720. Catheter 1700 contains CMUT-TEC device 200 in a catheter tip 1710 of catheter 1700 at distal end 104 of catheter 1700. Solid thermal conductor 1720 is coupled to thermoelectric cooler(s) 220 of CMUT-TEC device 200 and extends along catheter 1700 away from distal end 104 toward proximal end 102, to conduct heat away from thermoelectric cooler(s) 220.

In one embodiment, solid thermal conductor 1720 includes or is substantially composed of metal, such as copper, silver, and/or aluminum. In one example, solid thermal conductor 1720 is a metal rod, such as a copper rod. In another example, solid thermal conductor 1720 includes a plurality of braided metal wires, such as a plurality of braided copper wires. The braided metal wires may be configured to allow solid thermal conductor 1720 to flex, for example if the path available to solid thermal conductor 1720 is not straight. As discussed above in reference to FIG. 7 and solid thermal conductor 710, such flexibility may improve patient comfort when catheter 1700 is placed in body channel 392, in particular if catheter 1700 is left in body channel 392 for an extended period of time or if repositioning/reorientation of catheter 1700 is required. In another embodiment, solid thermal conductor 1720 includes or is substantially composed of a non-metallic thermal conductor, for example a thermally conductive nanomaterial such as thermally conductive nanofibers. In yet another embodiment, solid thermal conductor 1720 includes or is substantially composed of a thermally conductive nanocomposite. In a further embodiment, solid thermal conductor 1720 includes or is substantially composed of a metamaterial.

In the embodiment depicted in FIG. 17, solid thermal conductor 1720 extends all the way to the extreme of proximal end 102 to conduct at least a portion of the heat removed from CMUT-TEC device 200 out of catheter 1700. This embodiment of catheter 1700 may be implemented in a device 1750 together with a heat exchanger 1730 coupled to solid thermal conductor 1720 at or beyond proximal end 102. Heat exchanger 1730 cools solid thermal conductor 1720 outside the body channel into which catheter 1700 is inserted. Heat exchanger 1730 may employ liquid cooling or gas cooling. In one example, heat exchanger 1730 includes cooling fins for cooling of solid thermal conductor 1720. In another example, heat exchanger 1730 circulates liquid or gas by solid thermal conductor 1720 to cool solid thermal conductor 1720, at least during operation of CMUT-TEC device 200. Device 1750 may implement heat exchanger 1730 in a handle 1740. Handle 1740 is an embodiment of handle 120.

In an alternate embodiment, not shown in FIG. 17, solid thermal conductor 1720 extends only partway to proximal end 102. In this embodiment, solid thermal conductor 1720 may redistribute, along a portion of the length of catheter, heat removed from CMUT-TEC device 200, while taking advantage of the catheter to ensure that the temperature of the catheter wall in contact with non-target tissue does not exceed a set threshold. In one such example, solid thermal conductor 1720 uniformly redistributes the heat along at least part of catheter 1700 in the longitudinal direction (associated with longitudinal axis 1790). This embodiment of catheter 1700 may also be coupled with handle 1740 to form an alternate embodiment of device 1750 that includes handle 1740 but not heat exchanger 1730.

Catheter 1700 has extent 1780 along longitudinal axis 1790 and extent 1782 in dimension orthogonal to longitudinal axis 1790. The cross section of catheter 1700, orthogonal to axis 1790 may be circular, such that extent 1782 is a diameter. In one embodiment, extent 1780 is sufficiently long that distal end 104 can be positioned in body channel 392 at or near target tissue 380 while the proximate end 102 is at the exit of body channel 392 or outside body channel 392. In certain embodiments, extent 1782 is in the range from 2 to 10 millimeters. In one such embodiment, catheter 1700 is configured as a urethral catheter, and extent 1782 may be in the range from 3 to 7 millimeters, such as around 5 millimeters.

Figure 18:
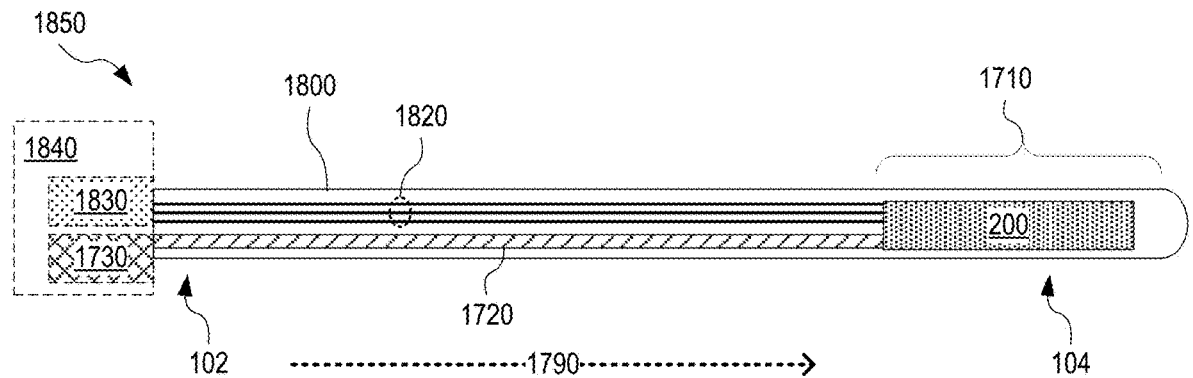
FIG. 18 illustrates another catheter with a CMUT-TEC device, according to an embodiment.

FIG. 18 illustrates another catheter 1800 with a CMUT-TEC device, in a cross sectional view similar to that used in FIG. 17. Catheter 1800 is an embodiment of catheter 1700, which further includes electrical connections 1820 from CMUT-TEC device 200 to proximal end 102. Electrical connections 1820 are configured to connect CMUT-TEC device 200 to external electronic circuitry 1830. Electronic circuitry 1830 includes (a) ultrasound driving circuitry generating drive signals that are transmitted to CMUT array 210 of CMUT-TEC device 200 via some of electrical connections 1820, and (b) Peltier driving circuitry that powers thermoelectric cooler(s) 220 of CMUT-TEC device 200 via other ones of electrical connections 1820. Electronic circuitry 1830 may further include circuitry that receives and processes ultrasound imaging signals received from CMUT array 210 via some of electrical connections 1820.

Catheter 1800 and electronic circuitry 1830 may be implemented together in a device 1850. In an embodiment, device 1850 includes a handle 1840 that contains electronic circuitry 1830. Handle 1840 may further include heat exchanger 1730.

Without departing from the scope hereof, at least some of electrical connections 1820 may serve to both (a) couple electronic circuitry 1830 to CMUT-TEC device 200 and (b) conduct heat away from thermoelectric cooler(s) 220 of CMUT-TEC device 200. In this case, electrical connections 1820 may replace solid thermal conductor 1720, or reduce the requirements to the heat conduction capacity of solid thermal conductor 1720. In one such example, some of electrical connections 1820 are coaxial cables and the outer conductors of the coaxial cables are thermally coupled to the hot side of thermoelectric cooler(s) 220 to remove heat from thermoelectric cooler(s) 220. Also without departing from the scope hereof, electronic circuitry 1830 may be implemented externally to device 1850, for example in or integrated with control module 140 externally to device 1850.

Figure 19:
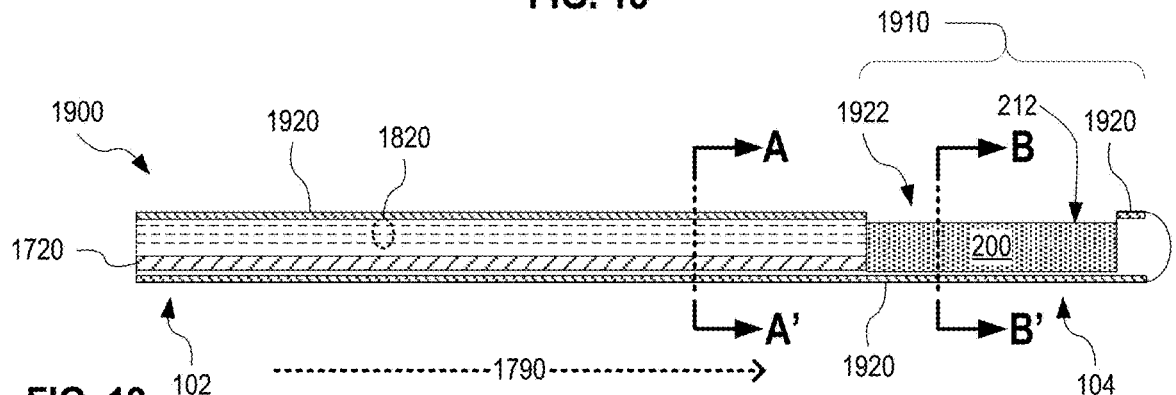
FIGS. 19, 20, and 21 illustrate a catheter with a CMUT-TEC device, according to an embodiment.
Figure 20:
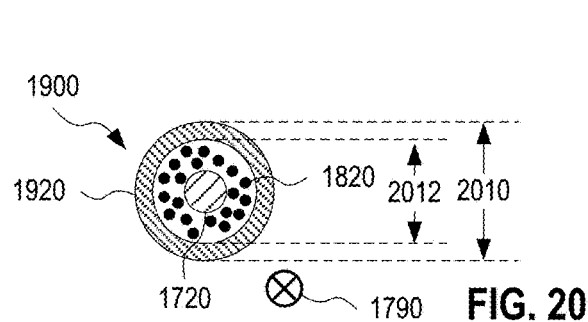
Figure 21:
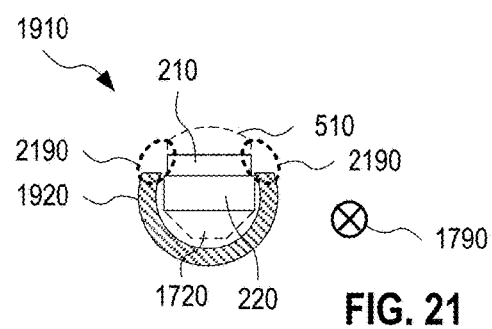

FIGS. 19-21 illustrate yet another catheter 1900 with a CMUT-TEC device. FIG. 19 shows catheter 1900 in a cross sectional view similar to that used in FIG. 17. FIG. 20 shows catheter 1900 in a cross sectional view indicated by line A-A' in FIG. 19. FIG. 21 shows a catheter tip 1910 of catheter 1900 in a cross sectional view indicated by line B-B' in FIG. 19. FIGS. 19-21 are best viewed together in the following description.

Catheter 1900 is an embodiment of catheter 1700. Catheter 1900 may further include electrical connections 1820, in which case catheter 1900 is an embodiment of catheter 1800. Catheter 1900 further includes a tubular catheter jacket 1920 defining the wall of catheter 1900. Tubular catheter jacket 1920 has a window 1922 positioned above ultrasound emission face 212 of CMUT-TEC device 200. Window 1922 may accommodate lens 510 or another material capable of transmitting ultrasound. Tubular catheter jacket 1920 has outer diameter 2010 and inner diameter 2012. In an embodiment configured for use as a urethral catheter, outer diameter 2010 is in the range from 3 to 7 millimeters, such as around 5 millimeters, and inner diameter 2012 is in the range from 2.5 to 6.5 millimeters, such as around 4 millimeters. Tubular catheter jacket may be rigid or pliable. In one embodiment, tubular catheter jacket includes or is substantially composed of a metal, such as stainless steel. This embodiment of tubular catheter jacket 1920 is rigid. In another embodiment, tubular catheter jacket 1920 includes or is substantially composed of a polymer. This embodiment of tubular catheter jacket 1920 may be rigid or pliable. Tubular catheter jacket 1920 contains solid thermal conductor 1720 and, when included, electrical connections 1820 (see FIG. 20). The positioning of solid thermal conductor 1720 and optional electrical connections 1820 may be different from that shown in FIG. 20, without departing from the scope hereof. For example, solid thermal conductor 1720 may be located closer to the wall defined by tubular catheter jacket 1920.

In certain embodiments, tubular catheter jacket 1920 is thermally insulating to prevent or reduce transport of heat, conducted by solid thermal conductor 1720 (and/or electrical connections 1820), through the wall of tubular catheter jacket 1920. When catheter 1900 is positioned in a body channel 392 (see FIG. 3 or FIG. 6), such thermal insulation of tubular catheter jacket 1920 helps prevent heat-induced damage to wall 390 due to heat escaping catheter 1900. In one scenario, thermal insulation of tubular catheter jacket 1920 prevents solid thermal conductor 1720 from burning wall 390. In one thermally insulating embodiment, tubular catheter jacket 1920 includes or is substantially composed of a solid material that is a poor thermal conductor, such as a polymer or rubber. In another thermally insulating embodiment, tubular catheter jacket 1920 includes or is substantially composed of a porous material with the pores resulting in a low thermal conductivity of the porous material. In yet another thermally insulating embodiment, tubular catheter jacket 1920 includes a vacuum layer.

In an alternative embodiment, insulating outer sheaths of electrical connections 1820 at least partly thermally insulates solid thermal conductor 1720 from tubular catheter jacket 1920, such that tubular catheter jacket 1920 may be thermally conductive or at least be a less effective thermal insulator. In such embodiments, solid thermal conductor 1720 may advantageously be surrounded by electrical connections 1820.

Although depicted in FIG. 21 as having sharp edges and gaps in the regions 2190 near sides of CMUT array 210 (and optional lens 510), catheter tip 1910 may be configured with a smooth outer surface to improve patient comfort and prevent damage to the body channel into which catheter 1900 is inserted, without departing from the scope hereof. In one example, the contour of catheter tip 1910 in regions 2190, and optionally also at lens 510, is a continuation of the contour of tubular catheter jacket 1920.

Figure 22:
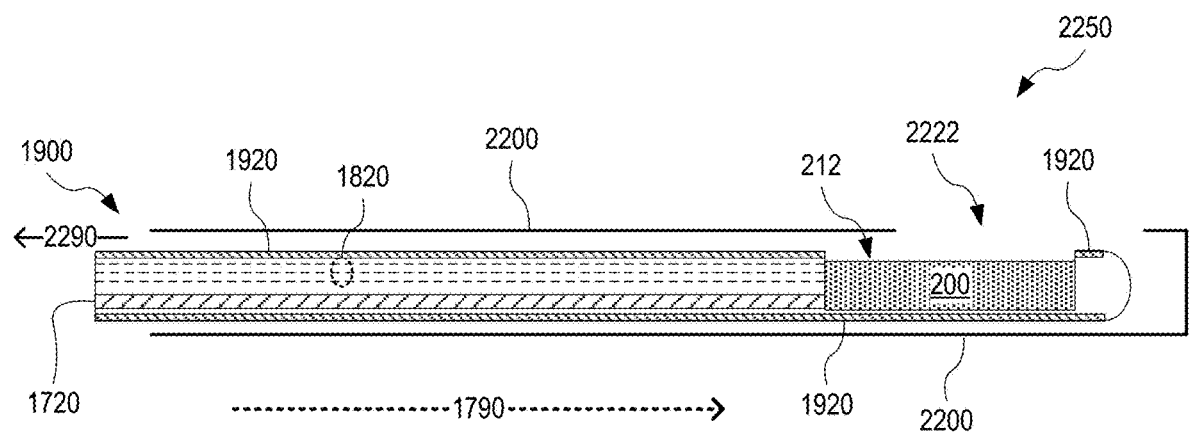
FIG. 22 illustrates a catheter sleeve configured to encase a catheter with a CMUT array and solid state cooling in a removable fashion, according to an embodiment.

FIG. 22 illustrates one catheter sleeve 2200 configured to encase catheter 1900 in a removable fashion. FIG. 22 shows catheter sleeve 2200 and catheter 1900 in a cross sectional view similar to that used in FIG. 19. In one use scenario, catheter sleeve 2200 is placed over catheter 1900 prior to insertion of catheter 1900 into body channel 392 to treat target tissue 380 with ultrasound. After ultrasound treatment, catheter 1900 is extracted from catheter sleeve 2200 and from body channel 392 along direction 2290, while catheter sleeve 2200 stays in body channel 392. In a modification to this use scenario, catheter sleeve 2200 is first inserted into body channel 392 without catheter 1900, whereafter catheter 1900 is inserted into catheter sleeve 2200 to position catheter 1900 in body channel 392. Catheter sleeve 2200 may remain in body channel 392 (e.g., urethra 194) for some time after ultrasound treatment of target tissue 380 (e.g., prostate 192) by catheter 1900, so as to monitor temperature and/or pressure of wall 390 (e.g., the wall of urethra 194 near prostate 192). In addition, catheter sleeve 2200 may serve to keep body channel 392 open after ultrasound treatment, for example until a treatment induced swelling has subsided. In embodiments, where catheter sleeve 2200 is configured for use in urethra 194 to aid ultrasound treatment of prostate 192, catheter sleeve 2200 may be left in urethra 194 after ultrasound treatment to prevent complete blockage of urethra, otherwise potentially resulting from treatment induced swelling, and allow passage of urine from bladder 196 through catheter sleeve 2200.

Catheter sleeve 2200 has a window 2222. When catheter 1900 is fully inserted into catheter sleeve 2200, window 2222 is positioned over ultrasound emission face 212 of CMUT-TEC device 200. Window 2222 may be an actual opening, or window 2222 may be covered by a material that is capable of transmitting ultrasound. In an alternative embodiment, catheter sleeve 2200 has no window 2222. In this alternative embodiment, all of catheter sleeve 2200 or the portion of catheter sleeve 2200 is made of an ultrasound transmitting material, such as plastic. In one implementation, the ultrasound transmitting material encircles the region occupied by CMUT-TEC device 200 during treatment, to enable ultrasound exposure in 360 degrees. This implementation of catheter sleeve 2200 may provide access to all of prostate 192 from urethra 194 with no need for rotating catheter sleeve 2200 relative to urethra 194.

Catheter sleeve 2200 may be rigid or pliable, or a combination thereof. For example, a distal portion of catheter sleeve 2200 configured to accommodate catheter tip 1910 may be rigid, while a more proximal portion is pliable. A fully or partly pliable embodiment of catheter sleeve 2200 may be compatible with a rigid or pliable embodiment of catheter 1900.

Catheter sleeve 2200 may include a thermally insulating layer, or be substantially composed of a thermally insulating material, such that catheter sleeve 2200 is capable of protecting wall 390 from heat conducted by solid thermal conductor 1720.

Figure 23:
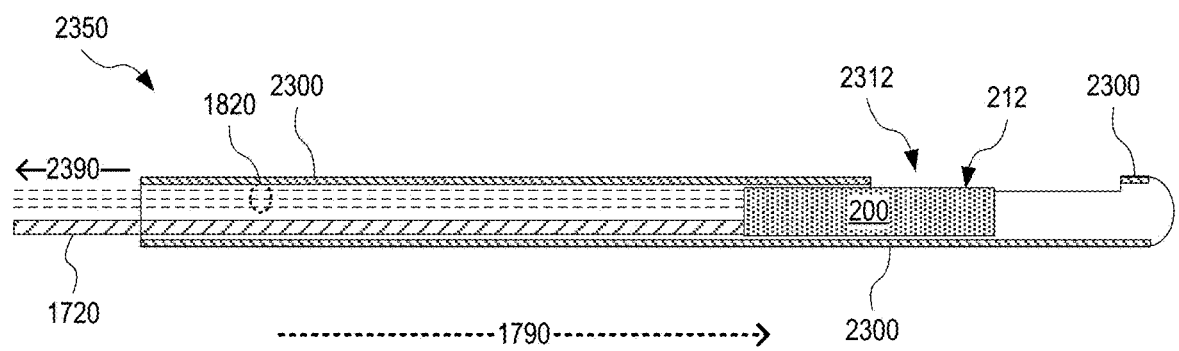
FIG. 23 illustrates a catheter with a CMUT-TEC device, employing a tubular catheter jacket permitting removal of the CMUT-TEC device, according to an embodiment.

FIG. 23 illustrates one catheter 2350 with CMUT-TEC device 200, employing a tubular catheter jacket 2300 permitting removal of CMUT-TEC device 200 and associated electrical and thermal connections therefrom. Catheter 2350 is an embodiment of catheter 1900 that implements tubular catheter jacket 1920 as a removable tubular catheter jacket 2300, thus allowing for extraction of CMUT-TEC device 200, solid thermal conductor 1720, and optional electrical connections 1820 from tubular catheter jacket 2300 along direction 2390. The function of removable tubular catheter jacket 2300 may be similar to that of catheter sleeve 2200 discussed above in reference to FIG. 22.

Tubular catheter jacket 2300 has a window 2312. When CMUT-TEC device 200 is fully inserted into tubular catheter jacket 2300, window 2312 is positioned over ultrasound emission face 212 of CMUT-TEC device 200. Window 2312 may be an actual opening, or window 2312 may be a material that is capable of transmitting ultrasound.

Together, tubular catheter jacket 2300, CMUT-TEC device 200, solid thermal conductor 1720, and, optionally, electrical connections 1820 form a catheter 2350.

Figure 24:
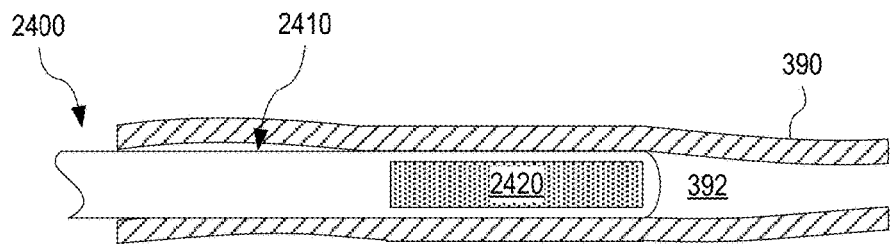
FIG. 24 illustrates a catheter or catheter sleeve with solid state cooling, according to an embodiment.

FIG. 24 illustrates one catheter or catheter sleeve 2400 with solid state cooling. Catheter/catheter sleeve 2400 includes a tubular wall 2410 and at least one thermoelectric cooler 2420 coupled to tubular wall 2410. Tubular wall 2410 is configured to be inserted into body channel 392, and thermoelectric cooler(s) 2420 are configured to cool at least a portion of wall 390 of body channel 392. Thermoelectric cooler(s) 2420 may cool wall 390 through direct physical contact between thermoelectric cooler(s) 2420 and wall 390, or thermoelectric cooler(s) 2420 may cool wall 390 through thermal coupling via tubular wall 2410. Tubular wall 2410 is, for example, a tubular catheter jacket or a tubular wall of a catheter sleeve. In the latter case, the catheter sleeve may encase other parts of catheter/catheter sleeve 2400, such as thermoelectric cooler 2420, in a removable manner similar to that discussed for catheter sleeve 2200. In addition to thermoelectric cooler(s) 2420, catheter/catheter sleeve 2400 may contain other functionality that serves one or more other purposes than cooling of wall 390.

Tubular wall 2410 may be rigid or pliable. In one embodiment, tubular wall 2410 includes or is substantially composed of a metal, such as stainless steel. This embodiment of tubular wall 2410 is rigid. In another embodiment, tubular wall 2410 includes or is substantially composed of a polymer. This embodiment of tubular wall 2410 may be rigid or pliable, or a combination thereof.

Figure 25:
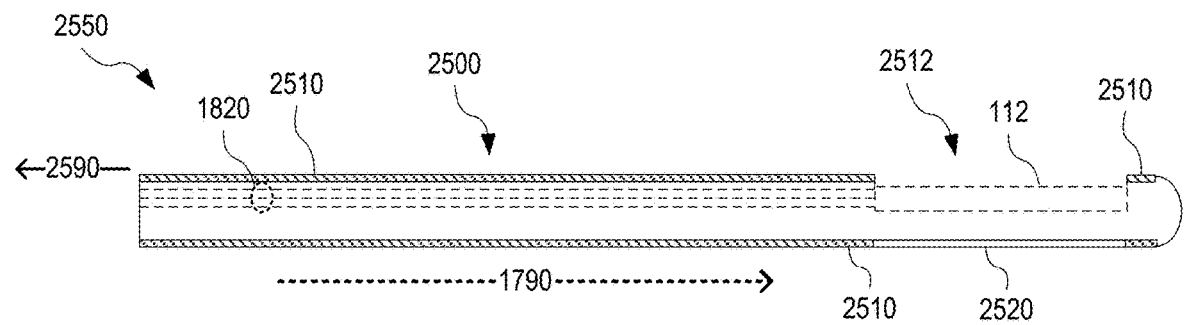
FIG. 25 illustrates a catheter or catheter sleeve having at least one thermoelectric cooler coupled to its tubular wall, according to an embodiment.

FIG. 25 illustrates one catheter or catheter sleeve 2500 having at least one thermoelectric cooler 2520 coupled to its tubular wall 2510. Catheter/catheter sleeve 2500 is an embodiment of catheter/catheter sleeve 2400, wherein the thermoelectric cooling is implemented in or on tubular wall 2410 to be thermally coupled to wall 390 of body channel 392. Catheter/catheter sleeve 2500 may also form an embodiment of tubular catheter jacket 1920. In the embodiment shown in FIG. 25, each thermoelectric cooler 2520 is on the outside of tubular wall 2510. In this embodiment, each thermoelectric cooler 2520 may be in direct physical contact with wall 390 to cool wall 390. In another embodiment, each thermoelectric cooler 2520 is on the inside of tubular wall 2510 or formed within the material of tubular wall 2510, such that each thermoelectric cooler 2520 is thermally coupled to wall 390 when an associated portion of tubular wall 2510 is thermally coupled to wall 390. In one use scenario, thermoelectric cooler(s) 2520 cool a portion of wall 390 prior to or after ultrasound treatment of target tissue 280 through this portion of wall 390. In this scenario, catheter/catheter sleeve 2500 may be rotated in body channel 392 between cooling and ultrasound treatment such that a thermoelectric cooler(s) 2520 are placed in contact with a portion of wall 390 before and/or after CMUT array 112 is positioned to expose target tissue 280 to ultrasound through this portion of wall 390.

In certain embodiments, catheter/catheter sleeve 2500 is configured to accommodate CMUT array 112 and associated electrical connections 1820 inside tubular wall 2510, and thus form a catheter 2550 for ultrasound treatment of target tissue 280 with solid state cooling of non-target tissue 290. In such embodiments of catheter 2550, tubular wall 2510 may form or include a window 2512 that permits ultrasound emission from CMUT array 112 to target tissue 280. Window 2512 may be similar to window 2312. Catheter 2550 is an embodiment of catheter 110 implementing an embodiment of CMUT-TEC device 200 that has (a) an embodiment of thermoelectric cooler(s) 114 coupled to the catheter wall and (b) CMUT array 112 within the space contained by the catheter wall. Together, CMUT array 112 and thermoelectric cooler(s) 114 form an embodiment of CMUT-TEC device 200.

In one embodiment of catheter 2550, tubular wall 2510 permits extraction of CMUT array 112 and associated electrical connections 1820 from tubular wall 2510 along direction 2590. This embodiment of tubular wall 2510 cooperates with thermoelectric cooler(s) 2520 to form an embodiment of tubular catheter jacket 2300 that further includes thermoelectric cooler(s) 2520. The associated embodiment of catheter 2550 is similar to catheter 2350, except that thermoelectric cooler(s) 2520 of catheter 2550 are coupled to tubular wall 2510.

Figure 26:
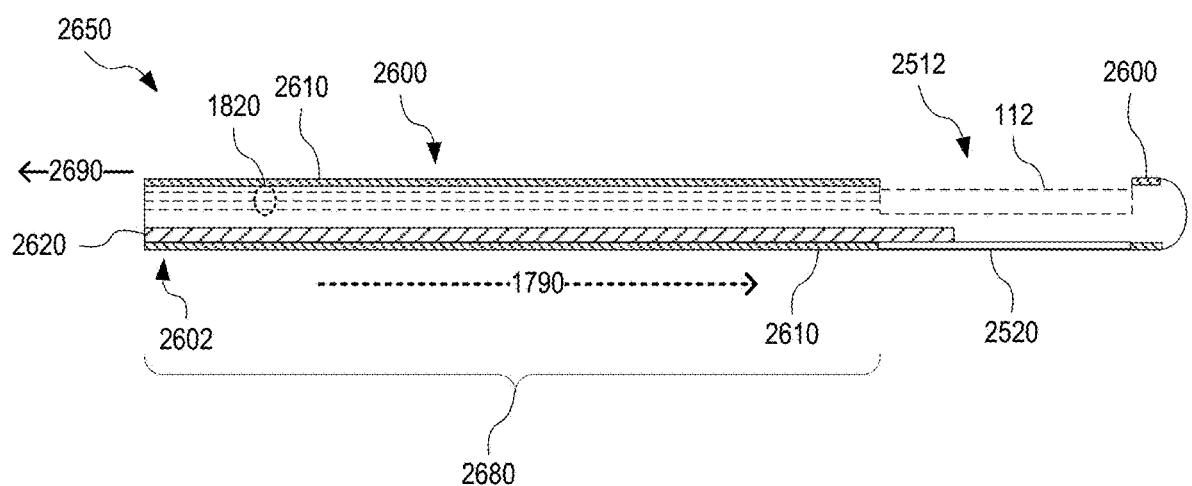
FIG. 26 illustrates a catheter or catheter sleeve that has at least one thermoelectric cooler and a solid thermal conductor coupled to its tubular wall, according to an embodiment.

FIG. 26 illustrates another catheter or catheter sleeve 2600 that has at least one thermoelectric cooler 2520 and a solid thermal conductor 2620 mechanically coupled to its tubular wall 2610. Catheter/catheter sleeve 2600 is an embodiment of catheter/catheter sleeve 2500, tubular wall 2610 is an embodiment of tubular wall 2510, and solid thermal conductor 2620 is an embodiment of solid thermal conductor 1720. Solid thermal conductor 2620 is thermally coupled to thermoelectric cooler(s) 2520 to conduct heat away from the hot side of thermoelectric cooler(s) 2520 during operation of thermoelectric cooler(s) 2520.

To avoid direct physical contact between solid thermal conductor 2620 and wall 390, solid thermal conductor 2620 is located on the inside of tubular wall 2610, at least over the portion 2680 of tubular wall 2610 that is away from thermoelectric cooler(s) 2520. Tubular wall 2610 may be thermally insulating to further prevent transport of heat from solid thermal conductor 2620 through tubular wall 2610, and thus protect portions of wall 390 in contact with tubular wall 2610 from heat induced damage. Thermally insulated embodiments of tubular wall 2610 may be composed of materials similar to those discussed above in reference to FIG. 19 for tubular catheter jacket 1920. Alternatively, if tubular wall 2610 is a thermal conductor, solid thermal conductor 2620 may be thermally isolated from tubular wall 2610.

Although shown in FIG. 26 as extending all the way to the proximal end 2602 of tubular wall 2610, solid thermal conductor 2620 may extend only partway from thermoelectric cooler(s) 2520 toward proximal end 2602, as discussed above in reference to FIG. 17 and solid thermal conductor 1720.

In certain embodiments, catheter/catheter sleeve 2600 is configured to accommodate CMUT array 112 and associated electrical connections 1820 inside tubular wall 2610, in a manner similar to that discussed above in reference to FIG. 25 and catheter/catheter sleeve 2500, and thus form a catheter 2650 for ultrasound treatment of target tissue 280 with solid state cooling of non-target tissue 290. In such embodiments of catheter 2650, tubular wall 2610 may include window 2512 to permit ultrasound emission from CMUT array 112 to target tissue 280. Catheter 2650 is an embodiment of catheter 1800 or 1900.

In one embodiment of catheter 2650, tubular wall 2610 permits extraction of CMUT array 112 and associated electrical connections 1820 from tubular wall 2610 along direction 2690. This embodiment of tubular wall 2610 cooperates with thermoelectric cooler(s) 2520 and solid thermal conductor 2620 to form an embodiment of tubular catheter jacket 2300 that further includes thermoelectric cooler(s) 2520 and solid thermal conductor 2620. The associated embodiment of catheter 2650 is similar to catheter 2350, except that thermoelectric cooler(s) 2520 and solid thermal conductor 2620 of catheter 2650 are coupled to tubular wall 2610.

Figure 27A:
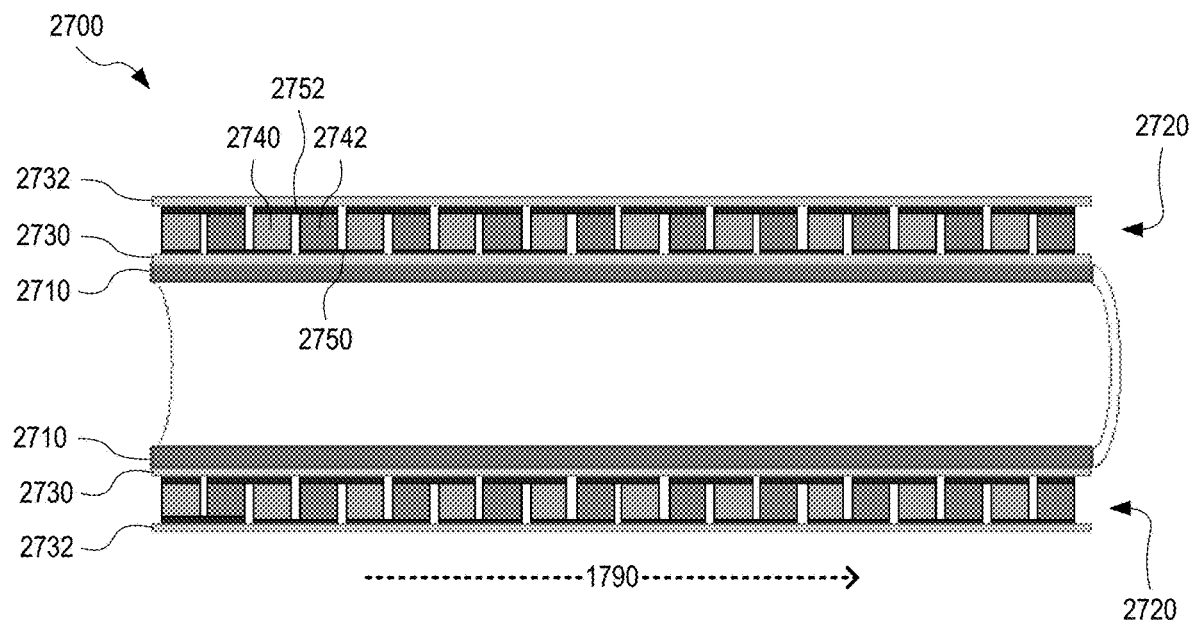
FIGS. 27A and 27B illustrate a catheter or catheter sleeve with thermoelectric cooling, according to an embodiment.
Figure 27B:
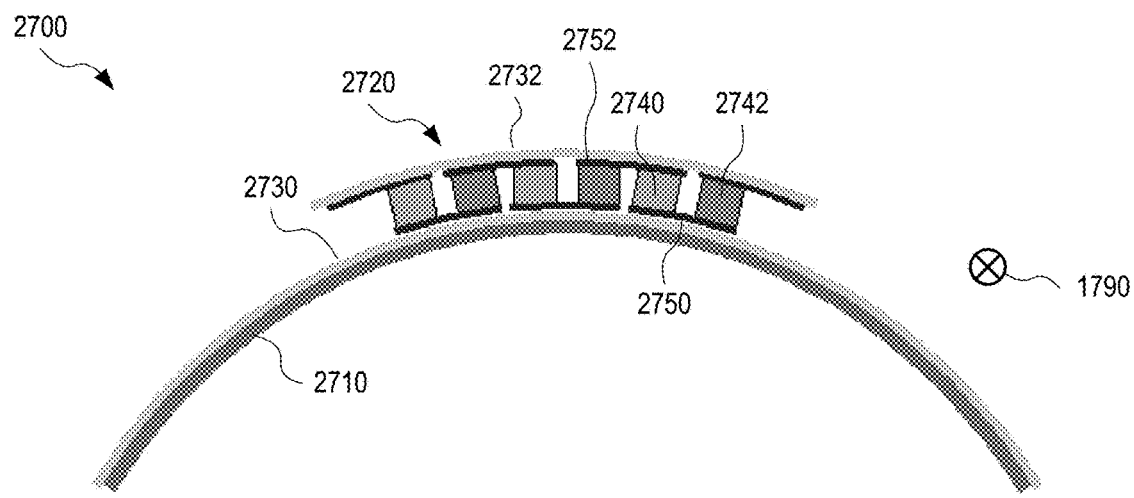

FIGS. 27A and 27B illustrate one catheter or catheter sleeve 2700 with thermoelectric cooling. Catheter/catheter sleeve 2700 is an embodiment of catheter/catheter sleeve 2500. FIGS. 27A and 27B are orthogonal cross sectional views of catheter/catheter sleeve 2700 and are best viewed together in the following description. Catheter/catheter sleeve 2700 includes a tubular wall 2710 and one or more thermoelectric coolers 2720 on the outside of tubular wall 2710. Thermoelectric cooler(s) 2720 may span around the circumference of tubular wall 2710, or cover only one or more sections along the circumference of tubular wall 2710. Thermoelectric cooler 2720 is an embodiment of thermoelectric cooler 2520 and may be implemented in either one of catheter/catheter sleeve 2500 and catheter/catheter sleeve 2600.

Each thermoelectric cooler 2720 includes (a) a thermal conductor 2730 disposed on tubular wall 2710, (b) a thermal conductor 2732 a distance away from tubular wall 2710, and (c) a plurality of n-type semiconductors 2740 and a plurality of p-type semiconductors 2742 electrically coupled in series by metal electrodes 2750 and 2752 such that the series alternates between n-type semiconductors 2740 and p-type semiconductors 2742. Thermal conductors 2730 and 2732 are electrical insulators. In operation, a voltage drop is applied across the series of n-type semiconductors 2740 and p-type semiconductors 2742 to form a cold side at thermal conductor 2732, which is capable of cooling wall 390 of body channel 392.

In one embodiment, at least the portion of tubular wall 2710 supporting thermoelectric cooler(s) 2720 is rigid, and n-type semiconductors 2740 and p-type semiconductors 2742 are rigidly coupled in a configuration that matches the curvature of tubular wall 2710. In another embodiment, at least the portion of tubular wall 2710 supporting thermoelectric cooler(s) 2720 is pliable, and metal electrodes 2750 and 2752 and thermal conductors 2730 and 2732 are flexible, such that thermoelectric cooler(s) 2720 are capable of conforming to bending of the associated portion of tubular wall 2710.

Although not shown in FIG. 27B, the outer surface of catheter/catheter sleeve 2700 may be smooth. Also without departing from the scope hereof, thermoelectric coolers 2720 may replace a portion of tubular wall 2710. Additionally, thermoelectric coolers 2720 may be implemented on the inside of tubular wall 2710 and thermally coupled to tubular wall 2710, without departing from the scope hereof. In this implementation, at least a section of tubular wall 2710, to which tubular wall 2710 is thermally coupled, is thermally conducting to allow thermoelectric coolers 2720 to cool of wall 390 of body channel 392 through tubular wall 2710. One such implementation is discussed below in reference to FIGS. 28A-D.

Figure 28A:
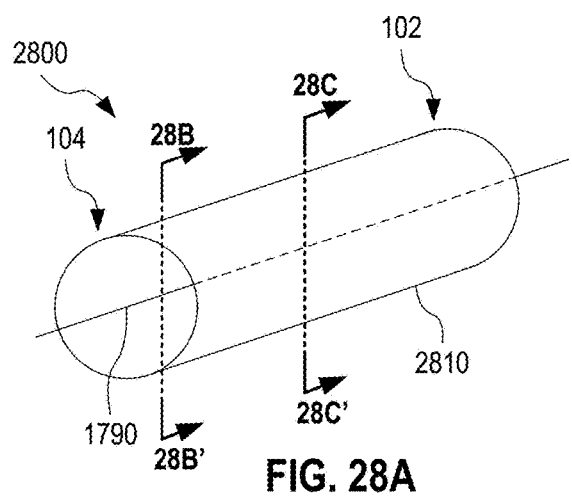
FIGS. 28A-28D illustrate another catheter or catheter sleeve with thermoelectric cooling, according to embodiments.
Figure 28B:
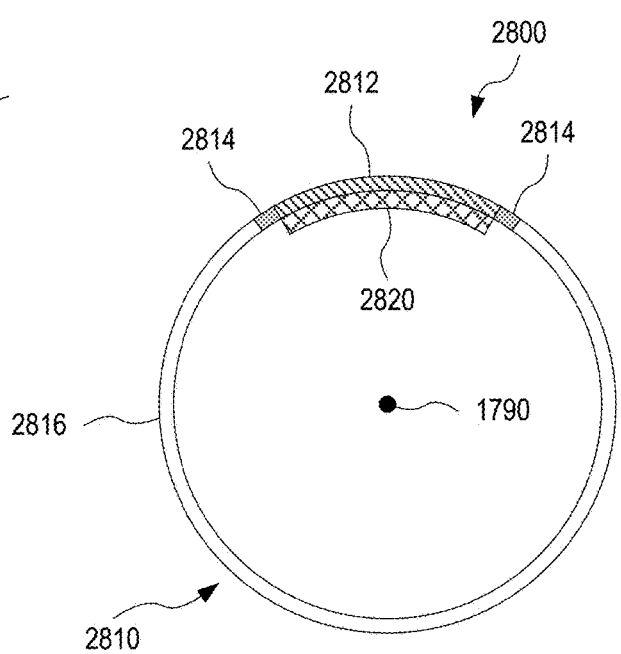
Figure 28C:
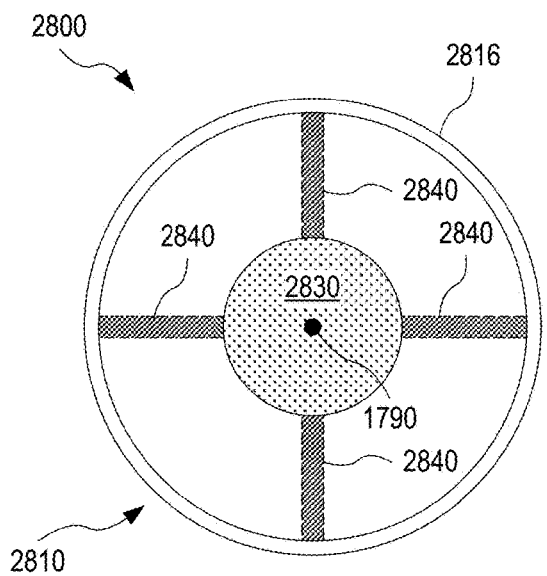

FIGS. 28A-D illustrate another catheter or catheter sleeve 2800 with thermoelectric cooling. Catheter/catheter sleeve 2800 is an embodiment of catheter/catheter sleeve 2500. FIG. 28A is a perspective view of catheter/catheter sleeve 2800. FIG. 28B is a cross sectional view of catheter/catheter sleeve 2800 taken near distal end 104 of catheter/catheter sleeve 2800 in a plane orthogonal to longitudinal axis 1790 (see arrow 28B-28B' of FIG. 28A). FIG. 28C is a cross sectional view of catheter/catheter sleeve 2800 taken further toward proximal end 102 of catheter/catheter sleeve 2800 in a plane orthogonal to longitudinal axis 1790 (see arrow 28C-28C' of FIG. 28A). FIGS. 28A-C are best viewed together in the following description.

Catheter/catheter sleeve 2800 includes (a) a tubular wall 2810, (b) one or more thermoelectric coolers 2820 that is thermally and mechanically coupled to a thermally conductive pad 2812 of tubular wall 2810, and (c) a solid thermal conductor 2830 thermally coupled to the thermoelectric cooler(s) 2820. In operation, the cold side of each thermoelectric cooler is in thermal connection with tubular wall 2810, and the hot side of each thermoelectric cooler is in thermal connection with solid thermal conductor 2830. Thermoelectric cooler 2820 is an embodiment of thermoelectric cooler 2520 and may be implemented in either one of catheter/catheter sleeve 2500 and catheter/catheter sleeve 2600. Each thermoelectric cooler 2820 may be of a construction similar to that of thermoelectric cooler 2720. Tubular wall 2810 is an embodiment of tubular wall 2510 of catheter/catheter sleeve 2500 and of tubular wall 2610 of catheter/catheter sleeve 2600. In tubular wall 2810, thermally conductive pad 2812 is surrounded by a thermal insulator 2814 that thermally isolates thermally conductive pad 2812 from a thermally conductive portion 2816 of tubular wall 2810. Thermally conductive portion 2816 is, for example, all of tubular wall 2810 except thermally conductive pad 2812 and thermal insulator 2814. In one implementation, thermally conductive portion 2816 is metal, such as stainless steel. Thermally conductive pad 2812 may be a metal as well.

The thermal isolation of thermally conductive pad 2812 from other portions of tubular wall 2810 limits the area of tubular wall 2810 (and thus adjacent tissue in contact with tubular wall 2810) that is cooled by thermoelectric cooler(s) 2820. This area limitation may facilitate more effective cooling by thermoelectric cooler(s) 2820, compared to the cooling achievable if thermoelectric cooler(s) 2820 was in thermal connection with a significantly greater portion of tubular wall 2810 or all of tubular wall 2810 (which could result in overloading of thermoelectric cooler(s) 2820).

Solid thermal conductor 2830 is disposed inside tubular wall 2810 and extends from thermoelectric cooler(s) 2820 toward proximate end 102. Solid thermal conductor 2830 may extend all the way the proximate end 102, or only partway to proximate end 102. Solid thermal conductor 2830 is an embodiment of solid thermal conductor 1720. In an embodiment, catheter/catheter sleeve 2800 is configured to redistribute heat, conducted by solid thermal conductor 2830, to tubular wall 2810, while taking advantage of the thermal mass of tubular wall 2810 to accommodate the heat while keeping the temperature at an acceptable level. In this embodiment, solid thermal conductor 2830 is in thermal connection with thermally conductive portion 2816 over an extended portion of tubular wall 2810, for example via one or more thermal connectors 2840, such that heat from thermally conductive pad 2812 is redistributed to a significantly greater portion of tubular wall 2810. Even though the temperature of this greater portion of tubular wall 2810 increases during this process and potentially heats adjacent tissue, the area of the greater portion of tubular wall 2810, over which the heat is redistributed, may be sufficiently large that the temperature increase is within an acceptable range. In another embodiment, solid thermal conductor 2830 is mechanically supported by non-thermally conductive bridges so as to prevent solid thermal conductor 2830 from forming a thermal short with tubular wall 2810.

In any cross section along the length of catheter/catheter sleeve 2800 that is occupied by solid thermal conductor 2810, the number of thermal connectors 2840 may be smaller or greater than the four thermal connectors 2840 depicted in FIG. 28C, without departing from the scope hereof. Furthermore, one or more thermal connectors 2840 may be slab-shaped and bridge between solid thermal conductor 2830 and tubular wall 2810 along an extended segment of longitudinal axis 1790. Alternatively, several rod-shaped thermal connectors 2840, each connecting to a respective local portion of tubular wall 2810, may cooperate to redistribute the heat to a larger portion of tubular wall 2810. In one implementation, thermal connector(s) 2840 are arranged to uniformly, or at least approximately uniformly, redistribute the heat over a segment of tubular wall 2810. The shape and thickness of thermal connector(s) 2840 may be a function of position along longitudinal axis 1790 to achieve this uniform, or approximately uniform, heat redistribution.

Without departing from the scope hereof, thermally conductive pad 2812 may function as the cold-side thermal conductor of thermoelectric cooler(s) 2820.

Figure 28D:
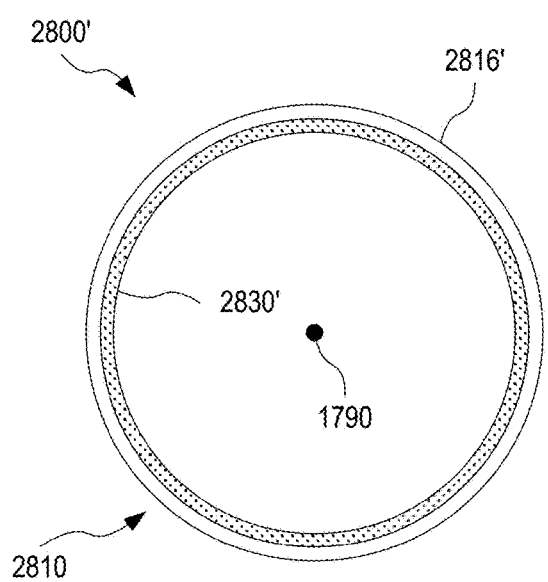

FIG. 28D illustrates an alternate embodiment 2800' of catheter/catheter sleeve 2800. FIG. 28 is a cross sectional view of catheter/catheter sleeve 2800', with the cross section taken in the same manner as for FIG. 28C. Catheter/catheter sleeve 2800' is similar to catheter/catheter sleeve 2800 except that (a) thermally conductive portion 2816 of tubular wall 2810 is replaced by a thermally insulating portion 2816' and (b) solid thermal conductor 2830 and optional thermal connectors 2840 are replaced by solid thermal conductor 2830'. Solid thermal conductor 2830' is a hollow cylindrical conductor disposed inside tubular wall 2810, for example adjacent to or even directly on the inner surface of thermally insulating portion 2816'. In one implementation, solid thermal conductor 2830' extends all the way to proximate end 102 and is configured to conduct at least a portion of the heat out of tubular wall 2810, for example to a heat exchanger. In another implementation, the thermal mass of solid thermal conductor 2830' is sufficient to accommodate the heat captured by thermoelectric cooler(s) 2820 while still allowing for effective cooling by thermoelectric cooler(s) 2820. The thickness of solid thermal conductor 2830' may be a function of position along longitudinal axis 1790 to achieve optimal heat redistribution and heat removal away from thermoelectric cooler(s) 2820.

In an embodiment, thermally insulating portion 2816' is flexible (e.g., a flexible polymer) and solid thermal conductor 2830' is a braided wire connector, such that catheter/catheter sleeve 2810 is flexible along at least a part of its length. This flexibility may increase patient comfort.

Figure 29:
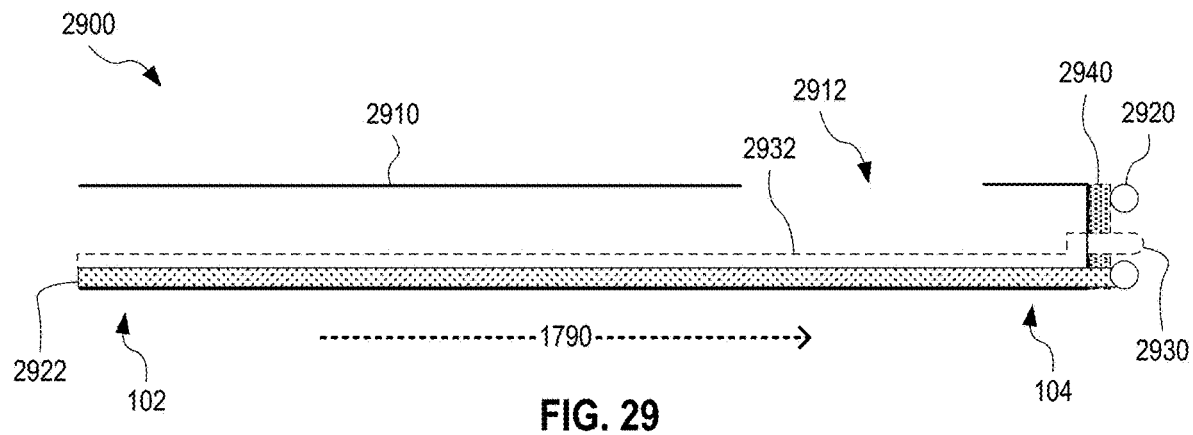
FIG. 29 illustrates a catheter sleeve configured to encase a catheter for ultrasound treatment of target tissue from inside a body channel while being secured to a portion of the body channel, according to an embodiment.

FIG. 29 illustrates one catheter sleeve 2900 configured to encase a catheter for ultrasound treatment of target tissue 280 from inside body channel 392 while being secured to a wider portion of body channel 392. In one use scenario, catheter sleeve 2900 encases catheter 1700 or catheter 2400.

Catheter sleeve 2900 may form an embodiment of catheter sleeve 2200. Alternatively, catheter sleeve 2900 is configured to permanently encase the catheter.

Catheter sleeve 2900 includes a tubular casing 2910 having a window 2912 capable of transmitting ultrasound emitted by an ultrasound transducer array of a catheter, such as CMUT array 210 or CMUT array 112. Window 2912 may be an opening or a material that is capable of transmitting ultrasound. Catheter sleeve 2900 further includes an inflatable balloon 2920 mounted on distal end 104 of catheter sleeve 2900, and a conduit 2922 that leads a fluid to inflatable balloon 2920 for inflation thereof, so as to secure inflatable balloon to a wider portion of body channel 392. Optionally, catheter sleeve 2900 further includes a rotation joint 2940 that permits rotation of tubular casing 2910 relative to inflatable balloon 2920. Rotation joint 2940 may facilitate rotation of CMUT array 210 about longitudinal axis 1790 when CMUT array 210 is coupled with catheter sleeve 2900. In one example, rotation joint 2940 allows for rotation of CMUT array 210 within a range from −135 degrees to +135 degrees. In one embodiment, rotation joint 2940 is configured to permit a discrete plurality of orientations of CMUT array 210 about longitudinal axis 1790, for example at every 5 or 10 degrees.

Catheter sleeve 2900 may further include a fluid port 2930 at distal end 104 and a conduit 2932 that passes a fluid received from a part of body channel 392 via fluid port 2930, through catheter sleeve 2900, to proximate end 102, and out of catheter sleeve 2900.

Catheter sleeve 2900 may be coupled with an external fluid handling system that supplies a fluid for inflating inflatable balloon 2920 via conduit 2922 and, optionally, accepts a fluid from body channel 392 via conduit 2932.

Tubular casing 2910 may be rigid or pliable, or a combination thereof.

Figure 30:
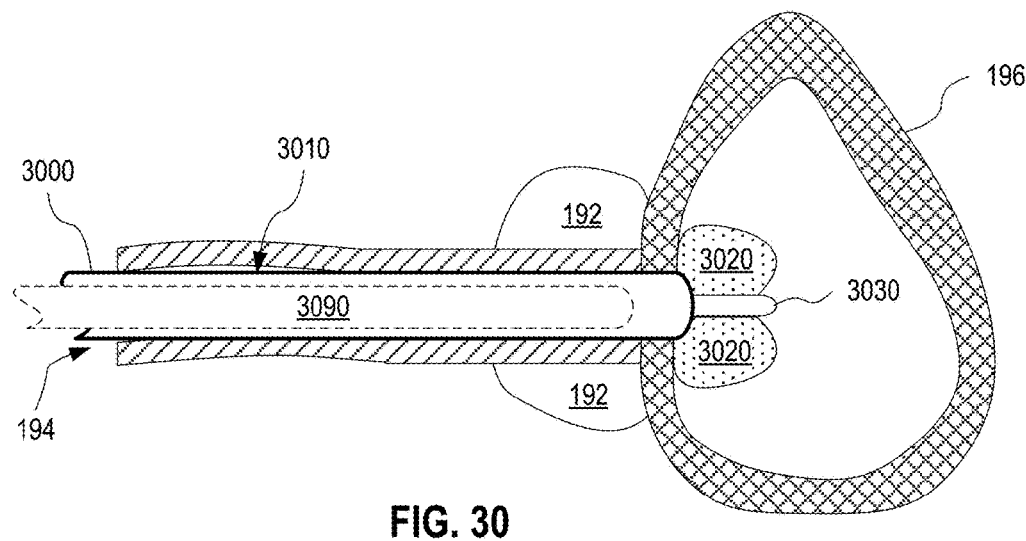
FIG. 30 illustrates a urethral catheter sleeve configured to encase a urethral catheter for ultrasound treatment of a prostate from inside the urethra while being secured to the bladder, according to an embodiment.

FIG. 30 illustrates one urethral catheter sleeve 3000 configured to encase a urethral catheter 3090 for ultrasound treatment of prostate 192 from inside urethra 194 while being secured to bladder 196. Urethral catheter 3090 is, for example, an embodiment of catheter 1700 or catheter 2400. Catheter sleeve 3000 is an embodiment of catheter sleeve 2900 specifically adapted for ultrasound treatment of prostate 192 from urethra 194. Catheter sleeve 3000 may form an embodiment of catheter sleeve 2200. Alternatively, catheter sleeve 3000 is configured to permanently encase the urethral catheter. For clarity of illustration, FIG. 30 does not show fluid conduit(s) of catheter sleeve 3000 and optional rotation joint 2940.

In operation, catheter sleeve 3000 is inserted into urethra 194, together with urethral catheter 3090 or prior to insertion of urethral catheter 3090 into catheter sleeve 3000. Next, an inflatable balloon 3020 of catheter sleeve 3000 is inflated to secure catheter sleeve 3000 to bladder 196. Catheter sleeve 3000 facilitates positioning of a tip of urethral catheter 3090 at prostate 192, to expose prostate 192 to ultrasound emitted by the tip of urethral catheter 3090, for example using CMUT array 210 or CMUT array 112. In one example of use, urethral catheter 3090 is extracted from catheter sleeve 3000 after ultrasound treatment of prostate 192 by urethral catheter 3090, while catheter sleeve 3000 is left in place for a longer period of time. In another example of use, catheter sleeve 3000 and urethral catheter 3090 are removed from urethra 194 together. Removal of catheter sleeve 3000 from urethra 194 takes place after deflation of inflatable balloon 3020.

Although not shown in FIG. 30, it should be understood that catheter sleeve 3000 may include conduit 2932 to pass urine from bladder 196 through catheter sleeve 3000 and out of urethra 192.

Tubular casing 3010 may be rigid or pliable, or a combination thereof. In one example, a portion of tubular casing 3010 spanning from bladder 196 and through the region near prostate 192 is rigid to prevent collapse of urethra 194 due to prostate pressure and allow passage of urine from bladder 196 through catheter sleeve 3000 and out of urethra 194, while the remaining more proximal portion of tubular casing 3010 is pliable for patient comfort.

Figure 31:
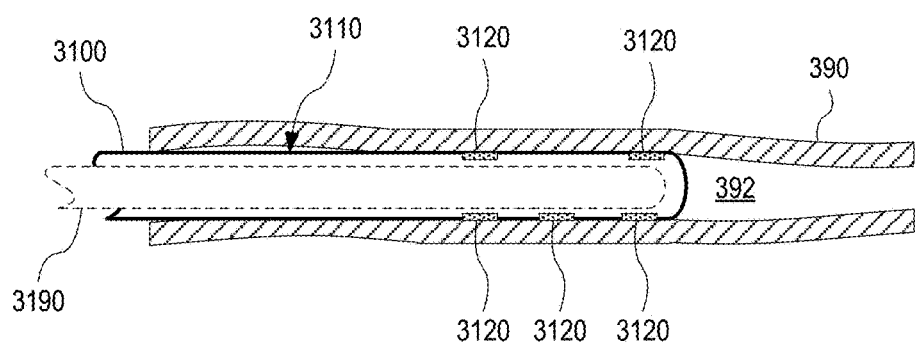
FIG. 31 illustrates a catheter sleeve with one or more integrated sensors for within the body channel, according to an embodiment.

FIG. 31 illustrates one catheter sleeve 3100 with one or more integrated sensors for sensing at least one property of wall 390 when catheter sleeve 3100 is within body channel 392. Catheter sleeve 3100 includes a tubular casing 3110 and one or more sensors 3120 that are coupled to tubular casing 3110. Sensor 3120 is similar to sensor 230. Tubular casing 3110 is configured to encase a catheter 3190. Catheter 3190 is, for example, an embodiment of catheter 110. In one embodiment, each sensor 3120 is a temperature sensor. In another embodiment, each sensor 3120 is a pressure sensor. In yet another embodiment, catheter sleeve 3100 includes both pressure and temperature sensors 3120.

In an exemplary use scenario, catheter sleeve 3100 remains in body channel 392 for some time after extraction of catheter 3190 therefrom. For example, catheter sleeve 3100 may remain in body channel 392 (e.g., urethra 194) for some time after ultrasound treatment of target tissue 380 (e.g., prostate 192) by catheter 110, so as to monitor temperature and/or pressure of wall 390 (e.g., the wall of urethra 194 near prostate 192). In addition, catheter sleeve 3100 may serve to keep body channel 392 open after ultrasound treatment, for example until a treatment induced swelling has subsided. In embodiments, where catheter sleeve 3100 is configured for use in urethra 194 to aid ultrasound treatment of prostate 192, catheter sleeve 3100 may be left in urethra 194 after ultrasound treatment to prevent complete blockage of urethra, otherwise potentially resulting from treatment induced swelling, and allow passage of urine from bladder 196 through catheter sleeve 3100.

Embodiments of catheter sleeve 3100 including a plurality of sensors 3120 may determine one or more properties of wall 390 (such as temperature and/or pressure) as a function of position, so as to obtain spatially resolved information about the one or more properties.

Tubular casing 3110 may be rigid or pliable. In one embodiment, tubular casing 3110 includes or is substantially composed of a metal, such as stainless steel. This embodiment of tubular casing 3110 is rigid. In another embodiment, tubular casing 3110 includes or is substantially composed of a polymer. This embodiment of tubular casing 3110 may be rigid or pliable, or a combination thereof.

Each of catheter sleeves 2200, 2900, and 3000 may include one or more sensors 3120 and thus forms an embodiment of catheter sleeve 3100. Furthermore, each of tubular catheter jackets 1920 and 2300, and each of tubular walls 2410, 2510, 2610, and 2710 may have one or more sensors 3120 coupled thereto.

Figure 32:
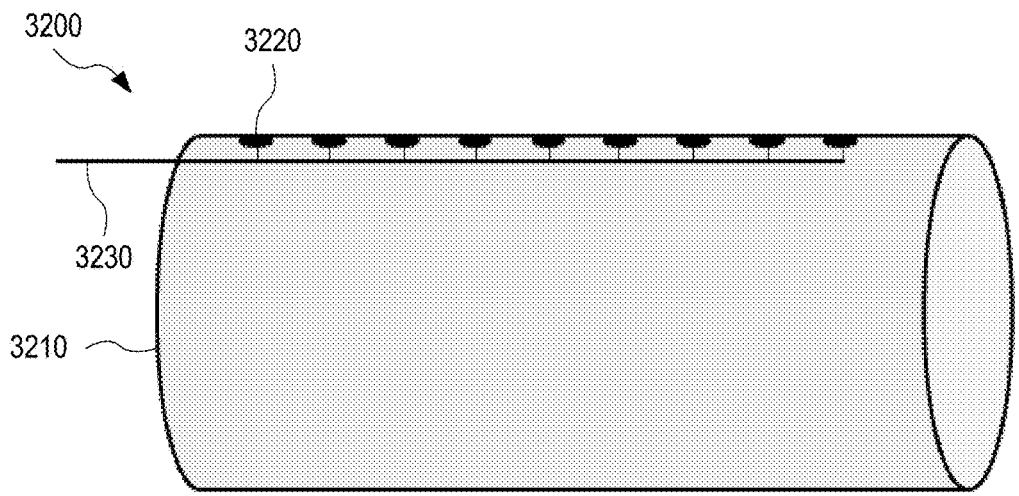
FIG. 32 illustrates a catheter sleeve having one or more hardwired sensors on its tubular casing, according to an embodiment.

FIG. 32 illustrates one catheter sleeve 3200 having one or more hardwired sensors 3220 on its tubular casing 3210. Each sensor 3220 is configured to sense a property of wall 390 when catheter sleeve 3200 is positioned in body channel 392. Sensor 3220 is an embodiment of sensor 3120. Catheter sleeve 3200 is an embodiment of catheter sleeve 3100 that includes electrical connections 3230 from sensor(s) 3220 to external electronic circuitry (not shown in FIG. 32) located outside body channel 392, so as to facilitate readout of sensor signals from sensor(s) 3220 via hardwired electrical connections in catheter sleeve 3200. In an embodiment, each sensor 3220 is an active sensor that requires power, and electrical connections 3230 further serve to provide such power to each sensor 3220.

In an embodiment, at least a portion of catheter sleeve 3100 is formed of a pliable polymer having at least a portion of electrical connections 3230 embedded therein or disposed thereon while maintaining the flexibility of the pliable polymer.

Figure 33:
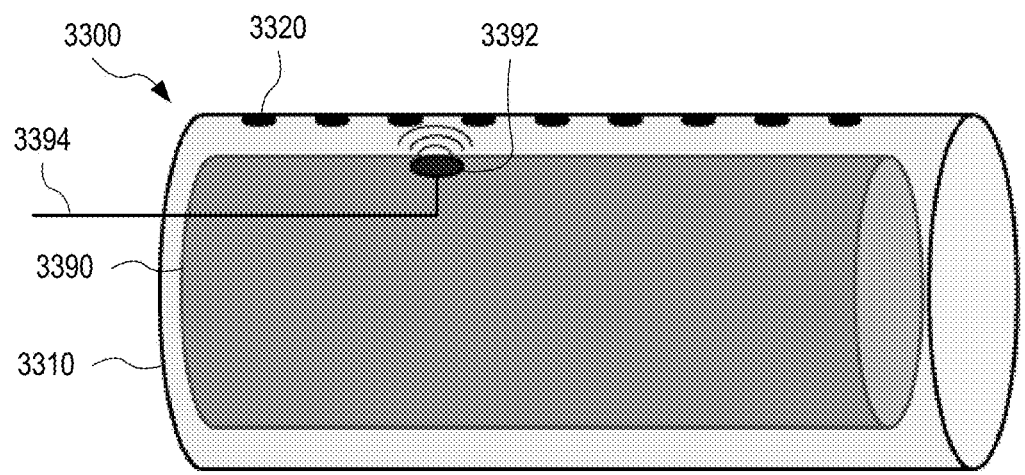
FIG. 33 illustrates a catheter sleeve having one or more wireless-communication based sensors on its tubular casing, wherein each sensor is read out by a catheter inserted into the catheter sleeve, according to an embodiment.

FIG. 33 illustrates one catheter sleeve 3300 having one or more wireless-communication based sensors 3320 on its tubular casing 3310, wherein each sensor 3320 is read out by a catheter 3390 inserted into catheter sleeve 3300. Catheter 3390 may be inserted into catheter sleeve 3300 when readout of sensor(s) 3320 is required and does not need to remain in catheter sleeve 3300 at other times. Each sensor 3320 is capable of sensing a property of wall 390 when catheter sleeve 3300 is positioned in body channel 392. Sensor 3320 is an embodiment of sensor 3120. Catheter sleeve 3300 is an embodiment of catheter sleeve 3100 configured for readout of sensor signals from sensor(s) 3320 via catheter 3390. Catheter 3390 may be dedicated to readout of sensor(s) 3320, or be a ultrasound treatment catheter, such as catheter 110, with additional sensor readout capability. Catheter 3390 includes at least one reader 3392 that communicates with sensor 3320 via a radio-frequency signal and receives a sensor signal from sensor 3320 in the form of a radio-frequency signal. Reader 3392 may further emit a radio-frequency signal to sensor 3320 to activate sensor 3320.

Each sensor 3320 may be a passive sensor that does not require power. Alternatively, each sensor 3320 is an active sensor that is activated by a radio-frequency signal emitted by reader 3392.

In one embodiment, catheter 3390 includes a single reader 3392, catheter sleeve 3300 includes several sensors 3320, and catheter 3390 is moved to sequentially position reader 3392 to read out different ones of sensors 3320. In another embodiment, catheter sleeve 3300 includes several sensors 3320, and catheter 3390 includes a single reader 3392 that has wireless range sufficient to read each of sensors 3320 without moving reader 3392. In yet another embodiment, catheter sleeve 3300 includes several sensors 3320, and catheter 3390 includes a corresponding set of readers 3392 positioned to match the positions of sensor 3320, such that each reader 3392 reads out a respective sensor 3320 with no need to move catheter 3390 between readings of different sensors 3320.

Catheter 3390 includes one or more electrical connections 3394 that couple each reader 3392 to electronic readout circuitry outside body channel 392.

In an embodiment, a portion of catheter 3390 includes a ruler or markings. The ruler/markings are located on a portion of catheter 3390 that is external to and/or located at the exit of body channel 392 when catheter 3390 is positioned in catheter sleeve 3300 to read out sensors 3320. The ruler/markings guides an operator to position electrical contact(s) 3392 in locations that match sensor(s) 3320. In one implementation, the ruler/markings provide visual feedback to the operator. In another embodiment, catheter sleeve 3300 and catheter 3390 are cooperatively configured to define a preferred seating position of catheter 3390 inside catheter sleeve 3300 for each sensor 3320. To read out a given sensor 3320, the operator "clicks" catheter 3390 into the preferred seating position associated with this sensor 3320. In this embodiment, catheter 3390 may further have one or more markings located on a portion of catheter 3390 that is external to and/or located at the exit of body channel 392 when catheter 3390 is positioned in catheter sleeve 3300 to read out sensors 3320, wherein each marking visually indicates an associated seating position of catheter 3390 to the operator.

In an alternative embodiment, each sensor 3320 is configured for wireless readout from outside body channel 392. In this embodiment, sensor(s) 3320 may be configured to cooperate with a wireless readout circuit (for example similar to reader 3392) positioned near subject 190 and sensor(s) 3320.

Figure 34:
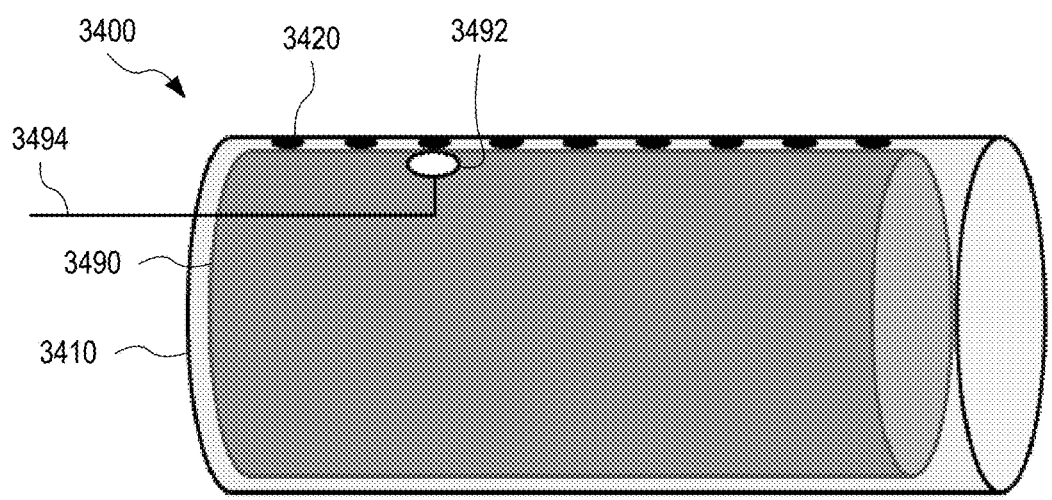
FIG. 34 illustrates a catheter sleeve having at least one sensor on its tubular casing, wherein each sensor is configured to be read out by a catheter inserted into a catheter sleeve and placed in electrical contact with the sensor, according to an embodiment.

FIG. 34 illustrates one catheter sleeve 3400 having one or more sensors 3420 on its tubular casing 3410, wherein each sensor 3420 is configured to be read out by a catheter 3490 inserted into catheter sleeve 3400 and placed in electrical contact with sensor 3420. Each sensor 3420 is configured to sense a property of wall 390 when catheter sleeve 3400 is positioned in body channel 392. Sensor 3420 is an embodiment of sensor 3120. Catheter sleeve 3400 is an embodiment of catheter sleeve 3100 configured for readout of sensor signals from sensor(s) 3420 via catheter 3490 having one or more electrical contacts 3492. Catheter sleeve 3400 is similar to catheter sleeve 3300 and catheter 3490 is similar to catheter 3390, except that each sensor 3420 is read out electrically when brought into physical contact with an electrical contact 3492. Catheter 3490 includes one or more electrical connections 3494 that couples each electrical contact 3492 to electronic readout circuitry outside body channel 392. Electrical contact 3492 may further provide power to sensor 3420.

Figure 35:
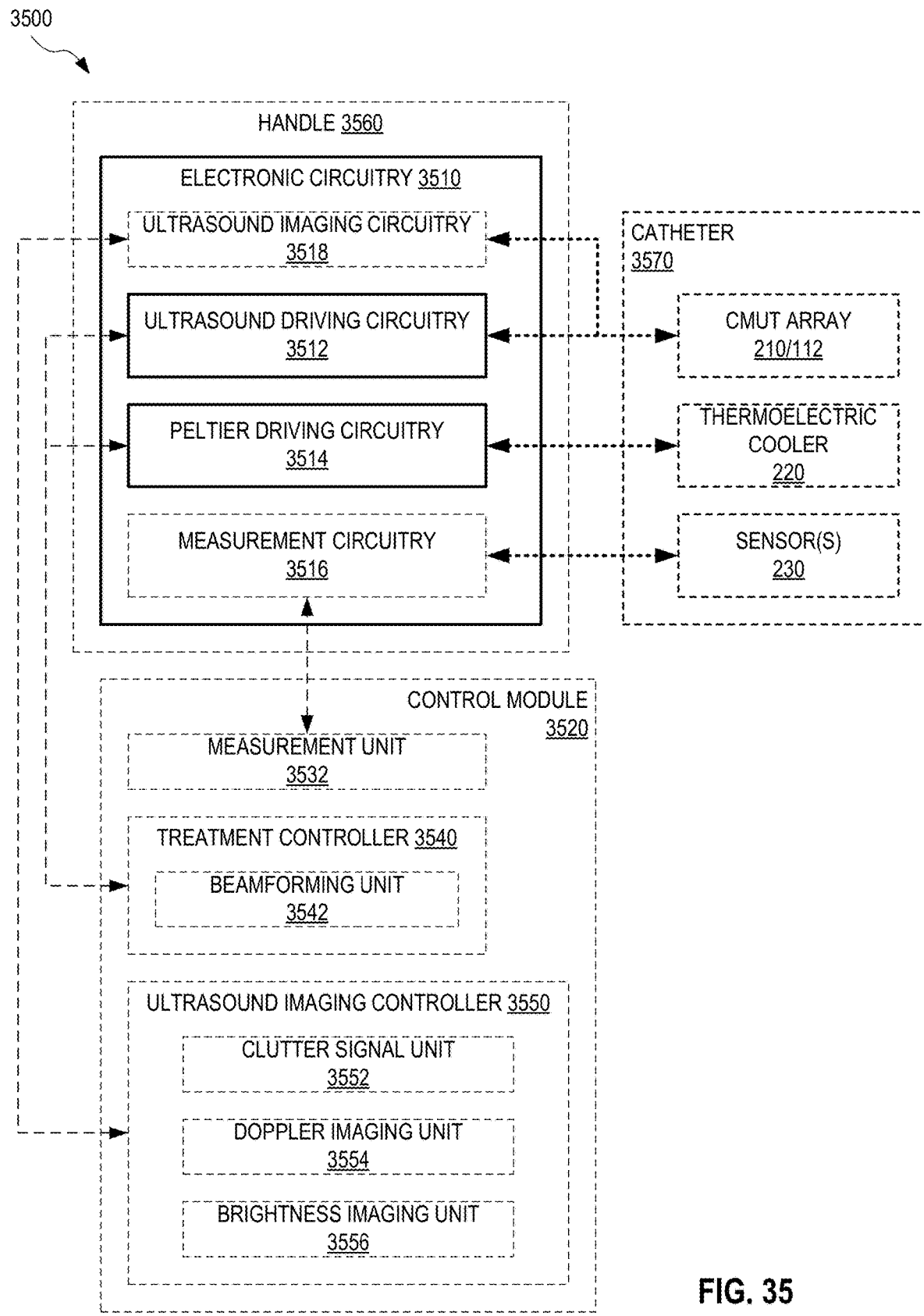
FIG. 35 illustrates a system for ultrasound treatment and solid state cooling, according to an embodiment.

FIG. 35 illustrates one system 3500 for ultrasound treatment with solid state cooling. System 3500 includes electronic circuitry 3510 having ultrasound driving circuitry 3512 and Peltier driving circuitry 3514. Ultrasound driving circuitry 3512 generates drive signals to drive CMUT array 210 or 112, so as to expose target tissue 280 to ultrasound 270. Peltier driving circuitry 3514 powers at least one thermoelectric cooler 220 or 114, to cool non-target tissue 290 heated by ultrasound 270.

System 3500 may include a handle 3560 containing electronic circuitry 3510, wherein handle 3560 is configured to be coupled to a catheter 3570 containing CMUT array 210/112 and thermoelectric cooler(s) 220/114. Handle 3560 and catheter 3570 are embodiments of handle 120 and catheter 110, respectively. Optionally, system 3500 includes both handle 3560 and catheter 3570 and thus forms an embodiment of medical device 100. Without departing from the scope hereof, electronic circuitry 3510 may be implemented externally to handle 3510, for example in or integrated with control module 140 externally to handle 3510.

In an embodiment, system 3500 further includes measurement circuitry 3516 that processes sensor signals from one or more sensors 230 to determine a property of non-target tissue 290 (and/or target tissue 280). The property may be temperature, pressure, or a combination thereof. Alternatively, the property may be a parameter or electrical signal that is related to temperature, pressure, or a combination thereof. Sensor(s) 230 may be implemented in catheter 3570. In an alternate embodiment, measurement circuitry 3516 processes sensor signals from one or more sensors 3120 of catheter sleeve 3100 to determine a property of non-target tissue 290.

In certain embodiments, system 3500 is further configured for ultrasound imaging on target tissue 280. In these embodiments, electronic circuitry 3510 further includes ultrasound imaging circuitry 3518 that (a) generates a plurality of signals to drive CMUT array 210/112 to image target tissue 280 and (b) produces an ultrasound image of target tissue 280 from resulting electrical transducer signals received from CMUT array 210/112.

Electronic circuitry 3510 may be configured to be at least partly controlled by a control module 3520 (an embodiment of control module 140). In one embodiment, system 3500 further includes control module 3520. Handle 3560, catheter 3570, and control module 3520 together form an embodiment of ultrasound treatment system 130. Without departing from the scope hereof, control module 3520 may be a standalone product configured to control electronic circuitry 3510 that is provided by a third party. In one implementation, control module 3520 is a computer system having (a) a processor and (b) non-transitory memory storing machine-readable instructions that, when executed by the processor, commands electronic circuitry 3510 to perform certain steps. Also without departing from the scope hereof, such machine-readable instructions may be a standalone software product configured for implementation on a third party computer system.

In an embodiment, control module 3520 includes a treatment controller 3540 that commands electronic circuitry 3510 to treat target tissue 280 according to a treatment protocol and/or based upon one or both of (a) properties of non-target tissue 280 and/or target tissue 290 determined by measurement circuitry 3516 in cooperation with sensor(s) 230 or sensor(s) 3120 and (b) ultrasound imagery of target tissue 280 generated by ultrasound imaging circuitry 3518 in cooperation with CMUT array 210/112. Treatment controller 3540 may command ultrasound driving circuitry 3512 to drive CMUT array 210/112 to expose target tissue 280 to ultrasound 270. Treatment controller 3540 may command Peltier driving circuitry 3514 to drive thermoelectric cooler(s) 220/114 to cool non-target tissue 290. Alternatively, Peltier driving circuitry 3514 may operate without being directly controlled by treatment controller 3540. For example, Peltier driving circuitry 3514 may be configured to always drive thermoelectric cooler(s) 220/114 when ultrasound driving circuitry 3512 drives CMUT array 210/112 to generate ultrasound 270, and optionally for a set duration thereafter.

Control module 3520 may further include one or both of measurement unit 3532 and ultrasound imaging controller 3550. Measurement unit 3532 cooperates with measurement circuitry 3516 to determine one or more properties (e.g., temperature, pressure, or both) of non-target tissue 290 and/or target tissue 280 based upon sensor signals received from sensor(s) 230 or sensor(s) 3120. Treatment controller 3540 may utilize the determination of such properties in the management of electronic circuitry 3510 and/or peltier driving circuitry 3514.

Ultrasound imaging controller 3550 cooperates with ultrasound imaging circuitry 3518 to generate ultrasound imagery of target tissue 280 using CMUT array 210/112. Ultrasound imaging controller 3550 may command ultrasound imaging circuitry 3518 to generate ultrasound imagery of target tissue 280 according to requests received from treatment controller 3540. Ultrasound imaging controller 3550 may further be configured to process ultrasound images of target tissue 280, for example to inform treatment control performed by treatment controller 3540. Ultrasound imaging controller 3550 may include one, two, or all of a clutter signal unit 3552, a Doppler imaging unit 3554, and a brightness imaging unit 3556. Clutter signal unit 3552 (a) commands ultrasound imaging circuitry 3518 to obtain ultrasound imagery of target tissue 280, which contains a spatially resolved clutter signal, and (b) processes the spatially resolved clutter signal, for example for the purpose of evaluating the instantaneous efficacy of ultrasound treatment of target tissue 280 by CMUT array 210/112. Doppler imaging unit 3554 commands ultrasound imaging circuitry 3518 to obtain Doppler imagery of target tissue 280, for example for the purpose of evaluating the degree of blood perfusion in target tissue 280. Brightness imaging unit 3556 commands ultrasound imaging circuitry 3518 to obtain one or more brightness images of target tissue 280 and/or other tissue near CMUT array 210/112. Such brightness images may be used to evaluate the positioning of CMUT array 210/112 relative to target tissue 280.

In an embodiment, treatment controller 3540 includes a beamforming unit 3542 that commands ultrasound driving circuitry 3512 to beamform ultrasound 270 generated by CMUT array 210/112. Beamforming unit 3542 may command ultrasound driving circuitry 3512 to generate a plurality of drive signals to drive CMUT array 210/112 in a manner that focuses ultrasound 270 on one or more localized regions of target tissue 280. Treatment controller 3540 may utilize data received from ultrasound imaging controller 3550 to determine desired beamforming to be effected by beamforming unit 3542.

Without departing from the scope hereof, some or all of the functionality of control module 3520 may be contained in handle 3560.

Figure 36:
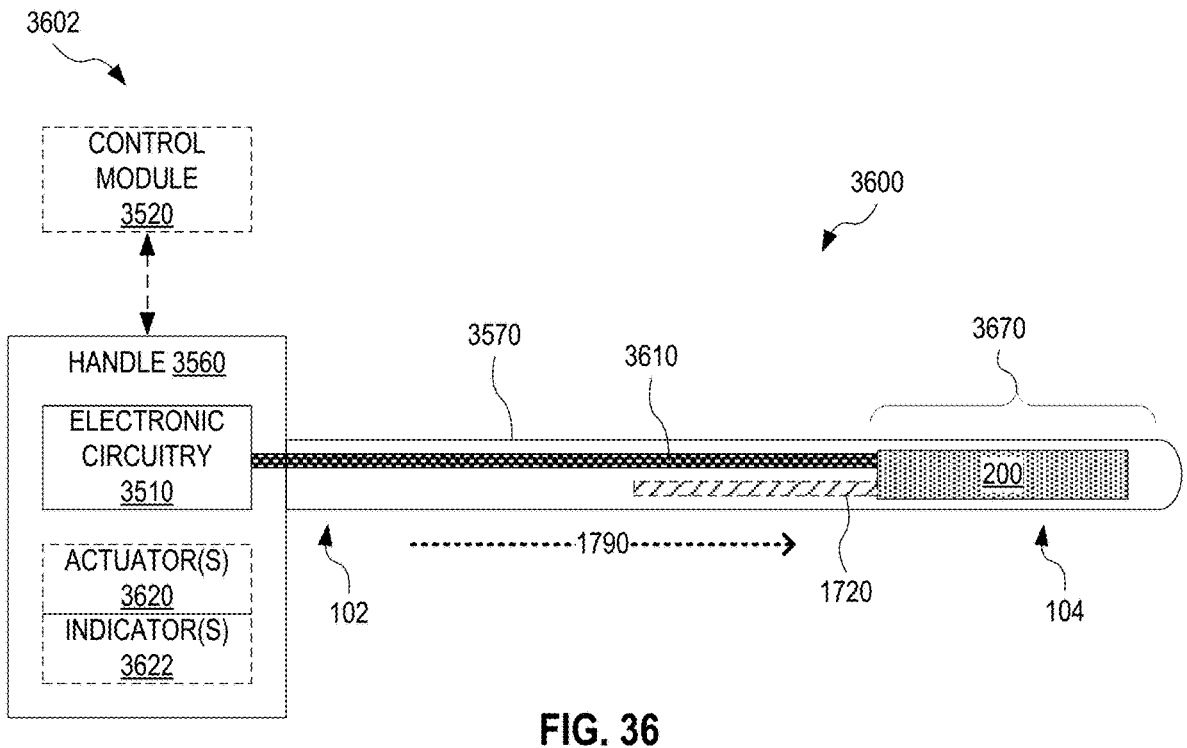
FIG. 36 illustrates a medical device with CMUT array and solid state cooling, according to an embodiment.

FIG. 36 illustrates one medical device 3600 with a CMUT array and solid state cooling. Medical device 3600 includes handle 3560 and catheter 3570. Catheter 3570 implements CMUT-TEC device 200 in a catheter tip 3670 at distal end 104 of catheter 3570. Catheter 3570 includes electrical connections 3610 that communicatively couple CMUT-TEC device 200 and electronic circuitry 3510. Electrical connections 3610 may include one or more flex cables and/or one or more coaxial cables. Optionally, catheter 3570 includes an embodiment of solid thermal conductor 1720 that extends only partway to proximal end 102 of catheter 3570.

In an embodiment, handle 3560 includes one or more actuators 3620 capable of adjusting the position of catheter tip 3670 or a portion thereof. In operation, actuator(s) 3620 may be used to position catheter tip 3670 relative to a reference position. The reference position may be associated with target tissue 280. In one example, handle 3560 includes an actuator 3620 that positions catheter tip 3670 in a desired manner relative to prostate 192. Alternatively, the reference position may be associated with a catheter sleeve (not shown in FIG. 36), such as catheter sleeve 2200. In one implementation, handle 3560 includes an actuator 3620 that is capable of rotating catheter tip 3670 or all of catheter 3570 about longitudinal axis 1790 of catheter 3570. In this implementation, catheter 3570 may include a rotation joint, such as rotation joint 2940. In another implementation, handle 3560 includes an actuator 3620 that is capable of translating catheter tip 3670 or all of catheter 3570 along longitudinal axis 1790. In yet another implementation, handle 3560 includes actuators 3620 cooperatively capable of translating catheter tip 3670 or all of catheter 3570 along longitudinal axis 1790 and also rotating catheter tip 3670 or all of catheter 3570 about longitudinal axis 1790. Embodiments of handle 3560 including one or more actuators 3620 may further include one or more indicators 3622, respectively, that indicate an respective position or orientation of catheter tip 3670.

Medical device 3600 may further include control module 3520 to form an ultrasound treatment system 3602 that is an embodiment of system 3500.

Figure 37:
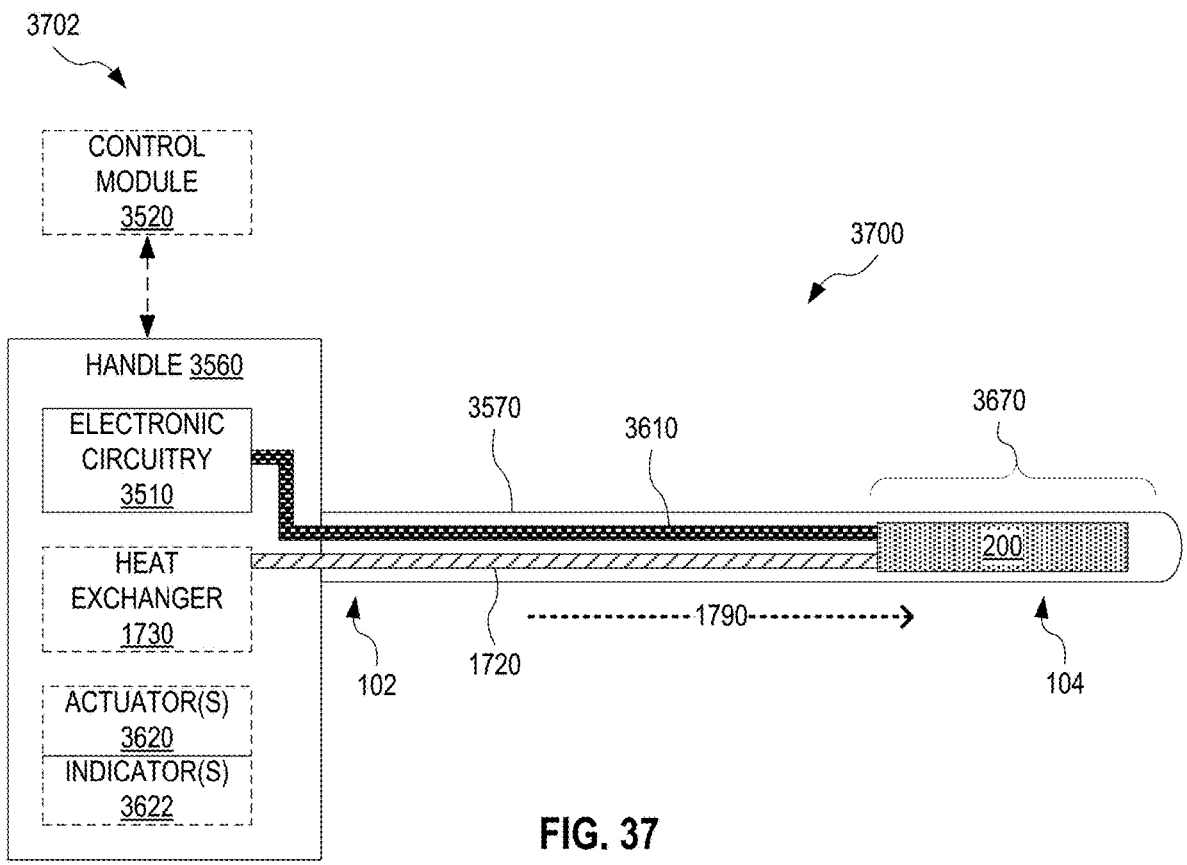
FIG. 37 illustrates a medical device with a CMUT array, solid state cooling, and associated solid state heat removal, according to an embodiment.

FIG. 37 illustrates one medical device 3700 with a CMUT array, solid state cooling, and associated solid state heat removal. Medical device 3700 is an embodiment of medical device 3600, wherein catheter 3570 includes an embodiment of solid thermal heat conductor 1720 extending all the way to proximal end 102 or beyond. In this embodiment, handle 3560 may further include heat exchanger 1730 to cool solid thermal conductor 1720.

Medical device 3700 may further include control module 3520 to form an ultrasound treatment system 3702 that is an embodiment of system 3500.

Figure 38:
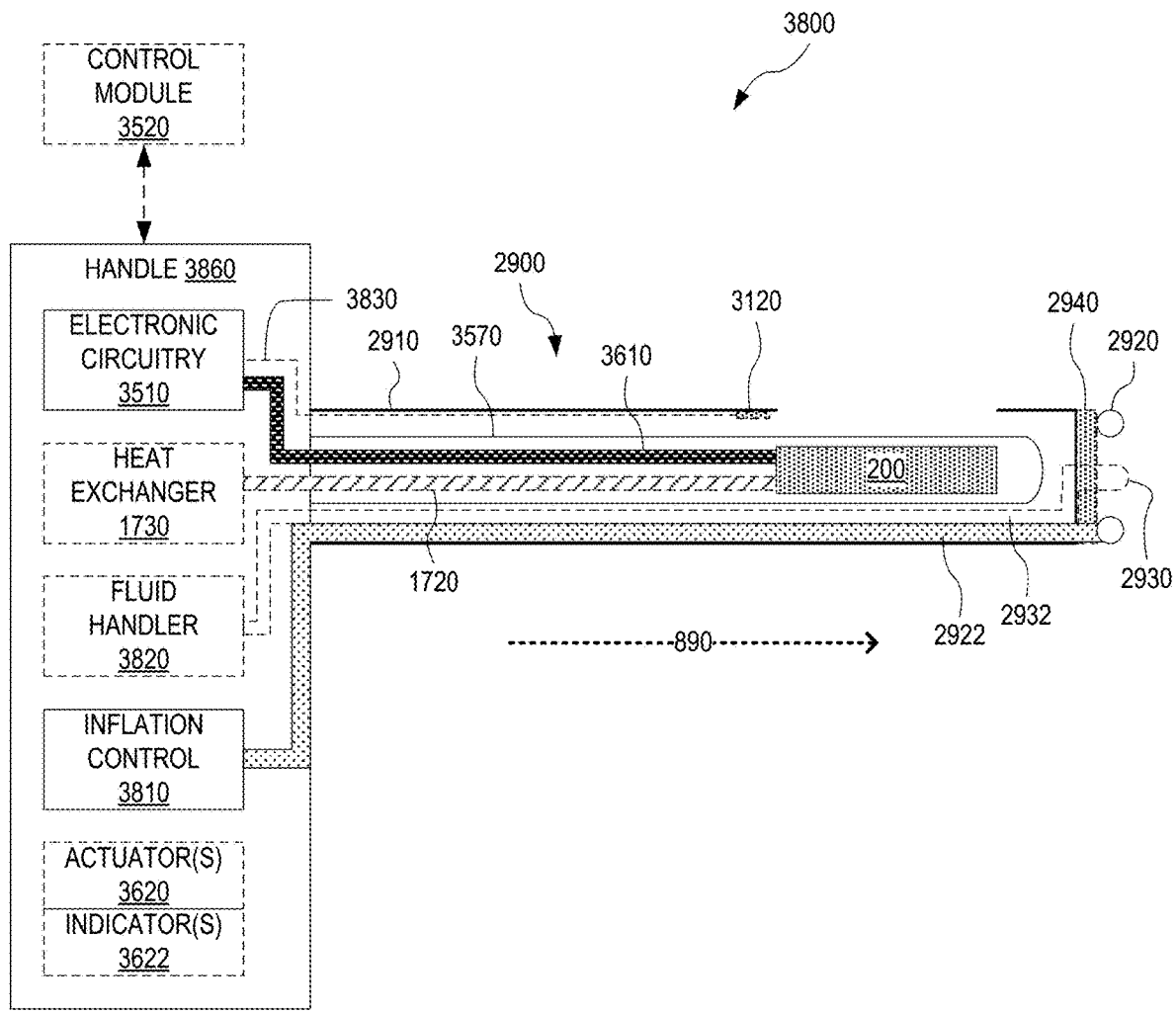
FIG. 38 illustrates a medical system with a CMUT array and solid state cooling, including a catheter sleeve configured to be secured to a body channel, according to an embodiment.

FIG. 38 illustrates one medical system 3800 with a CMUT array and solid state cooling, which further includes catheter sleeve 2900 configured to be secured to body channel 392. In one implementation, medical system 3800 is adapted for ultrasound treatment of prostate 192 from urethra 194, and catheter sleeve 2900 is configured to be secured to bladder 196. Medical system 3800 is an extension of device 3600 or device 3700 that further includes catheter sleeve 2900. In medical system 3800, catheter sleeve 2900 encases catheter 3570. Medical system 3800 includes a handle 3860 which is an embodiment of handle 3560. Handle 3860 includes an inflation control 3810 connected to conduit 2922 and is configured to inflate (or deflate) inflatable balloon 2920 to secure catheter sleeve to body channel 392 (such as to bladder 196). Handle 3860 may further include a fluid handler 3820 that receives and handles fluid passed through conduit 2932 from fluid port 2930.

Optionally, medical system 3800 implements catheter sleeve 2900 with one or more sensors 3120. Medical system 3800 may further include control module 3520 to form an embodiment of system 3500.

Figure 39:
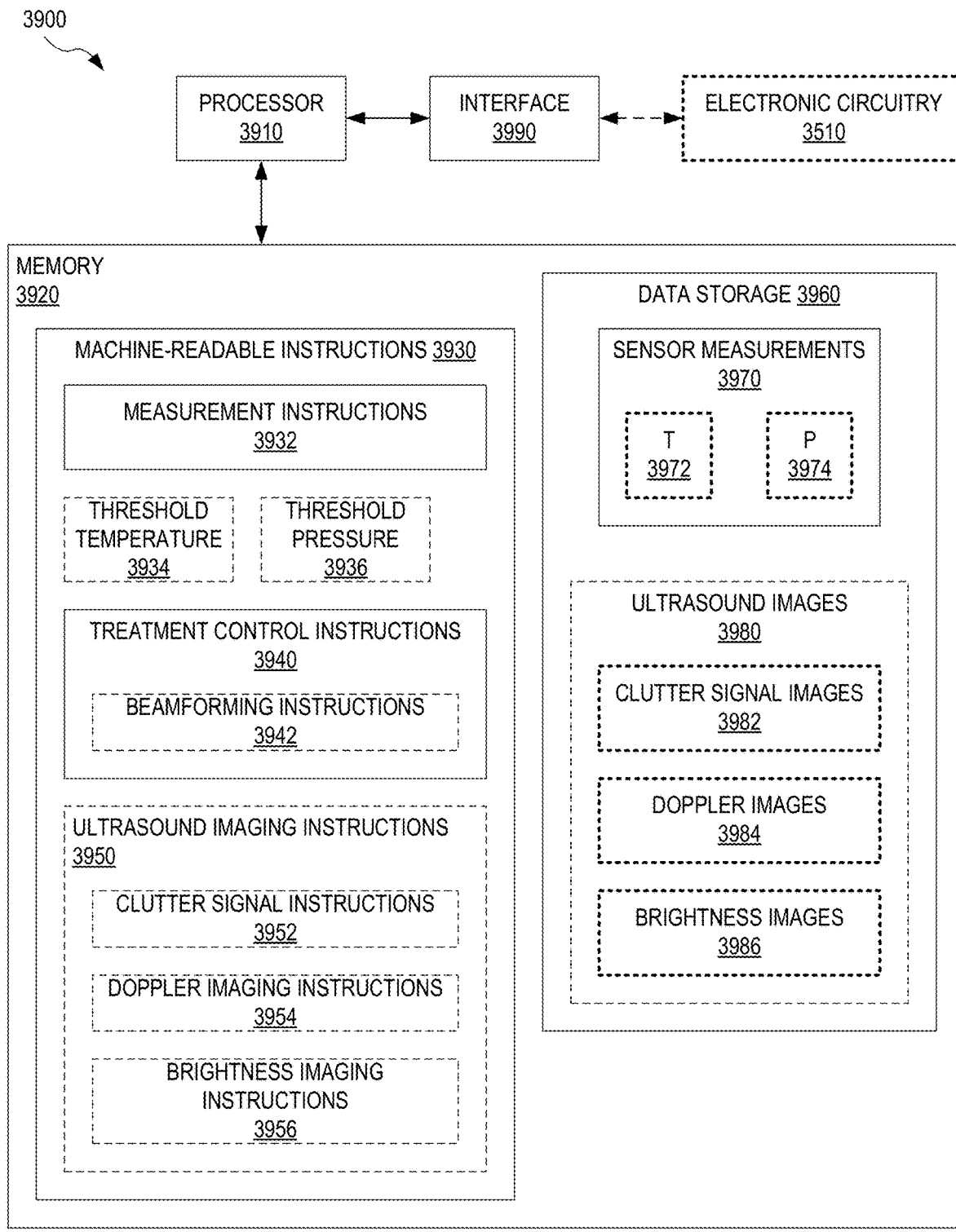
FIG. 39 illustrates a computer for controlling ultrasound treatment, according to an embodiment.

FIG. 39 illustrates one system 3900 for controlling ultrasound treatment. System 3900 includes a processor 3910, a memory 3920 communicatively coupled with processor 3910, and an interface 3990 communicatively coupled with processor 3910 and also configured to communicatively couple system 3900 with electronic circuitry 3510. System 3900 is an embodiment of control module 3520.

Memory 3920 is a non-transitory memory that includes machine-readable instructions 3930 and a data storage 3960 that stores sensor measurements 3970 and, optionally, ultrasound images 3980. Machine-readable instructions 3930 include treatment control instructions 3940 that, upon execution by processor 3910, commands electronic circuitry 3510 to perform ultrasound treatment of target tissue 280. Together, treatment control instructions 3940 and processor 3910 form an embodiment of treatment controller 3540. Treatment control instructions 3940 may include beamforming instructions 3942 that, upon execution by processor 3910, command ultrasound driving circuitry 3512 to beamform ultrasound 270 generated by CMUT array 210/112. Beamforming instructions 3942 cooperate with processor 3910 to form an embodiment of beamforming unit 3542.

Machine-readable instructions 3930 further include measurement instructions 3932 that, upon execution by processor 3910, (a) command measurement circuitry 3516 to obtain one or more tissue property measurements from sensor(s) 230 or sensor(s) 3120, (b) store the tissue property measurements to sensor measurements 3970, and optionally (c) further process the tissue property measurement(s).

Together, measurement instructions 3932 and processor 3910 form an embodiment of measurement unit 3532. Machine-readable instructions 3930 may also include one or both of a threshold temperature 3934 and a threshold pressure 3936. Treatment control instructions 3942, or measurement instructions 3932, may, upon execution by processor 3910, (a) retrieve a measured temperature 3972 or a measured pressure 3974 from sensor measurements 3970, (b) compare measured temperature 3972 or measured pressure 3974 to respective threshold temperature 3934 and a threshold pressure 3936, and (c) adjust ultrasound treatment accordingly.

In an embodiment, machine-readable instructions 3930 further include ultrasound imaging instructions 3950 that, upon execution by processor 3910, command ultrasound imaging circuitry 3518 to obtain ultrasound imagery of target tissue 280 using CMUT array 210/112. Ultrasound imaging instructions 3950 and processor 3910 cooperate to form an embodiment of ultrasound imaging controller 3550. Ultrasound imaging instructions 3950 may include one, two, or all of clutter signal instructions 3952, Doppler imaging instructions 3954, and brightness imaging instructions 3956. Each of clutter signal instructions 3952, Doppler imaging instructions 3954, and brightness imaging instructions 3956 is executable by processor 3910 to perform the functionality of respective clutter signal unit 3552, Doppler imaging unit 3554, and brightness imaging unit 3556. Ultrasound imaging instructions 3950 may be configured to store ultrasound images 3980 to data storage 3960. Clutter signal instructions 3952, Doppler imaging instructions 3954, and brightness imaging instructions 3956 may, upon execution by processor 3910, obtain from and store in data storage 3960, respective clutter signal images 3982, Doppler images 3984, and brightness images 3986.

Without departing from the scope hereof, machine-readable instructions 3930 may be a standalone software product configured for implementation in a third party computer system.

Figure 40:
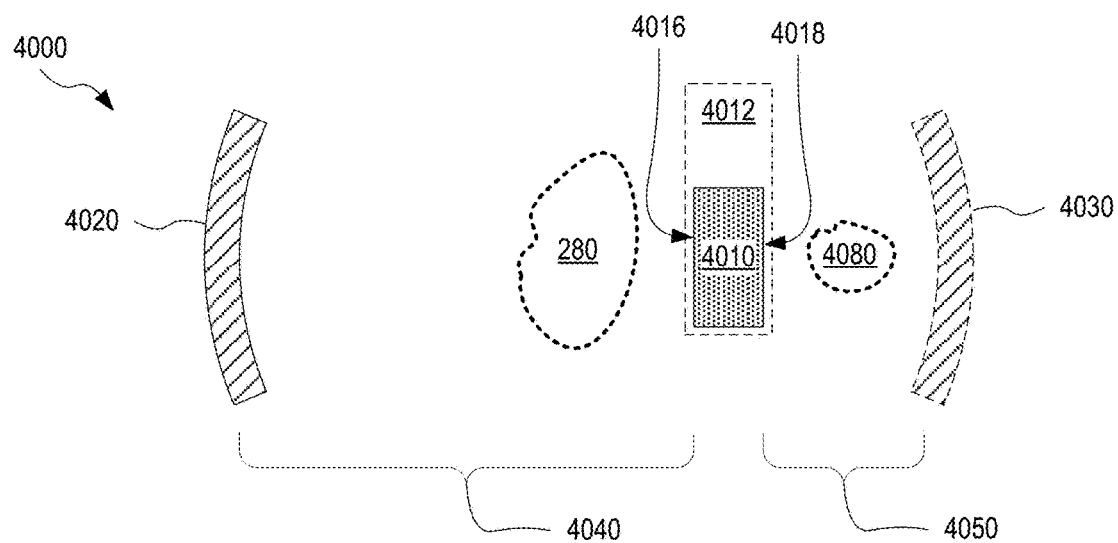
FIG. 40 illustrates a system for enhanced ultrasound treatment, according to an embodiment.

FIG. 40 illustrates a system 4000 for enhanced ultrasound treatment. System 4000 includes an ultrasound transducer array 4010 and an acoustic mirror 4020. In operation, ultrasound transducer array 4010 and acoustic mirror 4020 and are positioned on opposite sides of target tissue 280 to form an acoustic cavity 4040 that contains target tissue 280. Ultrasound generated by ultrasound transducer array 4010 and coupled to acoustic cavity 4040 (in the form of a standing acoustic wave between ultrasound transducer array 4010 and acoustic mirror 4020) is amplified by acoustic cavity 4040. This amplification results in increased ultrasound intensity at target tissue 280, as compared to that achievable in the absence of acoustic cavity 4040. In operation, ultrasound transducer array 4010 may emit ultrasound at a frequency that meets the resonance condition of acoustic cavity 4040 to establish a standing wave. As the properties of tissue within acoustic cavity 4040 change in response to the ultrasound, the resonance condition may change, in which case ultrasound transducer array 4010 may adjust the ultrasound frequency to maintain or reestablish the standing wave.

Ultrasound transducer array 4010 has an ultrasound emission face 4016. Emission face 4016 may be oriented orthogonal to the length axis of acoustic cavity 4040 to efficiently couple ultrasound, emitted by ultrasound transducer 4010, to acoustic cavity 4040. In some use scenarios, it may be necessary or beneficial to orient emission face 4016 away from being orthogonal to the length axis of acoustic cavity 4040. In such scenarios, ultrasound transducer array 4010 may be operated to beamform the ultrasound to be directed in a direction substantially parallel to the length axis of acoustic cavity 4040.

System 4000 may implement CMUT array 112 as ultrasound transducer array 4010. Alternatively, ultrasound transducer array 4010 may be of a different type, such as a piezoelectric transducer array.

In an embodiment, system 4000 includes a catheter 4012 that contains transducer array 4010, to enable placement of transducer array 4010 in body channel 392. In this embodiment, acoustic mirror 4020 may be placed in body channel 392, outside the body, or in a different body channel, depending on the location of target tissue 280. Catheter 4012 may implement CMUT array 112 as ultrasound transducer array 4010, and further implement thermoelectric cooler 114, to form an embodiment of catheter 110.

System 4000 may include one or more additional acoustic mirrors 4030. Each acoustic mirror 4030 may cooperate with ultrasound transducer array 4010 to form a respective acoustic cavity 4050. Each acoustic mirror 4030 allows for treatment of different target tissue portion 4080. In one use scenario, ultrasound transducer array 4010 first couples ultrasound to acoustic cavity 4040 to treat target tissue 280 located within acoustic cavity 4040; ultrasound transducer array 4010 is then reoriented to couple ultrasound to acoustic cavity 4050 to treat target tissue portion 4080 located within acoustic cavity 4050 but outside acoustic cavity 4040.

Certain embodiments of ultrasound transducer 4010 have two opposite facing emission faces 4016 and 4018. In such embodiments, ultrasound transducer device 4010 may be positioned between acoustic mirror 4020 and an acoustic mirror 4030 that faces acoustic mirror 4020. Efficient coupling of the emitted ultrasound to acoustic cavities 4040 and 4050 may then be ensured by orienting emission faces 4016 and 4018 orthogonal to the length axis of acoustic cavities 4040 and 4050 and/or by beamforming the ultrasound emitted by ultrasound transducer array 4010.

Figure 41:
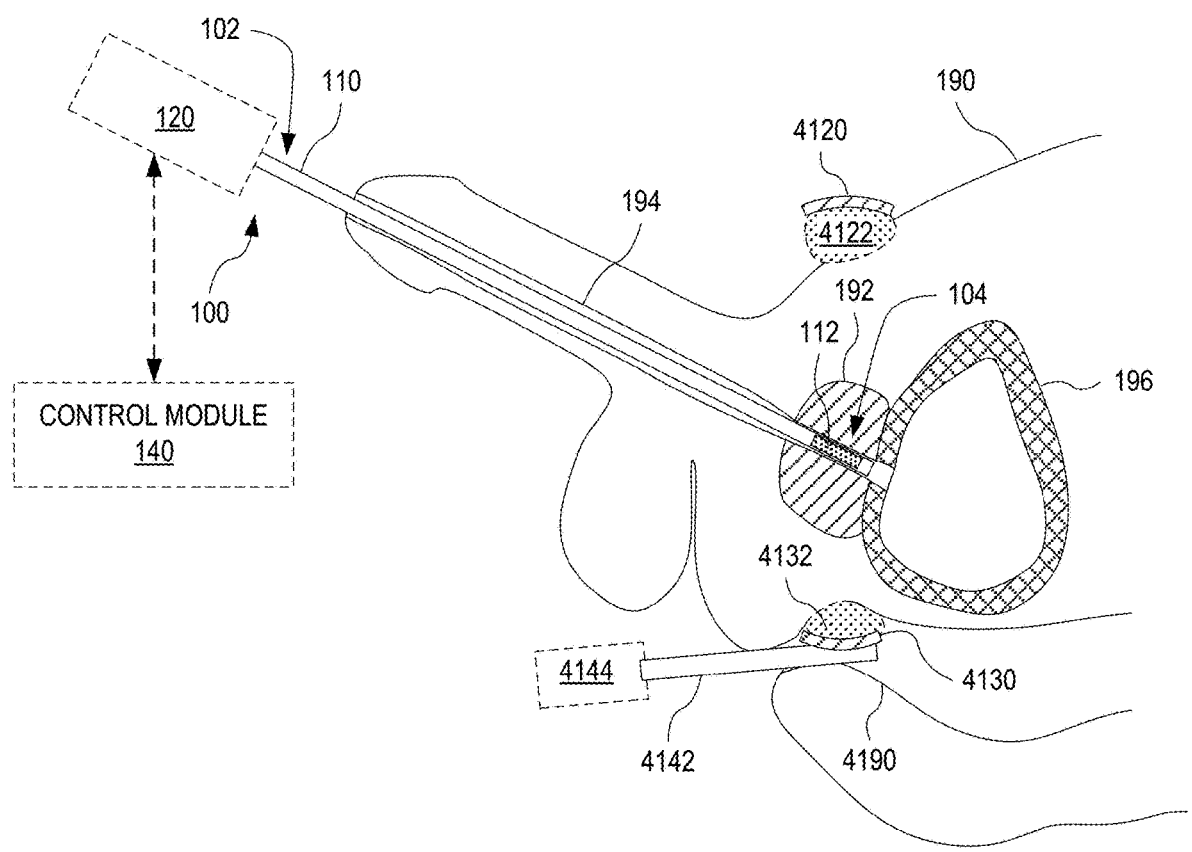
FIG. 41 illustrates a system for enhanced ultrasound treatment of a prostate with solid state cooling of the urethra, according to an embodiment.

FIG. 41 illustrates a system 4100 for enhanced ultrasound treatment of prostate 192 with solid state cooling of urethra 194. System 4100 is an embodiment of system 4000. System 4100 includes (a) catheter 110, adapted for insertion into urethra 194 to position CMUT array 112 at prostate 192, (b) an acoustic mirror 4120 configured to be positioned anterior to prostate 192 outside the body of subject 190, and (c) a rectal catheter 4142 including acoustic mirror 4130 and configured for insertion into rectum 4190 of subject 190 to position acoustic mirror 4130 posteriorly to prostate 192. Ultrasound transducer may thereby form an acoustic cavity with either one of acoustic mirrors 4120 and 4130, thereby forming an acoustic cavity that contains a portion of prostate 192. This acoustic cavity increases the intensity at prostate 192 of ultrasound generated by CMUT array 112.

System 4100 may further include handle 120 and, optionally, control module 140. In addition, rectal catheter 4142 may be equipped with a handle 4144.

In one implementation, acoustic mirror 4120 is coupled with a buffer 4122 that transmits ultrasound between the skin of subject 190 and acoustic mirror 4120. Buffer 4122 is, for example, a fluid-filled bag, a gel-filled bag, or a solid plastic object. Buffer 4122 eliminates, or at least reduces, air gaps between acoustic mirror 4120 and the skin of patient 190, so as to prevent ultrasound emitted by CMUT array 112 from being reflected/scattered by an air-tissue interface at the skin of subject 190. Buffer 4122 may be pushed against the skin of subject 190 to eliminate air gaps. Alternatively, acoustic mirror 4120 may be pushed directly against the skin of subject 190, or with a gel therebetween, to eliminate air gaps between acoustic mirror 4120 and the skin of subject 190 without using buffer 4122. Likewise, acoustic mirror 4130 may be (a) coupled with a buffer 4132 (similar to buffer 4122) or (b) pushed directly against the wall of rectum 4190, optionally with gel between acoustic mirror 4130 and the wall of rectum 4190.

In one example scenario, ultrasound emission from CMUT array 112 is beamformed to be directed along the acoustic cavity formed by ultrasound transducer 4110 and acoustic mirror 4120 or 4130, so as to efficiently couple the ultrasound emission from CMUT array 112 to the acoustic cavity. In another example scenario, CMUT array 112 and acoustic mirror 4120 or 4130 are positioned such that an emission face of CMUT array 112 is orthogonal to the length axis of the acoustic cavity formed by ultrasound transducer 4110 and acoustic mirror 4120 or 4130.

Without departing from the scope hereof, CMUT array 112 of system 4100 may be replaced by another type of ultrasound transducer array, such as a piezoelectric transducer array. In this case, system 4100 may also, instead of catheter 110 having solid state cooling, implement a catheter with liquid cooling. Also without departing from the scope hereof, system 4100 may be provided with only one of acoustic mirrors 4120 and rectal catheter 4142. For example, if the target tissue is exclusively in the anterior portion of prostate 192, rectal catheter 4142 is not needed.

Figure 42:
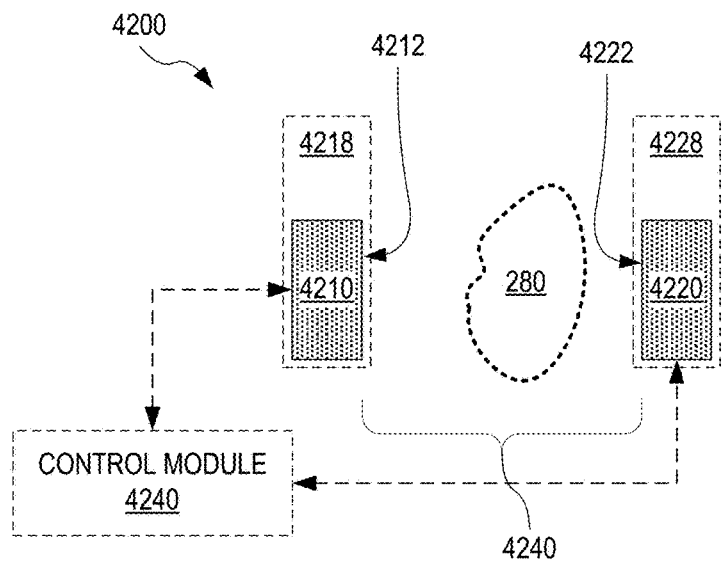
FIG. 42 illustrates another system for enhanced ultrasound treatment, according to an embodiment.

FIG. 42 illustrates another system 4200 for enhanced ultrasound treatment. System 4200 includes two ultrasound transducer arrays 4210 and 4220 having respective ultrasound emission faces 4212 and 4222. In operation, ultrasound transducer arrays 4210 and 4220 are positioned on opposite sides of target tissue 280, with ultrasound emission faces 4212 and 4222 substantially facing each other, to form an acoustic cavity 4240 that contains target tissue 280. Ultrasound that is generated by ultrasound transducer arrays 4210 and 4220 and coupled to acoustic cavity 4240 (in the form of a standing acoustic wave between acoustic mirrors 4020 and 4030) is amplified by acoustic cavity 4240. This amplification results in increased ultrasound intensity at target tissue 280, as compared to that achievable by a single ultrasound transducer array not coupled to or incorporated in an acoustic cavity.

Furthermore, system 4200 enables tuning of the standing wave pattern inside acoustic cavity 4240 to sweep the location of one or more antinodes. In operation, ultrasound transducer arrays 4210 and 4220 may be driven at the same frequency but with an adjustable phase shift relative to each other. The phase shift between ultrasound generated by ultrasound transducer array 4210 and ultrasound generated by ultrasound transducer array 4220 determines the position of antinodes within acoustic cavity 4240. In one use scenario, this phase shift is adjusted to accurately position an antinode at the position of localized target tissue, to deliver a relatively large amount of energy to this localized target tissue. In another use scenario, the phase shift is varied to sweep the position of one or more antinodes across more extended target tissue so as to deliver energy to the target tissue in a more uniform manner than that associated with a fixed standing wave pattern.

System 4200 may implement one or both of ultrasound transducer arrays 4210 and 4220 as CMUT array 112. However, one or both of ultrasound transducer arrays 4210 and 4220 may be of a different type, such as a piezoelectric transducer array.

In an embodiment, system 4200 includes a catheter 4212 that contains transducer array 4210, to enable placement of transducer array 4210 in body channel 392. In this embodiment, ultrasound transducer array 4220 may be placed outside the body or in a different body channel, depending on the location of target tissue 280. Catheter 4212 may implement CMUT array 112 as ultrasound transducer array 4210, and further implement thermoelectric cooler 114, to form an embodiment of catheter 110. In embodiments where ultrasound transducer array 4220 is configured for positioning inside a body channel, system 4200 may include a catheter 4222 that contains transducer array 4210. Catheter 4220 may further include thermoelectric cooler 114.

Either one or both of ultrasound transducer arrays 4210 and 4220 may perform ultrasound imaging, for example to confirm the positioning of the other one of ultrasound transducer arrays 4210 and 4220 relative to target tissue 280, and/or to provide ultrasound images to assess treatment efficacy. Furthermore, ultrasound transducer arrays 4210 and 4220 may cooperate to generate ultrasound transmission images of target tissue 280, wherein one of ultrasound transducer arrays 4210 and 4220 images ultrasound emitted by the other one of ultrasound transducer arrays 4210 and 4220. Such ultrasound images may provide a clutter signal to be used in the assessment of treatment efficacy.

Certain embodiments of system 4200 further include a control module 4240 that controls ultrasound generation, and optionally also ultrasound imaging, by each of ultrasound transducer arrays 4210 and 4220. Control module 4240 may be configured to adjust a phase shift between ultrasound emitted by ultrasound transducer array 4210 and ultrasound transducer array 4220, so as to tune the position of antinode(s) of a standing wave within acoustic cavity 4240. One such embodiment of control module 4240 is capable of sweeping this phase shift to substantially uniformly expose target tissue 280. Control module may include machine-readable instructions, encoded in non-transitory memory, and a processor that executes the machine-readable instructions to adjust or sweep the phase shift.

Figure 43:
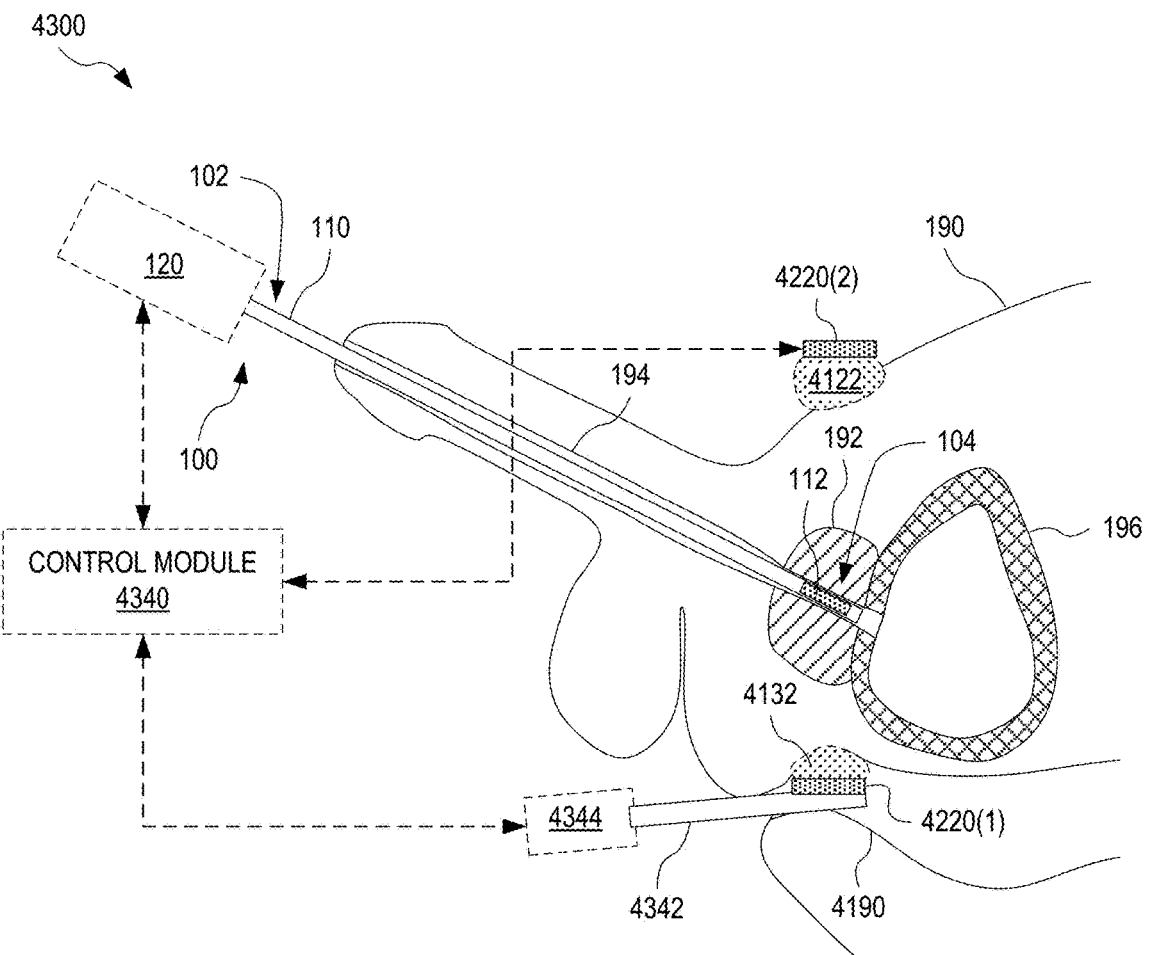
FIG. 43 illustrates another system for enhanced ultrasound treatment of a prostate with solid state cooling of the urethra, according to an embodiment.

FIG. 43 illustrates another system 4300 for enhanced ultrasound treatment of prostate 192 with solid state cooling of urethra 194. System 4300 is an embodiment of system 4200. System 4300 includes (a) catheter 110, adapted for insertion into urethra 194 to position CMUT array 112 at prostate 192, and (b) ultrasound transducer array 4220 configured to cooperate with CMUT 112 to form an embodiment of acoustic cavity 4240 that contains a portion of prostate 192. In system 4300, CMUT array 112 is an embodiment of ultrasound transducer array 4210.

In one embodiment, system 4300 includes a rectal catheter 4342 that includes ultrasound transducer array 4220 (shown as ultrasound transducer array 4220(1) in FIG. 43) and is configured for insertion into rectum 4190 of subject 190 to position ultrasound transducer array 4220 posterior to prostate 192. This embodiment of system 4300 facilitates enhanced ultrasound treatment of the posterior portion of prostate 192. In another embodiment, system 4300 includes an embodiment of ultrasound transducer array 4220 (shown as ultrasound transducer array 4220(2) in FIG. 43) configured to be positioned anterior to prostate 192 outside the body of subject 190. This embodiment of system 4300 facilitates enhanced ultrasound treatment of the anterior portion of prostate 192. In yet another embodiment, system 4300 includes both rectal catheter 4342 and ultrasound transducer array 4220(2), to facilitate sequential or alternating treatment of the anterior and posterior portions of prostate 192. It should be understood that CMUT array 112 may be oriented to face in an anterior direction or a posterior direction, as needed to treat the anterior and posterior portions of prostate 192.

System 4300 may further include handle 120 and, optionally, a control module 4340. In addition, rectal catheter 4342 may be equipped with a handle 4344. Control module 4340 is an embodiment of control module 140 and also an embodiment of control module 4240. Control module 4240 is configured to control ultrasound generation by (a) CMUT array 112 and (b) ultrasound transducer 4220(1) and/or ultrasound transducer array 4220(2). In an embodiment, control module 4340 is capable of adjusting a phase shift between ultrasound generated by CMUT array 112 and ultrasound transducer array 4220(1)/4220(2), in a manner similar to that discussed above in reference to FIG. 42.

In one implementation, ultrasound transducer array 4220(2) is coupled with buffer 4122 to eliminate, or at least reduce, air gaps between ultrasound transducer array 4220(2) and the skin of patient 190, so as to prevent ultrasound emitted by ultrasound transducer array 4220(2) or CMUT array 112 from being reflected/scattered by an air-tissue interface at the skin of subject 190. Alternatively, ultrasound transducer array 4220(2) may be pushed directly against the skin of subject 190, or with a gel therebetween, to eliminate air gaps between ultrasound transducer array 4220(2) and the skin of subject 190 without using buffer 4122. Likewise, ultrasound transducer array 4220(1) may be (a) coupled with a buffer 4132 or (b) pushed directly against the wall of rectum 4190, optionally with gel between ultrasound transducer array 4220(1) and the wall of rectum 4190.

Any one of CMUT array 112, ultrasound transducer 4220(1) and ultrasound transducer array 4220(2) may perform ultrasound imaging, for example to confirm the positioning of another one of CMUT array 112, ultrasound transducer array 4220(1) and ultrasound transducer array 4220(2).

Without departing from the scope hereof, CMUT array 112 of system 4300 may be replaced by another type of ultrasound transducer array, such as a piezoelectric transducer array. In this case, system 4300 may also, instead of catheter 110 having solid state cooling, implement a catheter with liquid cooling.

Figure 44:
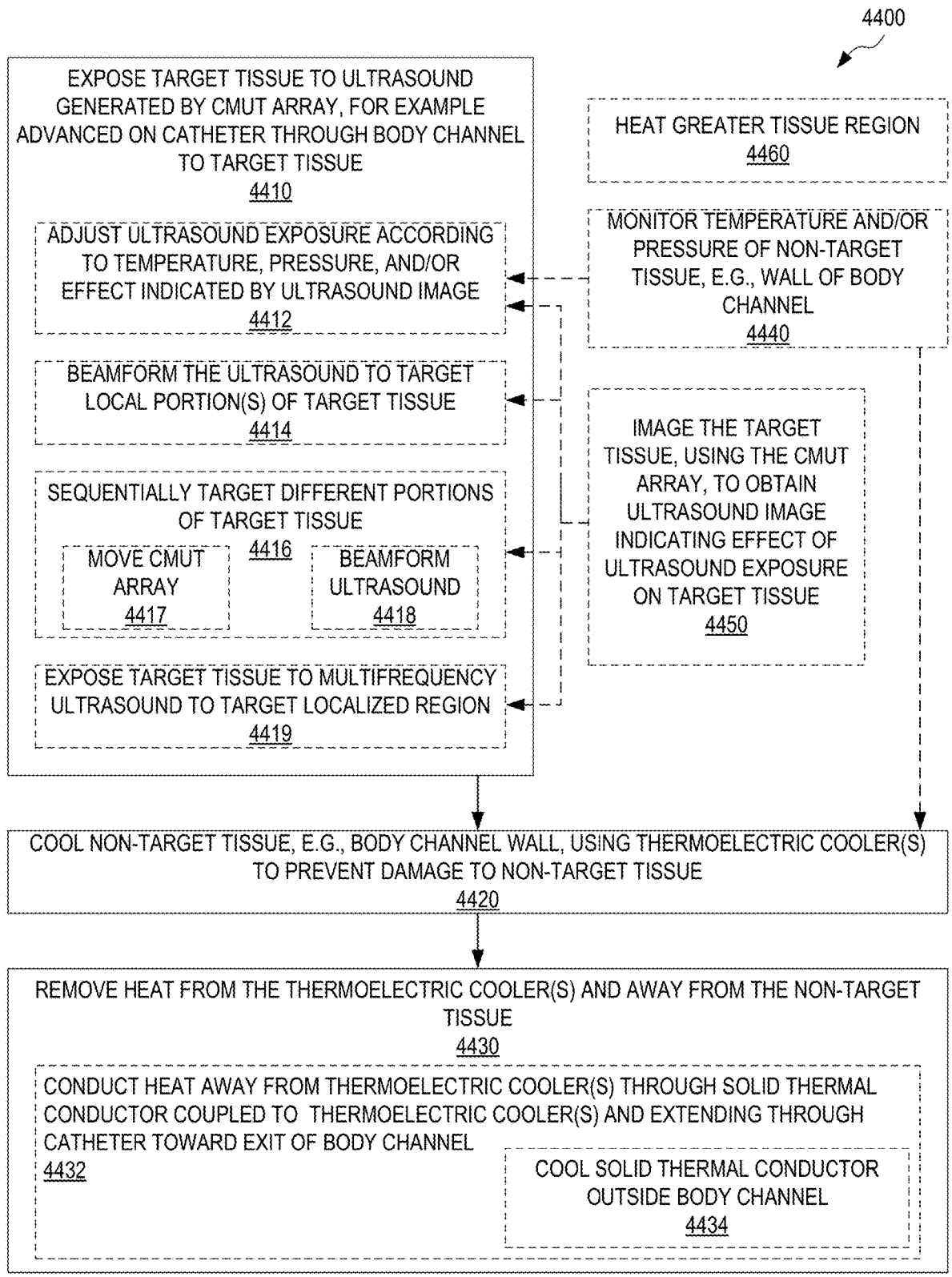
FIG. 44 illustrates a method for ultrasound treatment with solid state cooling, according to an embodiment.

FIG. 44 illustrates one method 4400 for ultrasound treatment with solid state cooling. Method 4400 is performed by catheter 110, for example. The performance of method 4400 may be commanded by treatment controller 3540 utilizing electronic circuitry 3510. Certain embodiments of method 4400 may be encoded in machine-readable instructions 3930 as treatment control instructions 3940. Other embodiments of method 4400 may be encoded in machine-readable instructions 3930 as treatment control instructions 3940 in combination with one or both of measurement instructions 3932 and ultrasound imaging instructions 3950.

Method 4400 includes steps 4410, 4420, and 4430. Step 4410 exposes target tissue, such as target tissue 280, to ultrasound generated by a CMUT array. The CMUT array may be advanced to the target tissue on a catheter through a body channel Step 4420 uses one or more thermoelectric coolers to cool non-target tissue, such as non-target tissue 290, to prevent damage to the non-target tissue. In embodiments where the CMUT array is advanced to the target tissue on a catheter through a body channel, the non-target tissue may be or include at least a portion of the wall of the body channel, and each thermoelectric cooler is coupled to the CMUT array and/or the catheter. Step 4430 removes heat from the thermoelectric cooler(s) and away from the non-target tissue, e.g., the wall of a body channel. In one example of method 4400, CMUT array 210 exposes target tissue 380 to ultrasound 270 from body channel 392 in step 4410, thermoelectric cooler(s) 220 cools wall 390 in step 4420, and solid thermal conductor 710 removes heat from thermoelectric cooler(s) 230 and wall 390 in step 4430. In this example of method 4400, CMUT array 210 and thermoelectric cooler(s) 230 may be advanced to target tissue 380 on catheter 110.

Although shown in FIG. 44 as being sequential, it should be understood that steps 4410, 4420, and 4430 may be performed in parallel.

In an embodiment, step 4430 includes a step 4432 of conducting heat away from the thermoelectric cooler(s) through a solid thermal conductor coupled to the thermoelectric cooler(s). In embodiments where the CMUT array is advanced to the target tissue on a catheter through a body channel, the solid thermal conductor extends through the catheter toward an exit of the body channel. The solid thermal conductor may extend all the way to the exit of the body channel, or extend only partway toward the exit of the body channel. In the case where the solid thermal conductor extends only partway toward the exit of the body channel, the solid thermal conductor may be configured to redistribute (e.g., uniformly) the heat removed from the thermoelectric cooler(s) along a portion of the catheter, while keeping the temperature of the catheter wall, in contact with body tissue, below a threshold value. In one example of step 4430, solid thermal conductor 1720 or 2620 conducts heat away from thermoelectric cooler(s) 220 and 2520, respectively. Step 4432 may include a step 4434 of cooling the solid thermal conductor outside the body channel. In one example of step 4434, heat exchanger 1730 cools solid thermal conductor 1720 outside body channel 392, or a similar heat exchanger cools solid thermal conductor 2620 outside body channel 392.

In certain embodiments, step 4410 includes a step 4412 of adjusting the ultrasound exposure according to a temperature measurement, a pressure measurement, and/or a treatment effect indicated by an ultrasound image. For example, the ultrasound exposure in step 4410 may be at least temporarily stopped if the temperature of wall 390 exceeds a threshold temperature, if the pressure of wall 390 exceeds a threshold pressure; the ultrasound exposure in step 4410 may be stopped or reduced if the temperature or pressure of wall 390 indicates that target tissue 380 is at or near a target temperature; or the ultrasound exposure in step 4410 may be adjusted according to an evaluation of temperature, elasticity, echogenicity, necrosis, or treatment efficacy in target tissue 380 based upon ultrasound imagery of target tissue 380. In one use scenario associated with ultrasound treatment of prostate 192 from urethra 194, the threshold temperature is in the range between 41 and 45 degrees C., such as 42 degrees C., to prevent damage to urethra 194. Heating of target tissue 380, and potentially also wall 390, may cause swelling of the tissue. Implementation of a threshold pressure in step 4412 may help keep the degree of swelling in an acceptable range.

In one such embodiment, method 4400 further includes a step 4440 of monitoring temperature and/or pressure of the non-target tissue, e.g., the wall of a body channel. In one example of this embodiment, sensor(s) 230 or sensor(s) 3120 monitor the temperature and/or pressure of wall 390 in step 4440, and the ultrasound exposure by CMUT array 210 is adjusted according to this temperature and/or pressure in step 4412. Method 4400 may perform steps 4440 in parallel with step 4410.

In another such embodiment, method 4400 further includes a step 4450 of using the CMUT array to image the target tissue to obtain an ultrasound image that indicates an effect of the ultrasound treatment on the target tissue. In one example of this embodiment, CMUT array 210 images target tissue 380, and the ultrasound exposure by CMUT array 210 is adjusted, in step 4412, according to a treatment effect indicated by the ultrasound image obtained from CMUT array 210. Method 4400 may perform steps 4410 and 4450 simultaneously or alternate between steps 4410 and 4450.

Method 4400 may utilize step 4440 to guide the performance of step 4420. In one such example, cooling of non-target tissue 290 by thermoelectric cooler(s) 220, in step 4420, is adjusted according to measurements performed by sensor(s) 230 in step 4440. Without departing from the scope hereof, step 4420 may include running the thermoelectric cooler(s) in reverse to heat the non-target tissue, for example to prevent or compensate for over-cooling.

Step 4410 may include a step 4414 of beamforming the ultrasound to target localized tissue or target one or more local portions of the target tissue. In one example of step 4414, the drive signals for different transducers of CMUT array 210 are phase shifted relative to each other to beamform ultrasound 270, for example as discussed above in reference to FIG. 8-10. Step 4410 may perform the beamforming in step 4414 according to a treatment effect indicated by an ultrasound image obtained in step 4450. For example, if an ultrasound image obtained in step 4450 indicates that a particular portion of target tissue 380 is in need of more ultrasound exposure, step 4414 may beamform ultrasound 270 to target this particular portion of target tissue 380.

In an embodiment, step 4410 includes a step 4416 of sequentially targeting different portions of the target tissue. Step 4416 may systematically scan across the target tissue according to a predefined scan pattern, or step 4416 may sequentially target different portions of the target tissue according to a treatment effect indicated by an ultrasound image obtained in step 4450. Step 4416 may include one or both of steps 4417 and 4418. Step 4417 moves the CMUT array to a different position. In one example of step 4417 actuator 3620 translates CMUT array along the length of body channel 392 to sequentially direct ultrasound 270 to different portions of target tissue 380. In another example of step 4417, actuator 3620 rotates CMUT array to sequentially direct ultrasound 270 to different portions of target tissue 380 located on different sides of body channel 392. Step 4418 beamforms the ultrasound to sequentially target different portions of target tissue 380. Step 4416 may perform steps 4417 and 4418 in conjunction. Additionally, step 4416 may, optionally in conjunction with steps 4417 and/or 4418, sequentially activate different CMUT cells or CMUT elements of the CMUT array to sequentially target different portions of target tissue 380.

Furthermore, step 4410 may include a step 4419 of exposing the target tissue to multifrequency ultrasound to target localized regions. Multifrequency ultrasound has the capability of very accurately focusing ultrasound to a localized region, and step 4419 may therefore be particularly useful in scenarios where the target tissue is a cancerous tumor and it is particularly important to induce necrosis in all the cancerous tissue without damaging significant amounts of neighboring healthy tissue. In one example of step 4410, different transducers of CMUT array 210 are driven at different frequencies.

Optionally, method 4400 includes a step 4460 of heating a greater tissue region, containing the target tissue, to a temperature that is below a target temperature for the target tissue in step 4410. Inclusion of step 4460 in method 4400 may reduce the amount of ultrasound energy that must be delivered to the target tissue in step 4410 to reach the target temperature of the target tissue. Step 4460 may thus shorten the duration of step 4410 and, in some scenarios, reduce the risk of heat-induced damage to non-target tissue. In one example of step 4460, an external heat source is positioned on the skin of a subject near the target tissue. The external heat source may advantageously be positioned to heat the greater tissue region from a direction that is significantly different from the direction of ultrasound exposure in step 4410, to avoid the external heat source delivering a relatively large amount of heat to locations close to the CMUT array of step 4410. In a scenario where the target tissue is in prostate 192, an external heater may be positioned on the skin of subject 190 anterior to prostate 192, so as to heat the greater tissue region from a direction that is substantially opposite to the direction of ultrasound exposure in step 4410. In another example of step 4460, the body temperature of the subject is raised using medicine. In yet another example, step 4460 applies the CMUT array of step 4410 in a less targeted fashion to raise the temperature of a larger region around and including the target tissue. In one embodiment, step 4460 is performed prior to step 4410, to raise the temperature of the greater tissue region prior to method 4400 commencing step 4410. In another embodiment, step 4460 delivers heat to the greater tissue region during at least some of the ultrasound treatment of step 4410.

Figure 45:
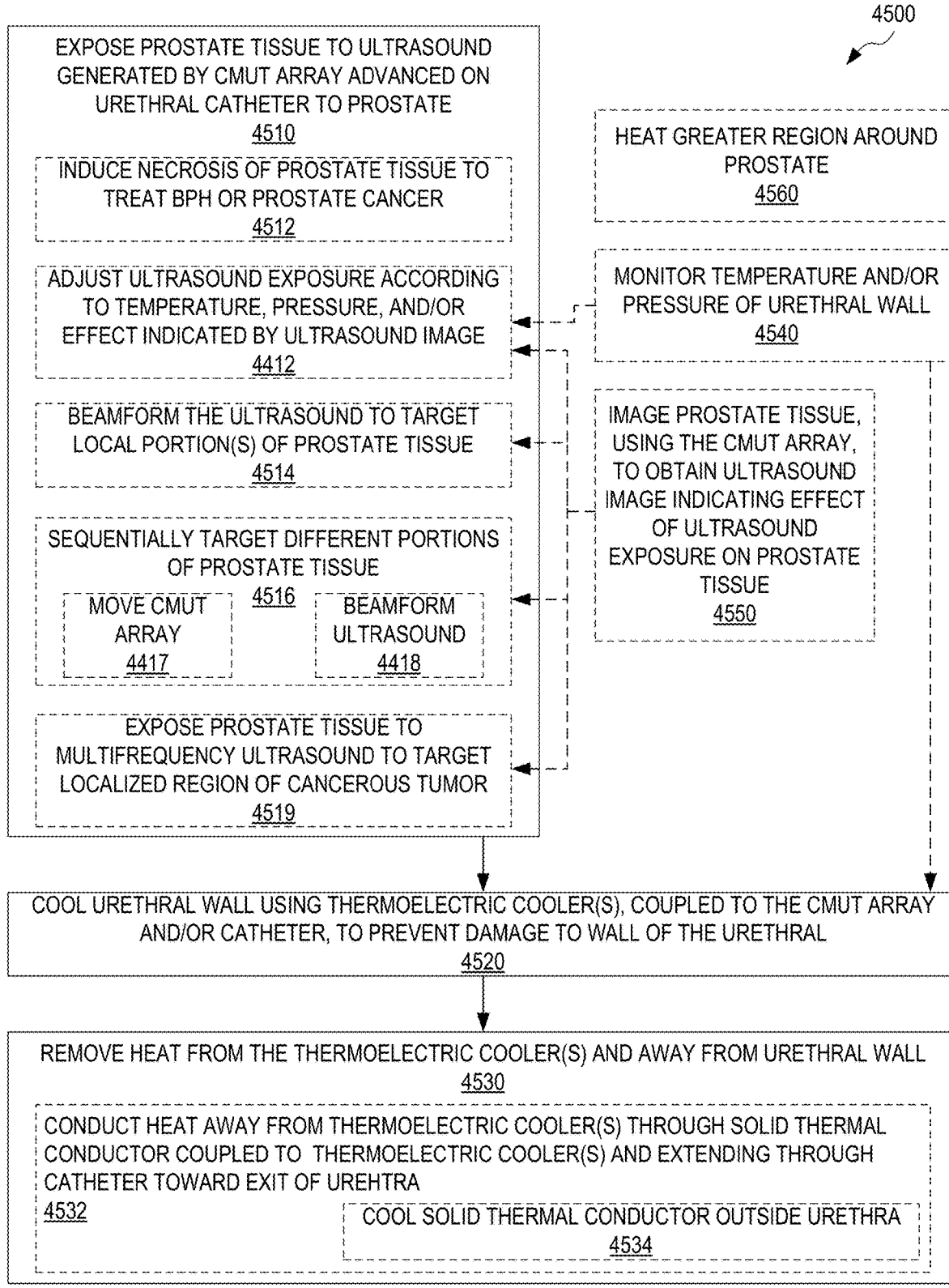
FIG. 45 illustrates a method for ultrasound treatment of a prostate with solid state cooling of the urethra, according to an embodiment.

FIG. 45 illustrates one method 4500 for ultrasound treatment of prostate 192 with solid state cooling of the urethra 194. Method 4400 is performed by catheter 110, for example. Method 4500 is an embodiment of method 4400 specifically adapted for ultrasound treatment of prostate 192, for example to treat BPH or prostate cancer.

Method 4500 includes steps 4510, 4520, and 4530, which are embodiments of steps 4410, 4420, and 4430, respectively. Step 4510 exposes prostate 192 to ultrasound generated by a CMUT array that is advanced to the prostate 192 on a catheter through urethra 194. Step 4520 uses one or more thermoelectric coolers to cool the wall of urethra 194 to prevent heat-induced damage to urethra 194 (and, optionally, heat the wall of urethra 194 to prevent or compensate for over-cooling of urethra 194). Each thermoelectric cooler is coupled to the CMUT array and/or the catheter. Step 4530 removes heat from the thermoelectric cooler(s) and away from the wall of urethra 194.

Method 4500 may further include steps 4540, 4550, and/or 4560. Step 4540 is an embodiment of step 4440 that monitors the temperature, pressure, or both temperature and pressure of the wall of urethra 194. Step 4550 is an embodiment of step 4450 that obtains an ultrasound image of prostate 192. Step 4560 is an embodiment of step 4460 that heats a greater tissue region around prostate 192.

Step 4510 may include steps 4512, 4412, 4514, 4516, and 4519. Step 4512 induces necrosis of tissue or prostate 192 to treat BPH or prostate cancer. Step 4514 is an embodiment of step 4414 that uses beamforming to target localized regions within prostate 192. Step 4516 is an embodiment of step 4416 that sequentially targets different portions of prostate 192. Step 4516 may include one or both of steps 4417 and 4418. Step 4510 is an embodiment of step 4419 that exposes tissue of prostate 192 to multifrequency ultrasound to target a localized region of a cancerous tumor.

Step 4530 may include step 4532. Step 4532 is an embodiment of step 4434 that conducts heat away from the thermoelectric cooler(s) through a solid thermal conductor coupled to the thermoelectric cooler(s) and extending through a urethral catheter toward the exit of urethra 194. Step 4532 may include step 4534. Step 4534 is an embodiment of step 4434 that cools the solid thermal conductor outside urethra 194.

Figure 46:
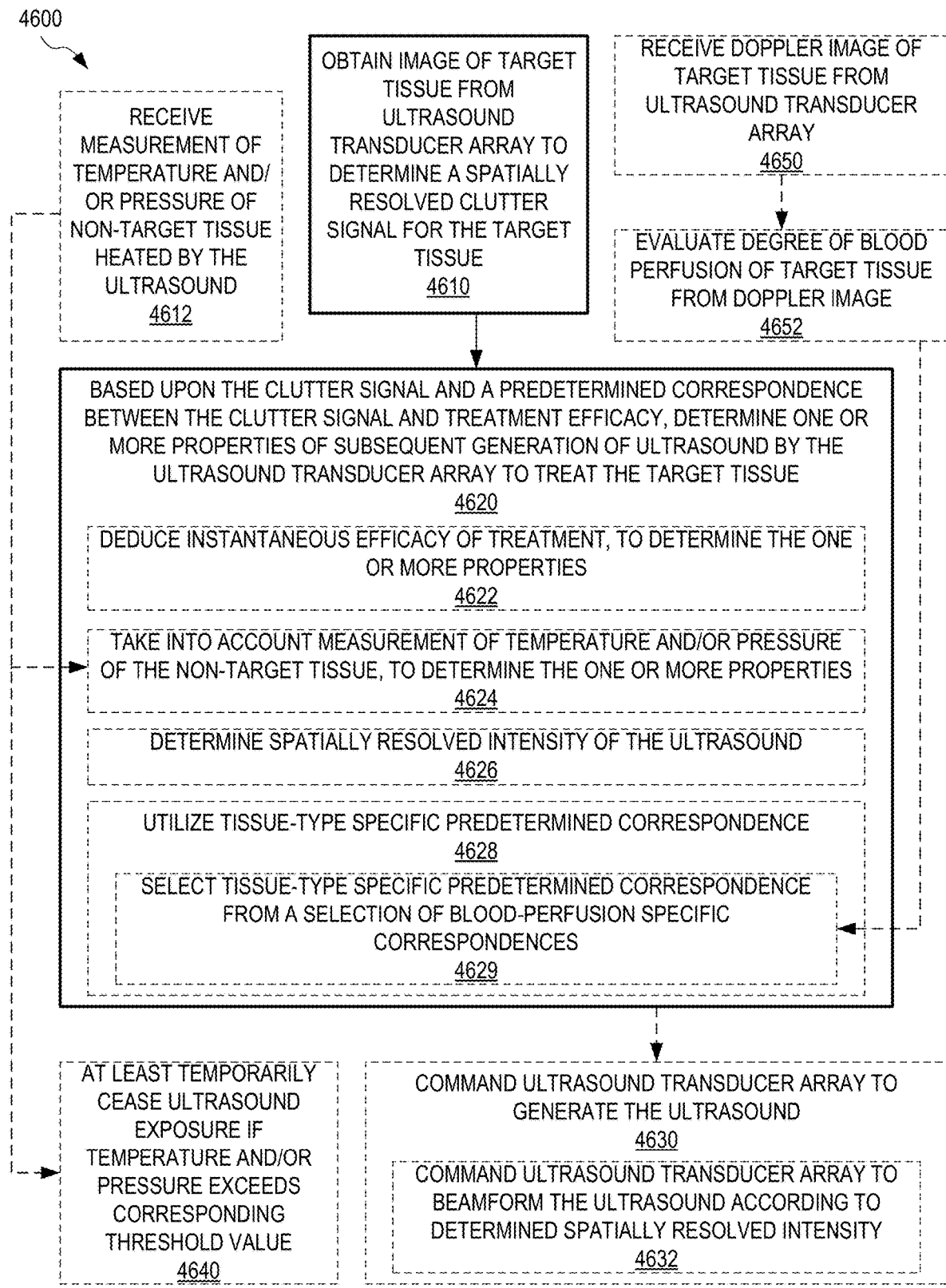
FIG. 46 illustrates a method for ultrasound treatment with ultrasound imaging feedback, according to an embodiment.

FIG. 46 illustrates one method 4600 for ultrasound treatment with ultrasound imaging feedback. Method 4600 may be performed by treatment controller 3540. Method 4600 may be encoded in machine-readable instructions 3930 as at least a portion of treatment control instructions 3940. Each of methods 4400 and 4500 may implement method 4600 in step 4412. The feedback used in method 4600 utilizes a predetermined correspondence between an ultrasound clutter signal for the target tissue and an ultrasound treatment efficacy. Thus, method 4600 uses ultrasound images, recorded by the same ultrasound device used for actual treatment, to guide subsequent ultrasound treatment. Advantageously, method 4600 does not require magnetic resonance imaging to monitor treatment progress.

The predetermined correspondence between the clutter signal and the treatment efficacy may be obtained from clinical trials preceding the performance of method 4600. In these trials, a patient cohort is subjected to ultrasound treatment of target tissue, e.g., prostate tissue. Ultrasound imaging is performed, at least at the end of the ultrasound treatment of each patient, to obtain spatially resolved clutter signals for the target tissue. In one implementation, the trials ultrasound treatment utilizes alternating ultrasound imaging and ultrasound treatment. In the trials, the treatment efficacy is determined using conventional methods, such as through biopsy or magnetic resonance imaging. The treatment efficacy may be determined at a later point in time after all tissue changes induced by the ultrasound treatment have taken place. Each of the degree of necrosis of the tissue and the degree to which cancerous tissue has been destroyed may serve as a parameter indicative of treatment efficacy. The treatment efficacy may be determined in a spatially resolved fashion. A comparison of clutter signals and the treatment efficacy results in a correspondence between clutter signal and treatment efficacy. This correspondence may depend on the type of tissue being treated. For example, the correspondence associated with prostate tissue may be different from the correspondence associated with breast tissue. In addition, the correspondence may depend on the degree of blood perfusion in the target tissue. Thus, in certain implementations, the predetermined correspondence applied in step 4620 may be specific to the tissue type and, optionally, the degree of blood perfusion.

Method 4600 includes steps 4610 and 4620. Step 4610 obtains an ultrasound image of target tissue from an ultrasound transducer array to determine a spatially resolved clutter signal for the target tissue, that is, a clutter signal as a function of position within the target tissue. Step 4620 determines, based upon a predetermined correspondence between the clutter signal and a treatment efficacy, one or more properties of subsequent generation of ultrasound by the ultrasound transducer array to treat the target tissue. In one example of step 4610, treatment controller 3540 receives an ultrasound image of target tissue (e.g., prostate tissue) that includes a spatially resolved clutter signal or may be processed by treatment controller 3540 to determine a spatially resolved clutter signal for the target tissue. In one example of step 4620, treatment controller 3540 uses a predetermined correspondence between the clutter signal and a treatment efficacy to determine one or more properties of subsequent generation of ultrasound, by the same ultrasound transducer array used to record the ultrasound image in step 4610, to treat the target tissue. The ultrasound transducer array may be CMUT array 112. However, without departing from the scope hereof, the ultrasound transducer array may be a different type of transducer array, such as a piezoelectric ultrasound transducer array.

Method 4600 may be performed several times during an ultrasound treatment procedure. In one implementation, method 4600 provided real-time feedback.

Step 4620 may include a step 4622 of deducing the instantaneous efficacy of ultrasound treatment, based upon an instantaneous clutter signal and the predetermined correspondence between clutter signal and treatment efficacy.

In certain embodiments, step 4620 includes a step 4626 of determining a spatially resolved intensity of ultrasound to be generated in a subsequent stage of ultrasound treatment by the ultrasound transducer array. In one example, step 4626 applies the predetermined correspondence between clutter signal and treatment efficacy to the spatially resolved clutter signal obtained in step 4610 to identify which local regions need more ultrasound exposure than others.

Step 4620 may include a step 4628 of utilizing a tissue-type specific correspondence between clutter signal and treatment efficacy. In one example, the target tissue is prostate tissue and step 4628 utilizes a prostate-specific correspondence between clutter signal and treatment efficacy. In one embodiment, step 4628 includes a step 4629 and method 4600 further includes steps 4650 and 4652. Step 4629 selects the tissue-type specific correspondence between clutter signal and treatment efficacy from a selection of blood-perfusion specific correspondences. Step 4629 is preceded by steps 4650 and 4652. Step 4650 receives a Doppler image of the target tissue obtained using the ultrasound transducer array. Step 4652 processes the Doppler image to evaluate the degree of blood perfusion in the target tissue, and step 4629 selects a blood-perfusion specific correspondence that most closely relates to the degree of blood-perfusion in the target tissue.

In an embodiment, step 4620 includes a step 4624 and method 4600 further includes a step 4612. Step 4612 receives a measurement of temperature and/or pressure of non-target tissue heated by the ultrasound, for example obtained using sensor(s) 230 or sensor(s) 3120. Step 4624 further takes into account the measured temperature and/or pressure of the non-target tissue to determine the one or more properties of subsequent ultrasound exposure. In this embodiment, method 4600 may further include a step 4640 of at least temporarily ceasing ultrasound exposure if either temperature or pressure exceeds a corresponding threshold value.

Optionally, method 4600 further includes a step 4630 of commanding the ultrasound transducer array to generate the ultrasound with the one or more properties determined in step 4620. In one example of step 4630, treatment controller 3540 commands ultrasound driving circuitry 3512 to drive CMUT array 112/210 in a manner that generates ultrasound having the one or more properties determined in step 4620. In embodiments of method 4600 including both step 4626 and 4630, step 4630 may include a step 4632 of commanding the ultrasound transducer array to beamform the ultrasound with the spatially resolved intensity determined in step 4626. Step 4632 may be performed by beamforming unit 3542.

Without departing from the scope hereof, the predetermined correspondence between treatment efficacy and clutter signal may be replaced by a similarly predetermined correspondence between treatment efficacy and Doppler signal. For example, a reduced Doppler signal may be associated with reduced vascularization, which in turn may indicate complete treatment. Also without departing from the scope hereof, the predetermined correspondence between treatment efficacy and clutter signal may be replaced by a predetermined correspondence between treatment efficacy and a combination of clutter signal and Doppler signal. Furthermore, the predetermined correspondence between (a) treatment efficacy and (b) clutter signal and/or Doppler signal may be used in conjunction with predetermined correlation between treatment efficacy and other measurable parameters such as one or more of temperature at the body channel wall, pressure at the body channel wall, frequency of the ultrasound emission, and thermal dose delivered by the CMUT array (optionally corrected for known energy losses). Clinical trials may consider and evaluate such parameters together with evaluation of treatment efficacy, for use in method 4600.

Figure 47:
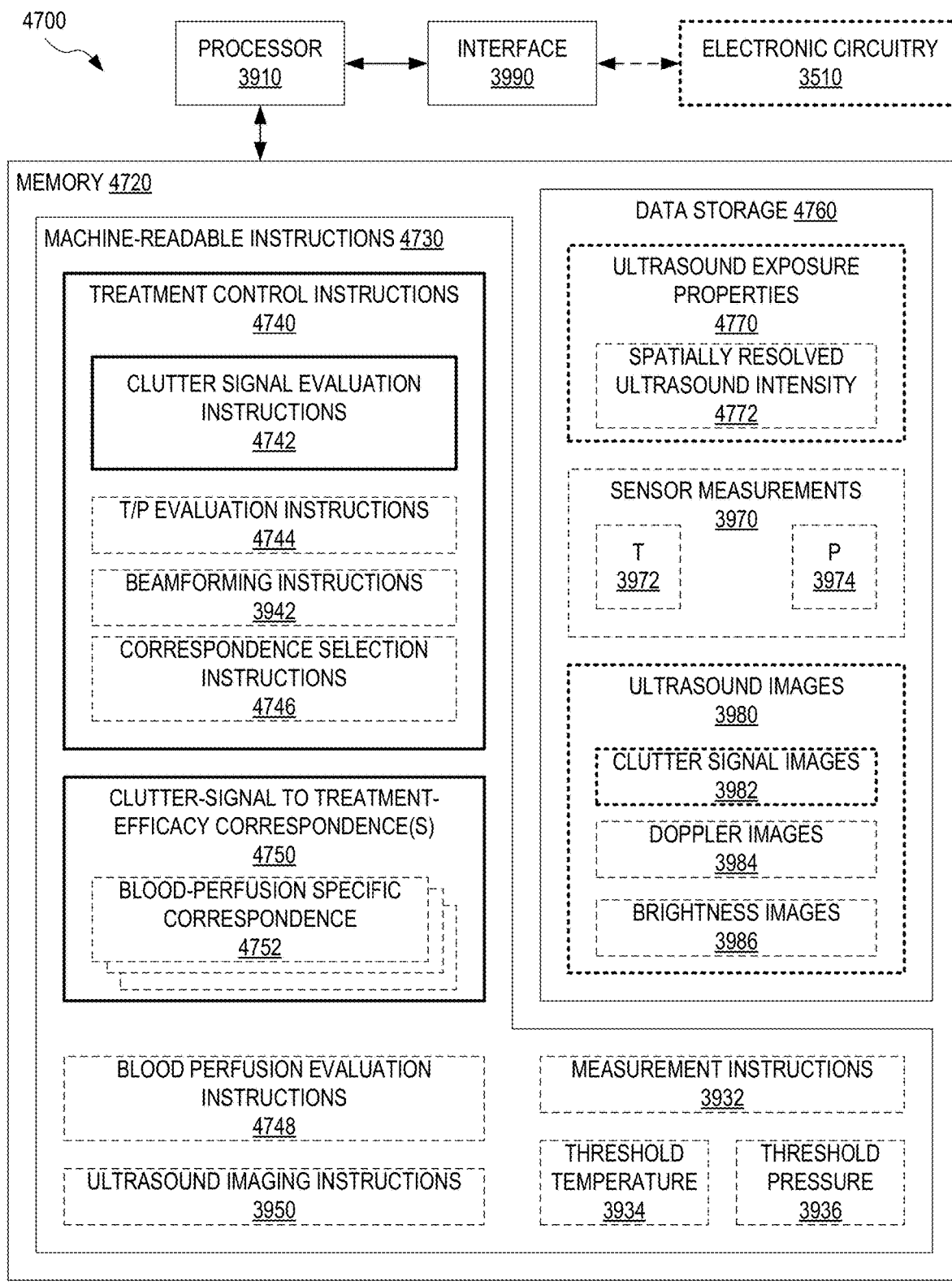
FIG. 47 illustrates a system for controlling ultrasound treatment with ultrasound imaging feedback, according to an embodiment.

FIG. 47 illustrates one system 4700 for controlling ultrasound treatment with ultrasound imaging feedback. System 4700 is similar to system 3900 but specifically adapted for ultrasound imaging feedback based on clutter signals. System 4700 includes processor 3910, a memory 4720 communicatively coupled with processor 3910, and interface 3990 communicatively coupled with processor 3910 and also configured to communicatively couple computer 4700 with electronic circuitry 3510. System 4700 is an embodiment of control module 3520 that is configured to perform method 4600.

Memory 4720 is a non-transitory memory that includes machine-readable instructions 4730 and a data storage 4760 that stores ultrasound images 3980 including clutter signal images 3982 received by system 4700 via interface 3990 when system 4700 performs step 4610 of method 4600. Data storage 4760 also stores ultrasound exposure properties 4770 determined by system 4700 when performing step 4620 of method 4600. Ultrasound exposure properties 4770 may include a spatially resolved ultrasound intensity 4772 determined by system 4700 when performing step 4626. In certain embodiments, data storage 4760 stores sensor measurements 3970, such as temperature 3972 and/or pressure 3974 received by system 4700 via interface 3990 when system 4700 performs step 4612. Data storage 4760 may further store one or both of Doppler images 3984 (received by system 4700 via interface 3990 when system 4700 performs step 4650) and brightness images 3986.

Machine-readable instructions 4730 include treatment control instructions 4740 and one or more clutter-signal-to-treatment-efficacy correspondences 4750. Treatment control instructions 4740 are an embodiment of treatment control instructions 3940. When executed by processor 3910, treatment control instructions 4740 perform method 4600, utilizing at least one clutter-signal to treatment-efficacy correspondence 4750. Treatment control instructions 4740 include clutter signal evaluation instructions 4742 that, upon execution by processor 3910, evaluates a clutter signal image 3982 and utilizes at least one clutter-signal to treatment-efficacy correspondence 4750 to determine at least one ultrasound exposure property 4770. Treatment control instructions 4740 may further include temperature/pressure evaluation instructions 4744 and/or correspondence selection instructions 4746. Upon execution by processor 3910, temperature/pressure evaluation instructions 4744 perform step 4624 and, optionally, step 4640. Machine-readable instructions 4730 may include measurement instructions 3932, and optionally one or both of threshold temperature 3934 and threshold pressure 3936, and further utilize these when executing temperature/pressure evaluation instructions to perform step 4624 and, optionally, step 4640. Upon execution by processor 3910, correspondence selection instructions 4746 perform step 4628.

In an embodiment, clutter-signal to treatment-efficacy correspondences 4750 include a plurality of blood-perfusion specific correspondences 4752, and machine-readable instructions 4730 include blood perfusion evaluation instructions 4748. In this embodiment, processor 3910 may execute blood perfusion evaluation instructions 4748, retrieve a Doppler image 3984 from data storage 4760, and select a corresponding one of blood-perfusion specific correspondences 4752 to perform step 4629.

In an embodiment, machine-readable instructions 4730 include ultrasound imaging instructions 3950. Processor 3910 may execute ultrasound imaging instructions 3950 to perform step 4630. Treatment control instructions 4740 may further include beamforming instructions 3942 that, upon execution by processor 3910, perform step 4632.

Without departing from the scope hereof, system 4700 may be configured to be communicatively coupled with a modified version of electronic circuitry 3510 that drives an ultrasound transducer array of a different type than CMUT, such as a piezoelectric transducer array.

Figure 48:
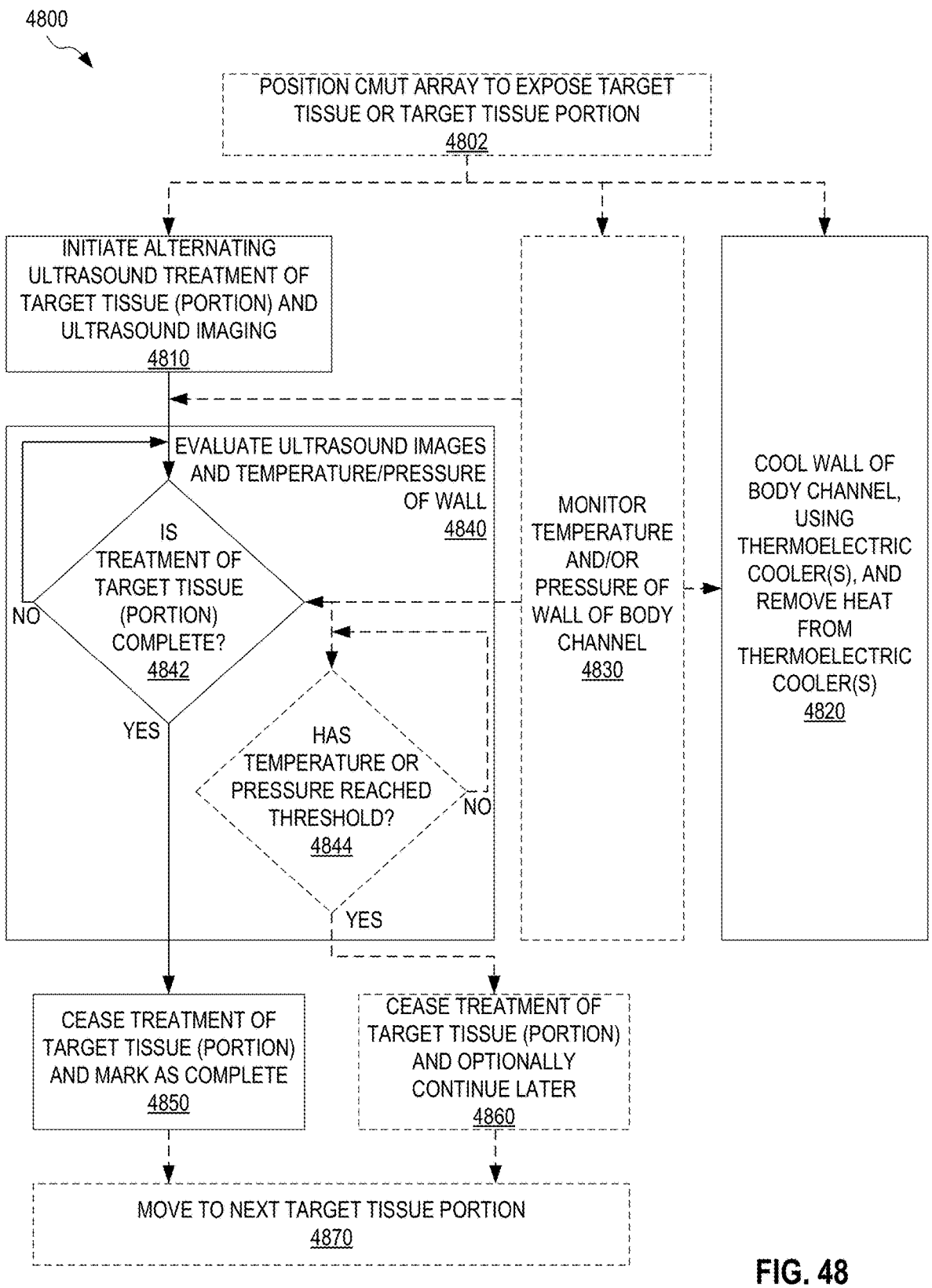
FIG. 48 illustrates a protocol for ultrasound treatment of target tissue, with solid state cooling, according to an embodiment.

FIG. 48 illustrates one protocol 4800 for ultrasound treatment of target tissue, with solid state cooling. Method 4400 may perform steps 4410, 4420, 4430, 4440, and 4450 according to protocol 4800, and method 4500 may perform steps 4510, 4520, 4530, 4540, and 4550 according to protocol 4800.

In a step 4810, protocol 4800 initiates alternating (a) ultrasound treatment of target tissue and (b) ultrasound imaging of tissue associated with the ultrasound treatment including the target tissue but optionally also including non-target tissue. The ultrasound treatment and the ultrasound imaging are performed from within a body channel by a CMUT array positioned in the body channel. In one example of step 4810, control module 140 of system 3900 initiates alternating (a) ultrasound treatment of target tissue 280 and (b) ultrasound imaging of target tissue 280 (and optionally also other tissue such as non-target tissue 290), wherein CMUT array 210 performs both the ultrasound treatment and the ultrasound imaging from within body channel 392. In one scenario, protocol 4800 is applied to treatment of target tissue that may be addressed from a single position and orientation of the CMUT array. In another scenario, protocol 4800 is applied to a treatment of target tissue of such extent that several different positions and/or orientations of CMUT array must be used to treat all of the target tissue. In this scenario, the ultrasound treatment initiated by step 4810 treats a portion of the target tissue. However, it should be understood that the ultrasound imaging initiated by step 4810 may image a larger portion of the target tissue than that being treated.

Protocol 4800 also includes step 4820. Step 4820 uses one or more thermoelectric coolers to cool a wall of the body channel, and further removes heat from the thermoelectric cooler(s) using a solid thermal conductor. Step 4820 is an embodiment of steps 4420 and 4430. In one example of step 4820, thermoelectric cooler(s) 220 cool wall 390 and solid thermal conductor 710 removes heat from thermoelectric cooler(s) 220. In certain embodiments, protocol 4800 further includes a step 4830 of monitoring the temperature and/or pressure of the wall of the body channel at or near the CMUT array. In one example of step 4830, sensor(s) 230 measure temperature and/or pressure of wall 390. Step 4830 is an embodiment of step 4440. Steps 4820 and 4830 are performed in parallel with the ultrasound treatment and imaging initiated by step 4810. Step 4820 may be performed based, at least in part, upon measurements obtained in step 4830. Without departing from the scope hereof, step 4820 may run the thermoelectric cooler(s) in reverse to heat the body channel wall, so as to prevent or compensate for over-cooling of the body channel wall.

Method 4820 performs a step 4840 while the ultrasound treatment and imaging, initiated by step 4810, is active. Step 4840 evaluates (a) ultrasound images obtained from the ultrasound imaging initiated by step 4810 and optionally, in embodiments including step 4830, (b) wall temperature/pressure measurements obtained in step 4830. Based upon this evaluation, step 4840 determines if the ultrasound treatment initiated by step 4810 should continue or be stopped.

In a decision step 4842, step 4840 determines if the ultrasound treatment of the target tissue, currently being treated by the CMUT array, is complete. If so, protocol 4800 proceeds to a step 4850 that ceases the ultrasound treatment (and optionally also the ultrasound imaging) initiated by step 4810 and marks the ultrasound treatment complete. In one scenario, step 4842 determines that the ultrasound treatment of the target tissue currently being treated is complete, based upon information (e.g., a clutter signal as discussed above in reference to FIGS. 46 and 47) obtained from one or more ultrasound images. In another scenario, step 4842 determines that the ultrasound treatment of the target tissue currently being treated is complete, based upon one or more temperature and/or pressure measurements obtained from step 4830. In this latter scenario, step 4840 back-projects the temperature/pressure value(s) to the target tissue, using a thermal model, to determine the temperature of the target tissue. In yet another example, step 4842 utilizes a combination of ultrasound images and temperature/pressure measurements to determine if the ultrasound treatment is complete.

Embodiments of protocol 4800 that include step 4830, step 4840 may further include a decision step 4844 that determines if a temperature or pressure of the body channel wall has reached a threshold value, above which damage to the body channel wall is likely to occur. If such a threshold value has been reached, protocol 4800 proceeds to a step 4860 that ceases the ultrasound treatment (and optionally also the ultrasound imaging) initiated by step 4810. If the treatment is not yet complete (as determined by step 4842), step 4860 may mark the treatment as being incomplete, and protocol 4800 may continue the ultrasound treatment of this target tissue later. In one implementation, protocol 4800 relies on step 4842 in the initial phase of treatment before further utilizing step 4844 in later phases of treatment.

Steps 4840, 4850, and 4860 may be performed by control module 140 or system 3900.

Protocol 4800 may include a step 4802, preceding step 4810, of positioning the CMUT array to expose the target tissue or a certain portion of the target tissue. Step 4802 may include adjusting the orientation of the CMUT array within the body channel and/or adjusting how far into the body channel the CMUT array is inserted.

In scenarios, wherein the extent of the target tissue is such that not all of the target tissue can be reached from a single fixed position/orientation of the CMUT array, step 4810 initiates treatment of a portion of the target tissue. In such scenarios, steps 4850 and 4860 may be followed by a step 4870 that repositions the CMUT array to target another portion of the target tissue, prior to protocol 4800 returning to step 4810 to initiate ultrasound treatment of this other portion of the target tissue. Protocol 4800 may perform several such iterations to treat all of the target tissue. In one example of such a scenario, protocol 4800 is applied to ultrasound treatment of prostate 192, for example treatment of BPH. In this example, protocol 4800 includes several repetitions of steps 4810, 4840, 4850, 4860, and 4870, wherein each repetition is associated with a different orientation of the CMUT array in urethra 194 to effect ultrasound treatment in essentially 360 degrees about urethra 194.

In one implementation of protocol 4800, steps 4802 and 4870 are performed manually by an operator. The operator may utilize an embodiment of handle 120 or catheter 110 that defines discrete positions/orientations of CMUT array 112 (or 210). In another implementation of protocol 4800, steps 4802 and 4870 are performed automatically using control module 140 or system 3900 and a motorized embodiment of handle 120 or catheter 110.

Certain embodiments of protocol 4800 may be encoded in either one of treatment control instructions 3940 and 4740.

Figure 49:
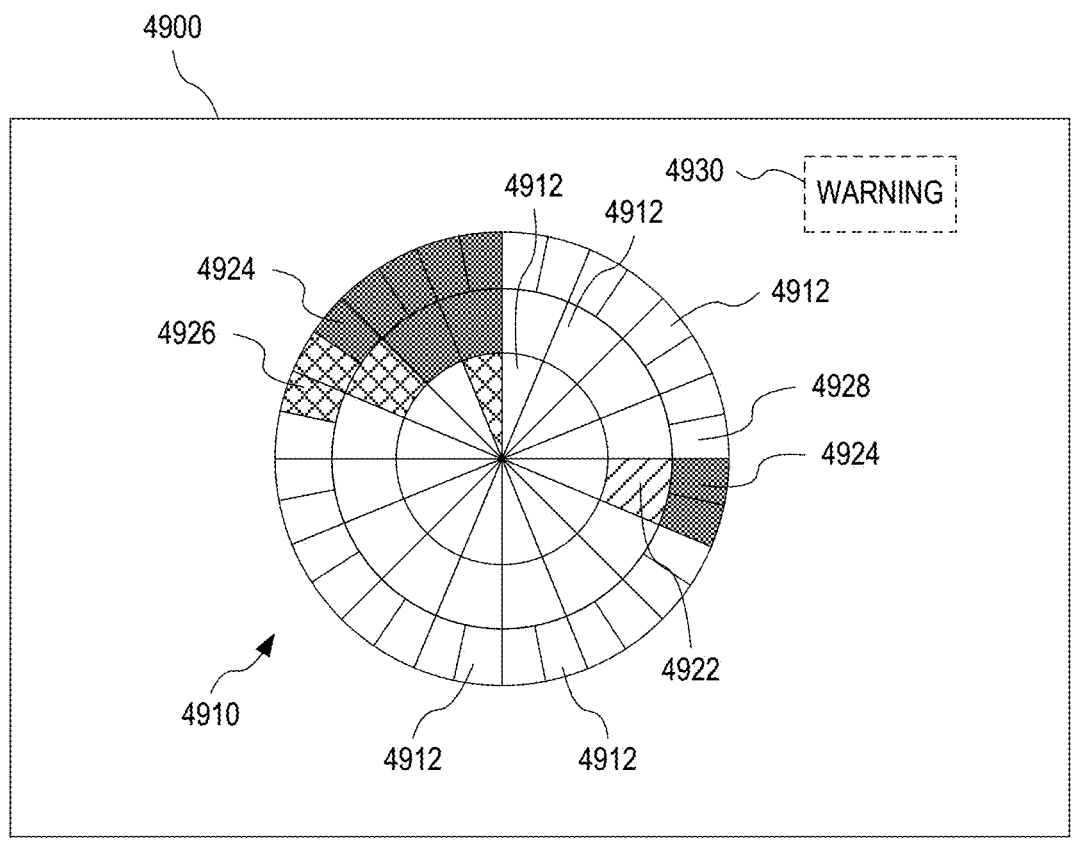
FIG. 49 illustrates a graphical user interface configured to be utilized in conjunction with the protocol of FIG. 48 to manage treatment of target tissue of an extent that requires several different positions/orientations of a CMUT array, according to an embodiment.

FIG. 49 illustrates one graphical user interface 4900 that may be utilized in conjunction with protocol 4800 to manage treatment of target tissue of an extent that requires several different positions/orientations of the CMUT array. User interface 4900 may be implemented in control module 140, or cooperatively implemented in system 3900 and a display communicatively coupled with system 3900.

User interface 4900 includes a treatment progress indicator 4910 that visually indicates treatment status of each portion of the target tissue. Each portion of the target tissue is represented by a segment 4912 of treatment progress indicator 4910. Color, shading, text, or another visual marker, is applied to each segment 4912 to indicate the treatment status of this segment 4912. Possible status types include currently being treated, treatment complete, treatment incomplete, and not yet exposed to treatment. In the example depicted in FIG. 49, one segment 4912 is in active status (label 4922), indicating that this segment 4912 is currently being exposed to ultrasound treatment initiated by step 4810 of protocol 4800. Several other segments 4912 have been treated and the treatment is complete (labels 4924). One segment 4912 has been treated but the treatment is not yet complete (label 4926). The remaining segments 4912 have not yet been exposed to treatment (labels 4928 and all segments 4912 with no shading in FIG. 49). For clarity of illustration, not all segments 4912, 4924, 4926, and 4928 are labeled in FIG. 49.

The particular example of treatment progress indicator 4910 shown in FIG. 49 is associated with a scenario wherein the CMUT array must be placed in several different orientations, for example to perform 360 degrees of treatment of prostate 192, while treating from the outside toward the inside. In certain scenarios, treatment may be most effective when, at any given orientation of the CMUT array, the ultrasound is first focused on the most distant segment before working inwards. This ensures that the ultrasound does not need to pass through tissue with significant necrosis before reaching the target segment; necrosis may adversely affect the ultrasound propagation properties. In the example shown in FIG. 49, each segment 4912 corresponds to a respective orientation of the CMUT array and radial distance at which the ultrasound is focused. Without departing from the scope hereof, treatment progress indicator 4910 may be tailored to display translation of the CMUT array rather than, or in combination with, rotation of the CMUT array. Also without departing from the scope hereof, treatment progress indicator 4910 may include more or fewer segments 4912 than shown in FIG. 49, for example only segmentation according to orientation and not radial distance. User interface 4900 may be used together with (a) an embodiment of handle 120 or catheter 110 that senses the position/orientation of the CMUT array and (b) a computer (such as control module 140 or system 3900) that processes the sensed position/orientation together with the radial focus distance of the ultrasound. When an operator manually controls the orientation/position of the CMUT array, user interface 4900 provides the operator with information about which segments 4912 that need treatment or further treatment and which segments 4912 should not receive further treatment. When the repositioning/refocusing of the CMUT array is performed automatically, for example controlled by control module 140 or system 3900, user interface 4900 shows progress of the treatment. Software associated with user interface 4900 may be configured to prevent treatment of a radially more inward segment 4912 prior to treatment of a radially more outward segment 4912.

In certain embodiments, user interface 4900 includes a warning indicator 4930 that displays a warning to an operator if, e.g., it is time to manually reposition/refocus the CMUT array or if the CMUT array has been positioned incorrectly.

Figure 50:
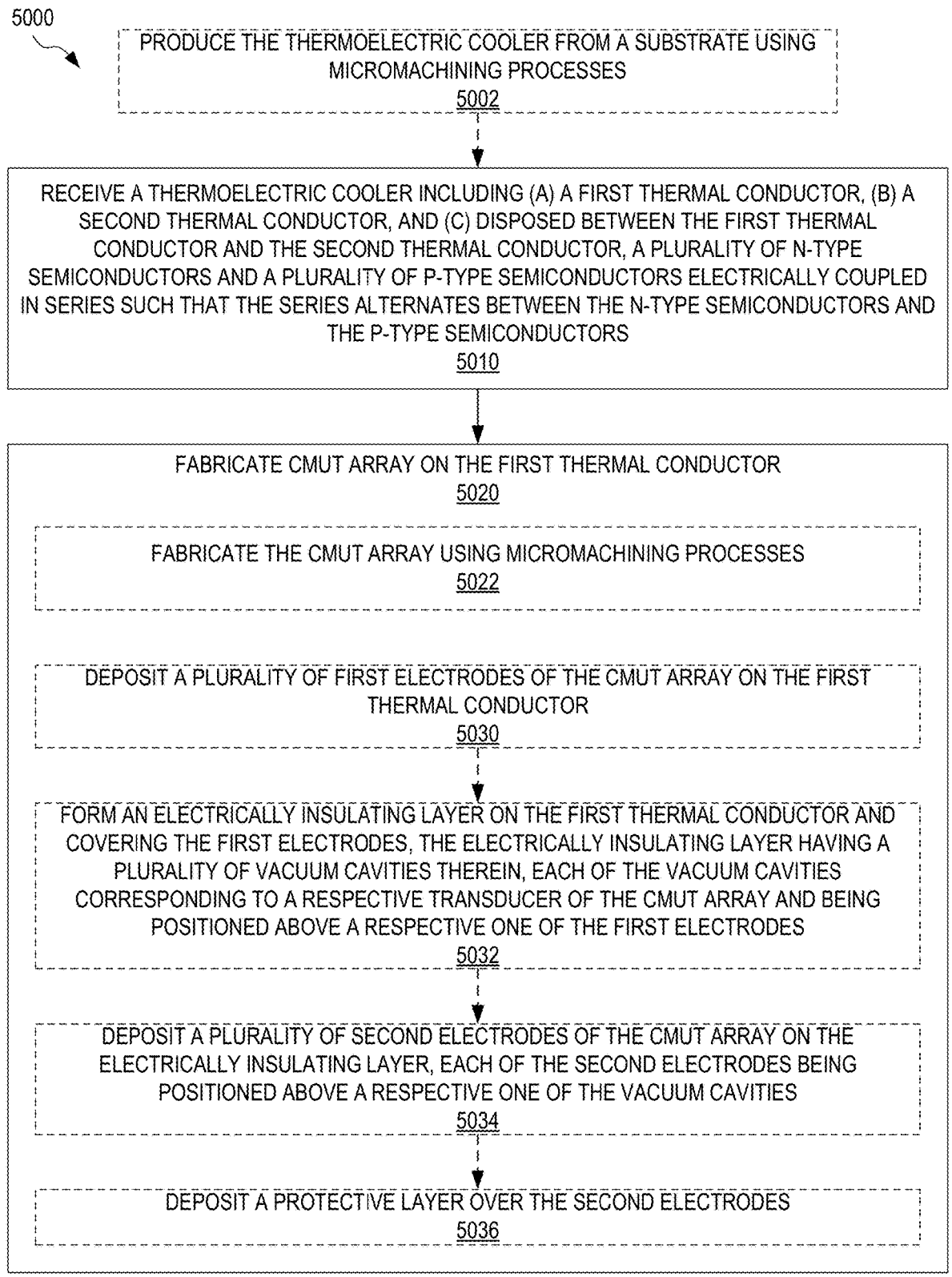
FIG. 50 illustrates a method for manufacturing a CMUT array with solid state cooling, according to an embodiment.

FIG. 50 illustrates one method 5000 for manufacturing a CMUT array with solid state cooling, wherein the CMUT array is manufactured directly on a thermoelectric cooler. Method 5000 may be used to manufacture CMUT-TEC device 1200. Method 5000 may also be used to manufacture an embodiment of CMUT-TEC device 200 having CMUT array 210 in direct physical contact with thermoelectric cooler 220, for example as in CMUT-TEC device 500.

Method 5000 includes steps 5010 and 5020. Step 5010 receives a thermoelectric cooler that includes two thermal conductors and, disposed between the two thermal conductors, a plurality of n-type semiconductors and a plurality of p-type semiconductors electrically coupled in series such that the series alternates between the n-type semiconductors and the p-type semiconductors. Step 5020 fabricates a CMUT array on one of the thermal conductors of the thermoelectric cooler. In one example of method 5000, step 5010 receives thermoelectric cooler 1210, and step 5020 fabricates CMUT array 210 on thermal conductor 1242 of thermoelectric cooler 1210.

Method 5000 may further include a step 5002, preceding step 5010, of producing the thermoelectric cooler from a substrate using micromachining processes. Additionally, step 5020 may implement a step 5022 of fabricating the CMUT array using micromachining processes.

In an embodiment, step 5020 includes steps 5030, 5032, 5034, and 5036. Step 5030 deposits a plurality of first electrodes of the CMUT array (yet to be completed) on a first one of the two thermal conductors of the thermoelectric cooler. Step 5032 forms an electrically insulating layer on the first thermal conductor. The electrically insulating layer covers the first electrodes and has a plurality of vacuum cavities. Each of the vacuum cavities corresponds to a respective transducer of the CMUT array and is positioned above a respective one of the first electrodes. Step 5034 deposits a plurality of second electrodes of the CMUT array on the electrically insulating layer. Each of the second electrodes is positioned above a respective one of the vacuum cavities. Step 5036 deposits a protective layer over the second electrodes. The protective layer may be electrically insulating.

Without departing from the scope hereof, steps 5010 and 5020 (and, optionally, step 5002) may be performed with a thermoelectric cooler not yet equipped with the second thermal conductor. This second thermal conductor may be formed at a later stage, or the ultrasound transducer array may be mounted on a thermal conductor that serves as the second thermal conductor. Also without departing from the scope hereof, electrodes between the p-type and n-type semiconductors on the side of the thermoelectric cooler facing away from the CMUT array may be formed after step 5020.

It is understood that the thermoelectric coolers of the present disclosure, such as thermoelectric cooler 114 or 220, may be extended to use with non-CMUT type ultrasound transducers such as piezoelectric ultrasound transducers and ultrasound transducers known in the art. The presently disclosed thermoelectric coolers may be thermally coupled to such ultrasound transducers to cool the ultrasound transducers, and the heat harvested by the thermoelectric cooler(s) may be removed by a thermal conductor, such as solid thermal conductor 710. Piezoelectric ultrasound transducers are frequently operated below their full capacity to avoid overheating of the piezoelectric transducers. One or more of the presently disclosed thermoelectric coolers may be thermally coupled to a piezoelectric transducer, or a piezoelectric transducer array, and provide sufficient cooling to allow ultrasound generation closer to the full capacity of the piezoelectric transducer(s).

Figure 51:
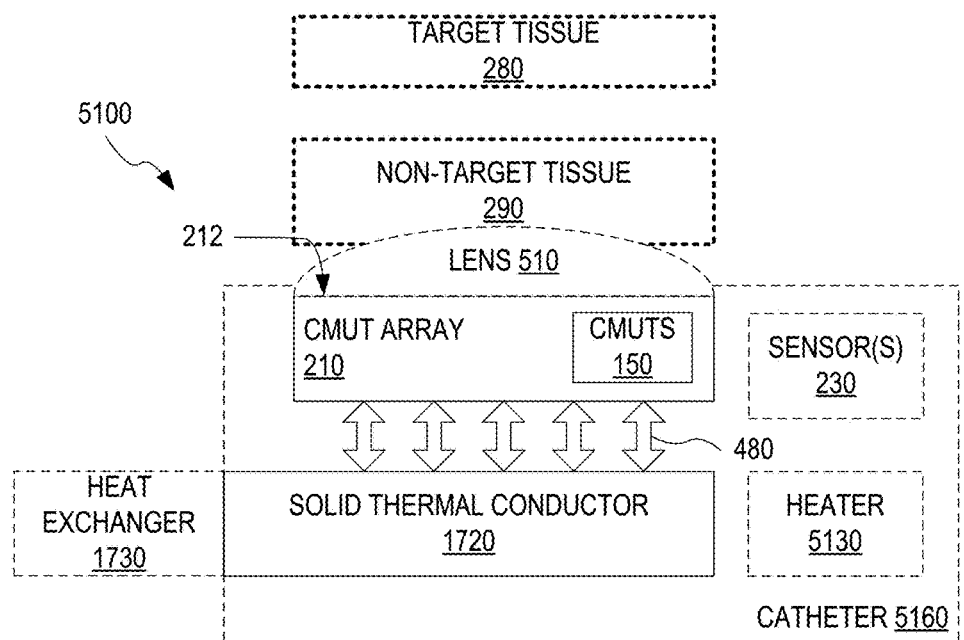
FIG. 51 illustrates a medical CMUT device with passive cooling, according to an embodiment.

FIG. 51 illustrates one medical CMUT device 5100 with passive cooling. CMUT device 5100 includes CMUT array 210 and solid thermal conductor 1720. CMUT device 5100 is a modification of device 700 that, instead of utilizing thermoelectric cooler(s) 220 to actively cool non-target tissue 290 via CMUT array 210, utilizes solid thermal conductor 1720 to passively cool non-target tissue 290 via CMUT array 210. Solid thermal conductor 1720 is in thermal coupling 480 with CMUT array 210. CMUT device 5100 is configured to cooperate with heat exchanger 1730. In operation, when cooling of non-target tissue 290 is needed, heat exchanger 1730 cools solid thermal conductor 1720, thereby removing heat from non-target tissue 290 via CMUT array 210. For example, when CMUT device 5100 is implemented in a catheter 5160, solid thermal conductor 1720 extends to a handle that is coupled to the proximate end of catheter 5160 (outside the body channel) and includes heat exchanger 1730. CMUT device 5100 may be provided together with heat exchanger 1730, for example, incorporated in catheter 5160 and a handle, respectively. Alternatively, CMUT device 5100 or catheter 5160 may be provided as a standalone device configured for coupling with a heat exchanger 1730 provided by a third party.

In certain embodiments, catheter 5160 includes a heater 5130. Heater 5130 is, for example, a resistive heater. In certain treatment scenarios, passive cooling of non-target tissue 290 by solid thermal conductor 1720 requires cooling solid thermal conductor 1720 to a temperature that is uncomfortable or damaging to the patient when CMUT array 210 is turned off and therefore does not heat non-target tissue 290. Since solid thermal conductor 1720 is always in thermal coupling 480 with CMUT array 210 and the thermal mass of thermal conductor 1720 prevents instantaneous heating of solid thermal conductor 1720, it may not be possible to turn off cooling by solid thermal conductor as quickly as the ultrasound induced heating of non-target tissue 290 dissipates. Thus, when CMUT array 210 is turned off, non-target tissue 290 may be over-cooled by solid thermal conductor 1720. Similarly, it may be necessary to at least begin cooling down solid thermal conductor 1720 some time prior to turning on CMUT array 210 to ensure that solid thermal conductor 1720 can sufficiently cool non-target tissue 290 when CMUT array 210 is turned on. During this pre-cooling phase, solid thermal conductor 1720 may over-cool non-target tissue 290. Heater 5130 is configured with low thermal mass and, hence, provides temperature control on a faster time scale than that of solid thermal conductor 1720.

Although CMUT device 5100 does not benefit from certain advantages of thermoelectric cooling, such as easy and rapid temperature control, CMUT device 5100 does provide cooling directly at the treatment location (as opposed to in another nearby body channel). CMUT device 5100 also has benefits over a liquid-cooled catheter tip. In particular, CMUT device 5100 performs passive cooling without having to introduce a liquid coolant into the body channel Thus, there is no risk of liquid coolant leaking out of catheter 5160 to directly expose the patient, and catheter CMUT device 5100/catheter 5160 does not require regulatory approval of introduction of a liquid coolant into the patient.

In an embodiment, CMUT device 5100 includes lens 510, as discussed above in reference to FIG. 5. CMUT device 5100 may also include one or more sensor(s) 230 as discussed above in reference to FIG. 2.

Without departing from the scope hereof, CMUT device 5100 may be implemented in catheters 1700, 1800, and 1900, in tubular catheter jacket 2300, in catheters 2550, and 2650, and in devices 3700 and 3800, in place of CMUT-TEC device 200 and solid thermal conductor 1720. Also without departing from the scope hereof, CMUT device 5100 may be implemented in systems 4000, 4100, 4200, and 4300.

Figure 52:
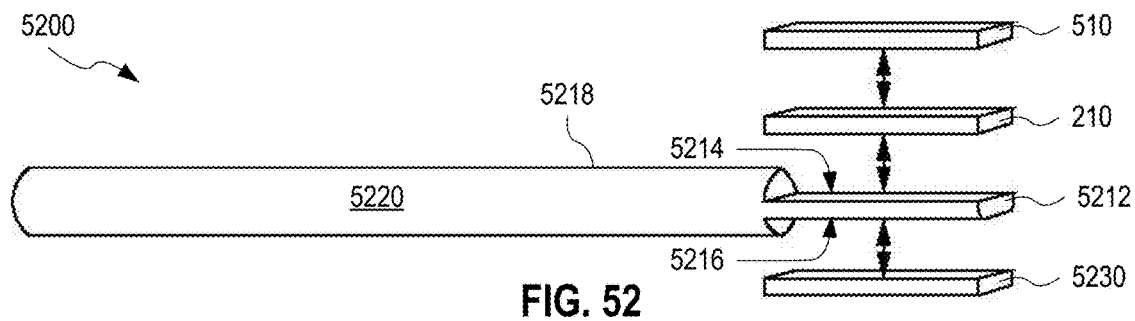
FIGS. 52-54 show different example configurations of the CMUT device of FIG. 51.

FIG. 52 is an exploded view of one configuration 5200 of CMUT device 5100 that includes a heater. Configuration 5200 implements solid thermal conductor 1720 as a solid thermal conductor 5220 having a rod section 5218 and a flattened section 5212. In one embodiment, rod section 5218 and flattened section 5212 are parts of an integrally formed, solid piece. Flattened section 5212 has a top surface 5214 and a bottom surface 5216. CMUT array 210 and lens 510 are disposed on top surface 5214, and a resistive heater 5230 is coupled to bottom surface 5216. Resistive heater 5230 is an embodiment of heater 5130.

Figure 53:
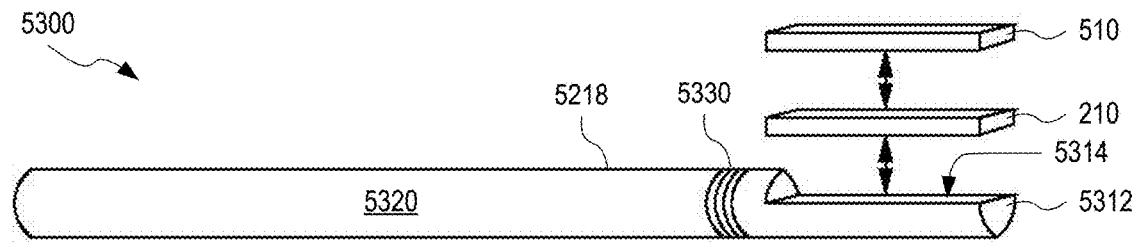

FIG. 53 is an exploded view of another configuration 5300 of CMUT device 5100 that includes a heater. Configuration 5300 implements solid thermal conductor 1720 as a solid thermal conductor 5320 having rod section 5218 and an at least partly flattened section 5312. In one embodiment, rod section 5218 and flattened section 5312 are parts of an integrally formed, solid piece. Flattened section 5312 has a top surface 5314. CMUT array 210 and lens 510 are disposed on top surface 5314, and a resistive heater 5330 is wound around rod section 5218 near flattened section 5312. Resistive heater 5330 is an embodiment of heater 5130.

Figure 54:
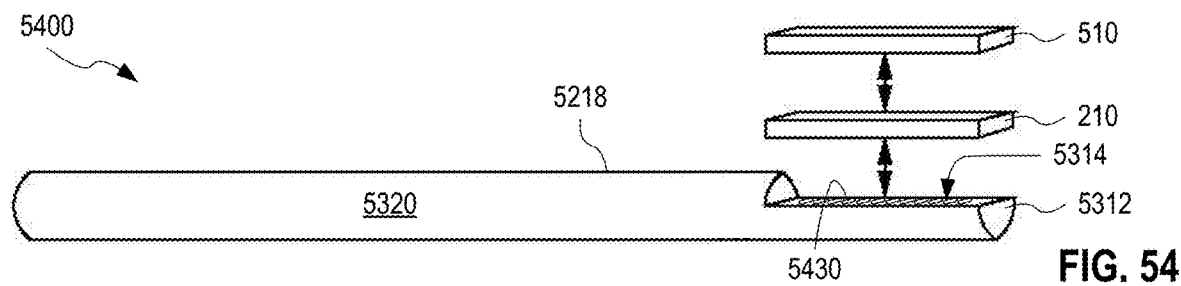

FIG. 54 is an exploded view of yet another configuration 5400 of CMUT device 5100 that includes a heater. Configuration 5400 implements solid thermal conductor 1720 as solid thermal conductor 5320. CMUT array 210 and lens 510 are disposed on top surface 5314, with a resistive heater 5430 on flattened section 5312 at the interface between top surface 5314 and CMUT array 210. In one implementation, resistive heater 5430 is wire that is embedded in a thermal adhesive between top surface 5314 and CMUT array 210. Resistive heater 5430 is an embodiment of heater 5130.

Figure 55:
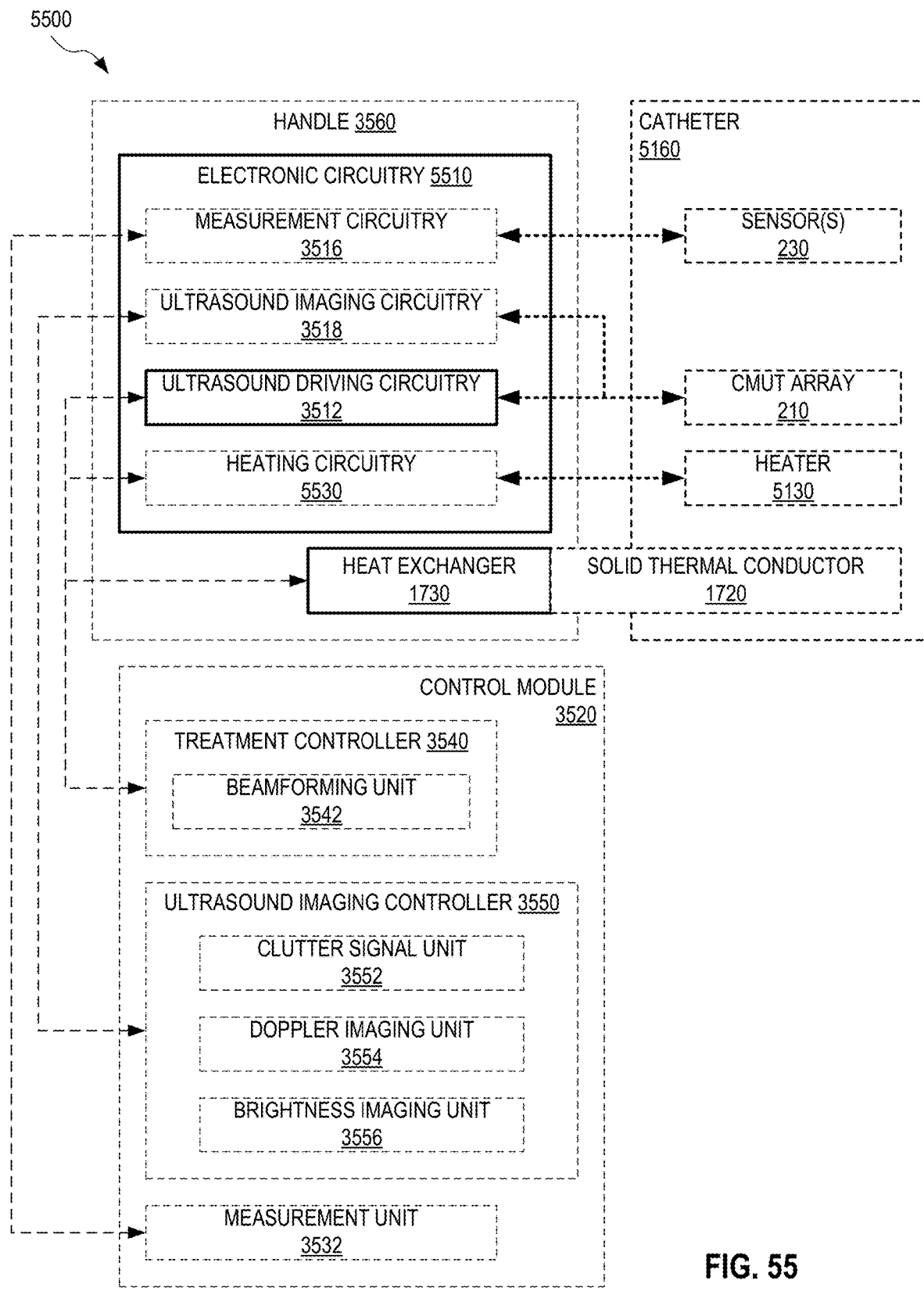
FIG. 55 illustrates a system for ultrasound treatment with passive cooling, according to an embodiment.

FIG. 55 illustrates one system 5500 for ultrasound treatment with passive cooling. System 5500 is similar to system 3500 apart from being configured for passive cooling by solid thermal conductor 1720 instead of active cooling by thermoelectric cooler 220. System 5500 includes electronic circuitry 5510 (in place of electronic circuitry 3510) and heat exchanger 1730, optionally mounted together in handle 3560. Electronic circuitry 5510 and heat exchanger 1730 are configured to cooperate with catheter 5160. Electronic circuitry 5510 is an adaptation of electronic circuitry 3510 that does not include Peltier driving circuitry 3514. Electronic circuitry 5510 may include heating circuitry 5530 to drive heater 5130, when electronic circuitry 5510 is coupled with an embodiment of catheter 5160 that includes heater 5130. In an embodiment of system 5500, treatment controller 3540 is adapted to control heating circuitry 5530 (when included) and/or at least partly control heat exchanger 1730. In this embodiment, treatment controller 3540 may cooperate with measurement unit 3532 to control heating circuitry 5530 (when included) and/or heat exchanger 1730 based upon measurements obtained from sensor(s) 230 (when included).

Figure 56:
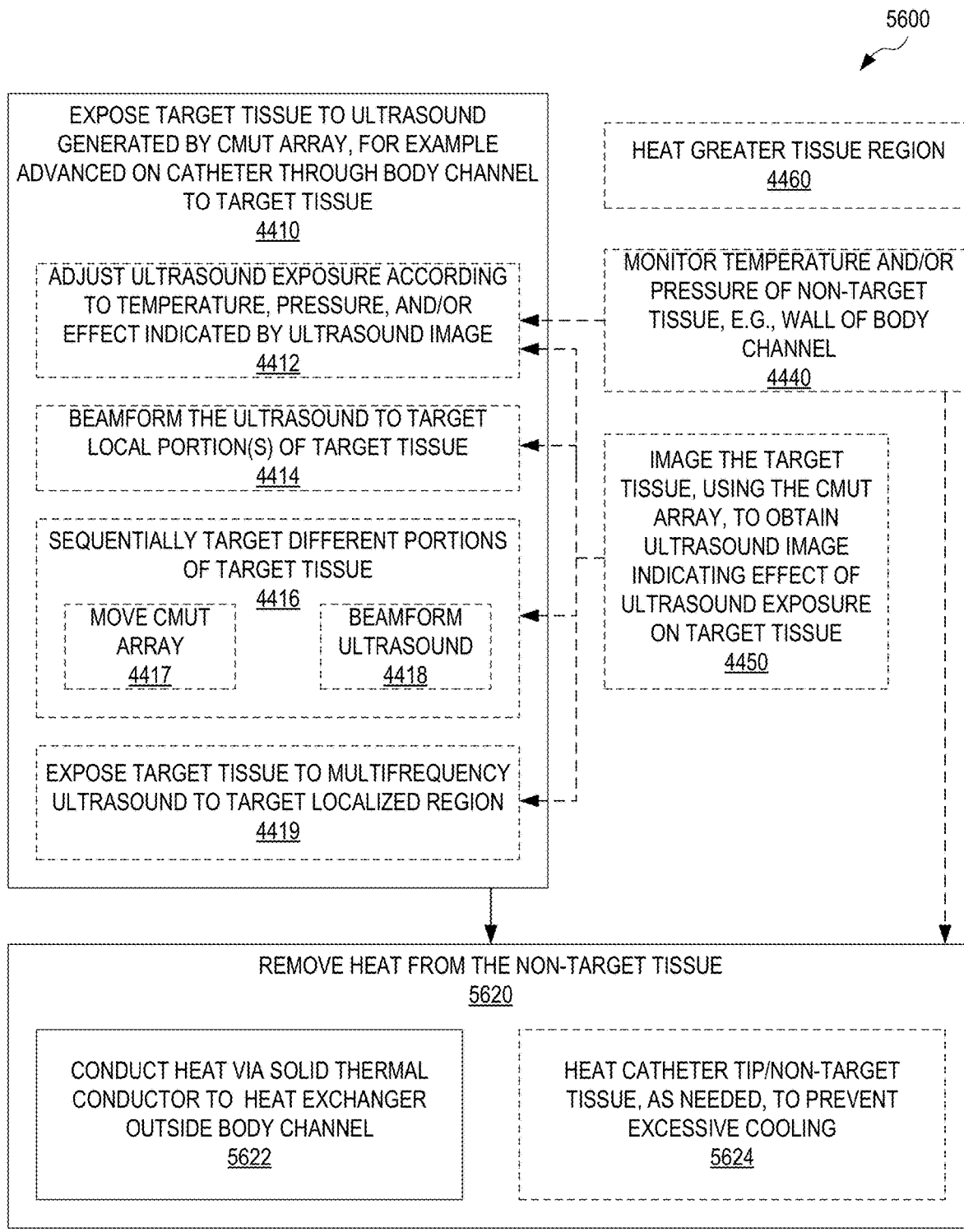
FIG. 56 illustrates a method for ultrasound treatment with passive cooling, according to an embodiment.

FIG. 56 illustrates one method 5600 for ultrasound treatment with passive cooling. Method 5600 is performed by catheter 5160 and heat exchanger 1730, for example. The performance of method 5600 may be commanded by treatment controller 3540 utilizing electronic circuitry 5510. Certain embodiments of method 5600 may be encoded in machine-readable instructions 3930 as treatment control instructions 3940. Other embodiments of method 5600 may be encoded in machine-readable instructions 3930 as treatment control instructions 3940 in combination with one or both of measurement instructions 3932 and ultrasound imaging instructions 3950.

Method 5600 is similar to method 4400 apart from steps 4420 and 4430 being replaced by a step 5620. Step 5620 removes heat from the non-target tissue. Step 5620 includes a step 5622 that conducts the heat from the non-target tissue via a solid thermal conductor to a heat exchanger outside the body channel. In one example of steps 5620 and 5622, heat exchanger 1730 cools solid thermal conductor 1720 of catheter 5160, such that solid thermal conductor 1720 removes heat from non-target tissue 290 via CMUT array 210. Heat exchanger 1730 may utilize liquid cooling of solid thermal conductor 1720, for example by liquid nitrogen, antifreeze cooled to −30 degrees Celsius, chilled water at near-zero degrees Celsius, or room temperature water. Step 5620 may include a step 5624 of heating the catheter tip, and thus the non-target tissue, as needed to prevent excessive cooling. In one example of step 5624, heater 5130 heats at least a portion of the tip of catheter 5160 to heat non-target tissue 290, so as to prevent or compensate for over-cooling of non-target tissue 290 by solid thermal conductor 1720.

Figure 57:
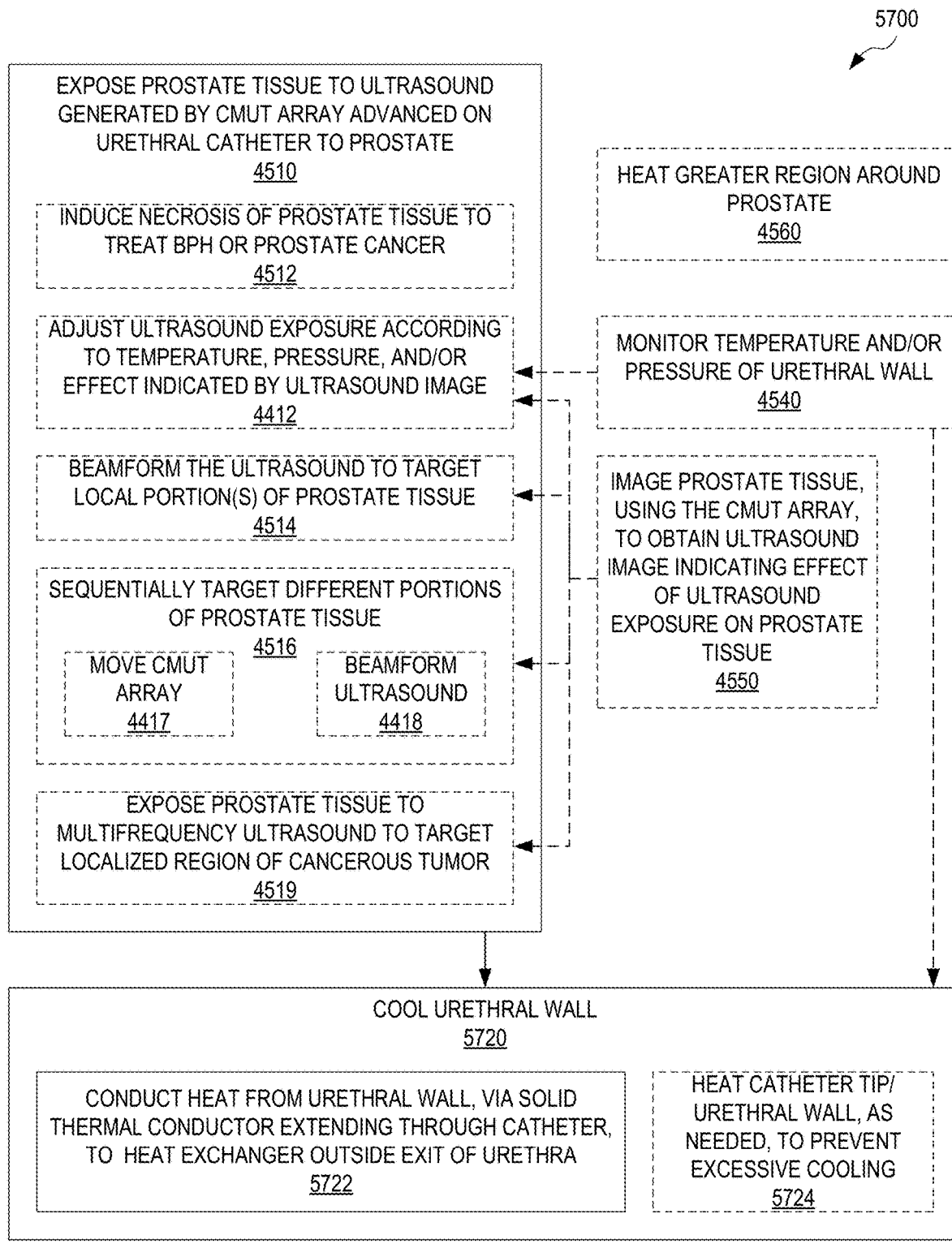
FIG. 57 illustrates a method for ultrasound treatment of a prostate with passive cooling of the urethra, according to an embodiment.

FIG. 57 illustrates one method 5700 for ultrasound treatment of prostate 192 with passive cooling of the urethra 194. Method 5700 is performed by catheter 5160 and heat exchanger 1730, for example Method 5700 is an embodiment of method 5600 specifically adapted for ultrasound treatment of prostate 192, for example to treat BPH or prostate cancer.

Method 5700 includes steps 4510 and 5720, which are embodiments of steps 4410 and 5620, respectively. Step 4510 is discussed above in reference to FIG. 45. Step 5720 removes heat from the wall of urethra 194. Step 5720 includes a step 5722 that conducts the heat from the wall of urethra 194 via a solid thermal conductor to a heat exchanger outside urethra 194. Step 5720 may include a step 5724 of heating the catheter tip, and thus the wall of urethra 194, as needed to prevent excessive cooling. Steps 5722 and 5724 are embodiments of steps 5622 and 5624, respectively.

Method 5700 may further include steps 4540, 4550, and/or 4560, as discussed above in reference to FIG. 46.

Without departing from the scope hereof, each of methods 5600 and 5700 may implement method 4600 in step 4412.

Also without departing from the scope hereof, each of methods 5600 and 5700 may be performed according to protocol 4800.

EXAMPLE I

Modeling of Cooling Performance of CMUT-TEC Device

The thermal properties of an embodiment of device 700 and adjacent tissue have been evaluated using an electrical circuit model and the software SPICE (Simulation Program with Integrated Circuit Emphasis). The model takes advantage of the fact that thermal conduction and electrical conduction are governed by analogous physical laws. The model assumes that (a) device 700 includes lens 510, (b) solid thermal conductor 710 is coupled to a heat exchanger, such as heat exchanger 1730, and (c) solid thermal conductor 710 is housed in a stainless steel catheter jacket. The model takes into account ultrasound heating of both the adjacent tissue and lens 510, and further takes into account heat generated by the thermoelectric coolers. The model accounts for thermal couplings between the solid thermal conductor, the heat exchanger, the stainless steel catheter jacket, the thermoelectric coolers, the CMUT, the lens, and the tissue.

In this example, solid thermal conductor 710 is a copper rod shaped in a manner similar to solid thermal conductor 5320, wherein rod section 5218 is 20 cm long and has a diameter of 3.2 mm, and wherein flattened section 5312 is 2.5 cm long. (Heater 5330 is not included in the model.) Six thermoelectric coolers (Marlow, NL1020T) are attached side-by-side to top surface 5314 with thermal epoxy and run in parallel, and a CMUT is attached to the side of the thermoelectric coolers facing away from top surface 5314. The CMUT active area is 3.4 mm by 25.6 mm. Each thermoelectric cooler covers an area of approximately 3.4 mm by 3.4 mm and has a thickness of 1.6 mm. The stainless steel catheter jacket has an inner diameter of 4 mm, an outer diameter of 5 mm, and a length of 20 cm. The stainless steel catheter jacket houses rod section 5218. The CMUT generates 10 Watts of ultrasound when turned on. When turned on, each thermoelectric cooler is driven with a current of 0.3 Amperes, which has been found to provide optimal cooling performance The temperature at the lens-tissue interface is modeled as a function of time after turning on the CMUT and thermoelectric coolers. The calculations are performed for different temperatures of the cooling reservoir of the heat exchanger and for two different materials of lens 510 (Sylgard 160 and RTV-615). Table 1 lists steady state temperatures, in degrees Celsius, at the lens-tissue interface when heating and cooling have reached equilibrium. Table 2 lists rise times (in seconds) from a steady-state temperature, with no heating or cooling engaged, to a temperature of 41 degrees at the lens-tissue interface, with and without thermal insulation between the solid thermal conductor and the stainless steel catheter jacket.

TABLE 1

| Cooling reservoir | Steady-State Temperature | |
|---|---|---|
| temperature | Sylgard 160 | RTV-615 |
| −186° C. | 55° C. | 33° C. |
| −30° C. | 67° C. | 44° C. |

TABLE 1-continued

| Cooling reservoir temperature | Steady-State Temperature | |
| --- | --- | --- |
| | Sylgard 160 | RTV-615 |
| 0° C. | 69° C. | 46° C. |
| 24° C. | 71° C. | 48° C. |

TABLE 2

| | Rise-Time to 41° C. | | | |
| --- | --- | --- | --- | --- |
| | Sylgard 160 | | RTV-615 | |
| Cooling reservoir temperature | Without insulation | With insulation | Without insulation | With insulation |
| −186° C. | 31.3 s | 98.5 s | ∞ | ∞ |
| −30° C. | 4.7 s | 8.2 s | 78.2 s | 147 s |
| 0° C. | 2.7 s | 3.7 s | 48.0 s | 63.0 s |
| 24° C. | 1.5 s | 1.5 s | 32.3 s | 34.1 s |

The results listed in Table 1 and Table 2 demonstrate that cooling is most effective when the cooling reservoir temperature is low, and that the reduced ultrasound attenuation of RTV-615, as compared to Sylgard 160, results in a lower steady-state temperature at the lens-tissue interface as well as a longer rise-time to 41° C. In one treatment scenario, the on-time of the CMUT is limited to the corresponding rise-time listed in Table 2, to prevent the temperature at the lens-tissue interface from exceeding 42° C. Treatment may be resumed when the temperature at the lens-tissue interface has dropped by a desired amount. The thermoelectric coolers may be left on to accelerate this cooling.

The heating of the target tissue has been simulated using a bio-heat transfer equation. This simulation shows that the volume of necrosed tissue is a highly non-linear function of ultrasound exposure time. In one example, two seconds of exposure causes necrosis of a tissue volume of about 2.5 mm$^3$, but an additional two-second exposure causes necrosis of an additional tissue volume of almost 10 mm$^3$. Thus, ultrasound treatment may be significantly more effective when the cooling provides for a long rise-time (see Table 2) to a maximum upper temperature.

EXAMPLE II

Modeling of Cooling Performance of Passively Cooled CMUT Device

The thermal properties of an embodiment of CMUT device 5100 and adjacent tissue has been evaluated using an electrical circuit model and the software SPICE (Simulation Program with Integrated Circuit Emphasis), in a manner similar to that discussed above in Example I, except without thermoelectric coolers. Table 3 lists steady state temperatures, in degrees Celsius, at the lens-tissue interface when heating and cooling have reached equilibrium, with and without thermal insulation between the solid thermal conductor and the stainless steel catheter jacket. Table 4 lists rise times (in seconds) from a steady-state temperature, with no heating or cooling engaged, to a temperature of 41 degrees at the lens-tissue interface, with and without thermal insulation between the solid thermal conductor and the stainless steel catheter jacket.

TABLE 3

| | Steady-State Temperature | | | |
| --- | --- | --- | --- | --- |
| | Sylgard 160 | | RTV-615 | |
| Cooling reservoir temperature | Without insulation | With insulation | Without insulation | With insulation |
| −186° C. | 52° C. | 42° C. | 33° C. | 23° C. |
| −30° C. | 66° C. | 64° C. | 45° C. | 43° C. |
| 0° C. | 68° C. | 68° C. | 48° C. | 47° C. |
| 24° C. | 71° C. | 72° C. | 50° C. | 50° C. |

TABLE 4

| | Rise-Time to 41° C. | | | |
| --- | --- | --- | --- | --- |
| | Sylgard 160 | | RTV-615 | |
| Cooling reservoir temperature | Without insulation | With insulation | Without insulation | With insulation |
| −186° C. | 43 s | 279 s | ∞ | ∞ |
| −30° C. | 4.0 s | 8.4 s | 28.9 s | 60.0 s |
| 0° C. | 1.8 s | 3.3 s | 22.2 s | 30.1 s |
| 24° C. | 0.7 s | 1.0 s | 12.3 s | 14.5 s |

The results listed in Table 3 and Table 4 demonstrate that cooling is most effective when the cooling reservoir temperature is low, and that the reduced ultrasound attenuation of RTV-615, as compared to Sylgard 160, results in a lower steady-state temperature at the lens-tissue interface as well as a longer rise-time to 41° C. At the lowest cooling reservoir temperatures, the rise-times with passive cooling are as long as or longer than the rise-times with thermoelectric cooling (see Table 2). However, in these scenarios, to prevent over-cooling of the patient's tissue, heater 5130 may need to be engaged when the ultrasound emission is off. For higher cooling reservoir temperatures, the rise-times achieved with passive cooling are shorter than those achieved with thermoelectric cooling.

Combinations of Features

Features described above as well as those claimed below may be combined in various ways without departing from the scope hereof. For example, it will be appreciated that aspects of one medical device, system or method, described herein may incorporate or swap features of another medical device, system, or method, described herein. The following examples illustrate possible, non-limiting combinations of embodiments described above. It should be clear that many other changes and modifications may be made to the methods and device herein without departing from the spirit and scope of this invention:

(A1) A medical device may include a capacitive micromachined ultrasonic transducer (CMUT) array configured to emit ultrasound to target tissue, and at least one thermoelectric cooler mechanically coupled with the CMUT array and configured to cool non-target tissue heated by the ultrasound.

(A2) In the device denoted as (A1), the CMUT array may be configured to project the ultrasound from a first side of the CMUT array, and each thermoelectric cooler may be thermally coupled to a second side of the CMUT array.

(A3) In the device denoted as (A2), the first side of the CMUT array may be configured to be thermally coupled with the non-target tissue, to facilitate cooling of the non-target tissue by the at least one thermoelectric cooler through the CMUT array.

(A4) Either of the devices denoted as (A2) and (A3) may further include an acoustic lens disposed on the first side of the CMUT array, wherein the acoustic lens is configured to be thermally coupled with the non-target tissue to provide a thermal pathway between the non-target tissue and the at least one thermoelectric cooler through the CMUT array and the acoustic lens.

(A5) In the device denoted as (A4), the acoustic lens may be configured to be in physical contact with the non-target tissue.

(A6) Any of the devices denoted as (A1) through (A5) may further include a solid thermal conductor thermally coupled to each thermoelectric cooler to remove heat from the thermoelectric cooler.

(A7) In the device denoted as (A6), each thermoelectric cooler may be implemented in a layer having (a) a first side thermally coupled to the second side of the CMUT array and (b) a second side facing away from the first side of the layer and thermally coupled to the solid thermal conductor.

(A8) In either of the devices denoted as (A6) and (A7), the solid thermal conductor may include metal.

(A9) Any of the devices denoted as (A1) through (A8) may include a silicon substrate with the CMUT array, wherein each thermoelectric cooler is bonded to the silicon substrate via a thermally conductive adhesive.

(A10) Any of the devices denoted as (A1) through (A9) may further include one or more sensors for sensing a property of the non-target tissue, wherein the property may be selected from the group consisting of temperature, pressure, and a combination of temperature and pressure.

(A11) In the device denoted as (A10), each of the sensors may be a solid state sensor.

(A12) In the device denoted as (A11), the one or more solid state sensors may include a strain gauge configured to sense pressure of the non-target tissue.

(A13) In any of the devices denoted as (A1) through (A12), the CMUT array may be planar.

(A14) In any of the devices denoted as (A1) through (A12), the CMUT array may include two planar CMUT subarrays positioned at an angle to each other.

(A15) In the device denoted as (A14), respective ultrasound emission faces of the two planar CMUT subarrays may be angled away from each other to increase angular range of the CMUT array.

(A16) In the device denoted as (A15), each of the planar CMUT subarrays may be elongated in a first dimension, wherein an angle between the respective ultrasound emission faces of the two planar CMUT subarrays is in a plane orthogonal to the first dimension.

(A17) In either of the devices denoted as (A15) and (A16), the angle between respective normal vectors of the ultrasound emission faces may be in the range between 45 and 90 degrees.

(B1) A catheter for ultrasound treatment with solid state cooling may include (a) a capacitive micromachined ultrasonic transducer (CMUT) array configured to emit ultrasound to target tissue, (b) a thermoelectric cooler configured to cool non-target tissue heated by the ultrasound, wherein the ultrasound transducer is disposed at a distal end of the catheter, and (c) a solid thermal conductor coupled to the thermoelectric cooler and extending along the catheter away from the distal end toward a proximal end of the catheter, to conduct heat away from the thermoelectric cooler.

(B2) In the catheter denoted as (B1), the thermoelectric cooler may be mechanically coupled with the CMUT array.

(B3) In either of the catheters denoted as (B1) and (B2), the solid thermal conductor may include a metal conductor.

(B4) In the catheter denoted as (B3), the metal conductor may be a flexible braided-wire metal conductor.

(B5) Any of the catheters denoted as (B1) through (B4) may further include first electrical conductors configured to electrically couple the CMUT array to ultrasound driving circuitry external to the catheter, and second electrical conductors configured to electrically couple the thermoelectric cooler to Peltier driving circuitry, external to the catheter, for driving the thermoelectric cooler.

(B6) Any of the catheters denoted as (B1) through (B5) may further include a temperature sensor for sensing temperature of the non-target tissue.

(B7) Any of the catheters denoted as (B1) through (B6) may further include a pressure sensor for sensing pressure of the non-target tissue.

(B8) Any of the catheters denoted as (B1) through (B7) may be configured for insertion into a urethra, wherein the target tissue is a prostate and the non-target tissue is at least a portion of wall of the urethra.

(B9) The catheter denoted as (B8) may implement the CMUT array and the thermoelectric cooler in a catheter tip, and further include a catheter jacket coupled to the catheter tip and having length to reach from the prostate to exit of the urethra.

(B10) In the catheter denoted as (B9), the catheter jacket may include a thermally insulating layer for preventing heat conducted by the solid thermal conductor from damaging the wall of the urethra.

(B11) Either of the catheters denoted as (B9) and (B10) may further include a removable sleeve disposed about the catheter tip and the catheter jacket, wherein the removable sleeve includes an inflatable balloon for securing the removable sleeve to a bladder and having length to at least reach from the bladder to the exit of the urethra and being configured to remain in the urethra for a duration after extraction of the catheter tip from the urethra.

(B12) In the catheter denoted as (B11), the removable sleeve may further include a thermally insulating layer for preventing heat conducted by the solid thermal conductor from damaging the wall of the urethra.

(B13) Either of the catheters denoted as (B11) and (B12) may further include a rotation joint permitting rotation of the catheter tip relative to the inflatable balloon about a longitudinal axis of the catheter.

(B14) In the catheter denoted as (B13), the rotation joint may define a discrete plurality of orientations of the catheter tip about the longitudinal axis.

(B15) In any of the catheters denoted as (B11) through (B14), the removable sleeve may form a conduit for passing urine from the bladder to the exit of the urethra.

(B16) In any of the catheters denoted as (B11) through (B15), the removable sleeve may be rigid.

(B17) In any of the catheters denoted as (B11) through (B16), the removable sleeve may be pliable.

(C1) A system for enhanced ultrasound treatment with solid state cooling may include any one of the catheters denoted as (B1) through (B17), and two acoustic mirrors, each configured to cooperate with the CMUT array to form a respective acoustic cavity, to increase intensity of the ultrasound within the acoustic cavity.

(C2) The system denoted as (C1) may be configured for ultrasound treatment of a prostate, wherein the catheter is configured to position the CMUT array in a urethra at the prostate, and the two acoustic mirrors are respectively configured for (a) internal positioning in a rectum and (b) external positioning anterior to the prostate.

(D1) A medical device may include a catheter for exposing target tissue to ultrasound and a catheter handle mechanically coupled to a proximal end of the catheter and configured to be positioned outside a body channel into which the catheter is inserted, to at least partly control the catheter, wherein the catheter includes (a) a capacitive micromachined ultrasonic transducer (CMUT) array disposed at a distal end of the catheter and configured to emit the ultrasound to the target tissue, (b) a thermoelectric cooler configured to cool non-target tissue heated by the ultrasound, and (c) a solid thermal conductor coupled to the thermoelectric cooler and extending along the catheter away from the distal end toward a proximal end of the catheter, to conduct heat away from the thermoelectric cooler.

(D2) In the device denoted as (D1), the solid thermal conductor may extend to the catheter handle, and the catheter handle may include a heat exchanger for cooling the solid thermal conductor.

(D3) In either of the devices denoted as (D1) and (D2), the catheter handle may include electronic circuitry for driving the CMUT array and driving the thermoelectric cooler, and the catheter may include electrical connections coupling the electronic circuitry to the CMUT array and the thermoelectric cooler.

(D4) Any of the devices denoted as (D1) through (D3) may further include (i) one or more sensors positioned in the catheter and configured to sense a property of the non-target tissue, wherein the property is selected from the group consisting of temperature, pressure, and a combination thereof, and (ii) measurement circuitry positioned in the handle and electrically coupled to the one or more sensors, the measurement circuitry being configured to process sensor signals from the one or more sensors to determine the property.

(D5) Any of the devices denoted as (D1) through (D4) may further include a catheter sleeve for encasing the catheter, wherein the catheter sleeve and the catheter are removably coupled to enable leaving the catheter sleeve in the body channel after extraction of the catheter from the body channel, and the catheter sleeve may include at least one of (a) one or more tissue property sensors and (b) a conduit for passing fluid through the catheter sleeve.

(D6) In any of the devices denoted as (D1) through (D5), the catheter may be a urethral catheter configured for insertion into a urethra to position the CMUT array and the thermoelectric cooler at the prostate to apply the ultrasound treatment to the prostate.

(D7) In the device denoted as (D6), the catheter may include a catheter tip containing the CMUT array and the thermoelectric cooler, wherein the handle includes an actuator for changing a position of the catheter tip relative to a reference position associated with the prostate.

(D8) In the device denoted as (D7), the handle may further include an indicator for indicating the position of the catheter tip relative to the reference position.

(D9) In the device denoted as (D8), the catheter may include a rotation joint permitting rotation of the catheter tip about longitudinal axis of the catheter, wherein the actuator is capable of rotating the catheter tip about the longitudinal axis.

(D10) In either of the devices denoted as (D8) and (D9), the actuator may be capable of adjusting position of the catheter tip in direction along longitudinal axis of the catheter.

(E1) A system for enhanced ultrasound treatment may include (a) a catheter including an ultrasound transducer array and configured to position the ultrasound transducer array in a channel of a body to expose target tissue of the body to ultrasound, and (b) at least one acoustic mirror, each configured for positioning externally to the channel on a side of the target tissue that is opposite the ultrasound transducer array, to form an acoustic cavity that enhances intensity of the ultrasound at the target tissue by creating a standing acoustic wave between the ultrasound transducer array and the acoustic mirror.

(E2) In the system denoted as (E1), the catheter may be a urethral catheter configured to position the ultrasound transducer array at a prostate to treat the prostate with the ultrasound.

(E3) In the system denoted as (E2), the at least one acoustic mirror may include a first acoustic mirror configured for positioning externally to the body and anterior to the prostate, and a second acoustic mirror configured for positioning in rectum of the body.

(E4) In any of the systems denoted as (E1) through (E3), the ultrasound transducer array may be a capacitive micromachined ultrasonic transducer array.

(E5) In any of the systems denoted as (E1) through (E3), the ultrasound transducer array being a piezoelectric ultrasonic transducer array.

(F1) A system for enhanced ultrasound treatment may include a first ultrasound transducer array, and a second ultrasound transducer array cooperatively configured with the first ultrasound transducer array to form an acoustic cavity that enhances intensity of ultrasound, generated by the first ultrasound transducer array and the second ultrasound transducer array, at the target tissue by creating a standing acoustic wave within the acoustic cavity.

(F2) The system denoted as (F1) may further include a control module configured to adjust a phase shift between ultrasound emission of the first ultrasound transducer array and ultrasound emission of the second ultrasound transducer array, to adjust position of each antinode of the standing acoustic wave.

(F3) In the system denoted as (F2), the control module may be configured to sweep the phase shift so as to sweep the position of each antinode.

(F4) Any of the systems denoted as (F1) through (F3) may include a urethral catheter that contains the first ultrasound transducer array, wherein the urethral catheter is configured to position the first ultrasound transducer array in a urethra of a subject at a prostate, such that a portion of the prostate is contained by the acoustic cavity.

(F5) In the system denoted as (F4), the first ultrasound transducer array may be a capacitive micromachined ultrasonic transducer (CMUT) array, and the urethral catheter may further include at least one thermoelectric cooler mechanically coupled with the CMUT array and configured to cool a portion of a wall of the urethra heated by the ultrasound.

(F6) In the system denoted as (F5), the first ultrasound transducer device may be implemented at a distal end of the urethral catheter, and the urethral catheter may further include a solid thermal conductor coupled to the at least one thermoelectric cooler and extending along the urethral catheter away from the distal end toward a proximal end of the catheter, to conduct heat away from the thermoelectric cooler.

(F7) Any of the systems denoted as (F4) through (F6) may include a rectal catheter that contains the second ultrasound transducer array, wherein the rectal catheter is configured to position the second ultrasound transducer array in a rectum, such that the acoustic cavity contains a posterior portion of the prostate.

(F8) In any of the systems denoted as (F4) through (F6), the second ultrasound transducer may be configured for positioning outside body of the subject anterior to prostate, such that the acoustic cavity contains an anterior portion of the prostate.

(F9) In any of the systems denoted as (F1) through (F8), each of the first ultrasound transducer array and the second ultrasound transducer array may be a capacitive micromachined ultrasonic transducer array.

(F10) In any of the systems denoted as (F1) through (F8), each of the first ultrasound transducer array and the second ultrasound transducer array being a piezoelectric ultrasonic transducer array.

(G1) A catheter or catheter sleeve with solid state cooling may include a tubular wall for insertion into a channel of a body, and at least one thermoelectric cooler coupled to the tubular wall for cooling tissue of the channel.

(G2) In the catheter or catheter sleeve denoted as (G1), each thermoelectric cooler may be mounted to outside of the tubular wall and configured for operation with a cold side of the thermoelectric cooler facing away from the tubular wall and a hot side of the thermoelectric cooler facing the tubular wall.

(G3) The catheter or catheter sleeve denoted as (G2) may further include a solid thermal conductor positioned within space bounded by the tubular wall and thermally coupled to the hot side of each thermoelectric cooler to remove heat from the hot side.

(G4) In the catheter or catheter sleeve denoted as (G3), at least a portion of the tubular wall away from the at least one thermoelectric cooler may include a thermally insulating layer to prevent heat conducted by the solid thermal conductor from damaging tissue in thermal contact with the at least a portion of the tubular wall.

(G5) The catheter or catheter sleeve denoted as (G2) may further include (a) a solid thermal conductor disposed on outside of the tubular wall or integrated in the tubular wall, wherein the solid thermal conductor is thermally coupled to the hot side of each thermoelectric cooler to remove heat from the hot side of each thermoelectric cooler, and (b) a thermally insulating layer disposed on outside of the solid thermal conductor to prevent heat conducted by the solid thermal conductor from damaging tissue adjacent the solid thermal conductor.

(G6) In the catheter or catheter sleeve denoted as (G2), the tubular wall may have a proximal end configured to be external to the channel, each thermoelectric cooler may be at a section of the tubular wall a distance away from the proximal end, and the catheter may further include a solid thermal conductor thermally coupled to hot side of each thermoelectric cooler and extending to the proximal end of the tubular wall to conduct heat from the hot side of each thermoelectric cooler out of the channel.

(G7) In any of the catheters or catheter sleeves denoted as (G2) through (G6), each thermoelectric cooler may include (i) a plurality of n-type semiconductors and a plurality of p-type semiconductors electrically coupled in series such that the series alternates between the n-type semiconductors and the p-type semiconductors, (ii) a first thermal conductor thermally coupling the n-type semiconductors and the p-type semiconductors on the cold side, and (iii) a second thermal conductor mounted to the outside of the tubular wall and thermally coupling the n-type semiconductors and the p-type semiconductors on the hot side.

(G8) In the catheter or catheter sleeve denoted as (G7), a portion of the tubular wall supporting the thermoelectric cooler may be rigid, and the n-type semiconductors and the p-type semiconductors may be arranged in a rigid configuration conformed to curvature of the tubular wall.

(G9) In the catheter or catheter sleeve denoted as (G7), a portion of the tubular wall supporting the thermoelectric cooler may be pliable, and electrical connections between the n-type semiconductors and the p-type semiconductors may be flexible to conform to bending of the portion of the tubular wall.

(H1) A catheter sleeve with integrated sensing may include tubular casing for insertion into a channel of a body and capable of encasing a catheter, and at least one sensor coupled to the tubular casing and configured to sense one or more properties of tissue of the channel, wherein each of the one or more properties is selected from the group consisting of temperature and pressure.

(H2) The catheter sleeve denoted as (H1) may be configured to encase a urethral catheter.

(H3) The catheter sleeve denoted as (H2) may further include a conduit for passing urine from the bladder out of the urethra.

(H4) In the catheter sleeve denoted as (H3), the conduit may be formed in the tubular casing.

(H5) Any of the catheter sleeves denoted as (H1) through (H4) may further include an inflatable balloon for securing the catheter sleeve to a bladder, and a conduit for passing a fluid to the inflatable balloon to inflate the inflatable balloon.

(H6) In the catheter sleeve denoted as (H5), the conduit may be formed in the tubular casing.

(H7) In any of the catheter sleeves denoted as (H1) through (H6), the at least one sensor may include a plurality of sensors to sense the at least one property in a plurality of locations.

(H8) In any of the catheter sleeves denoted as (H1) through (H7), the tubular casing may include one or more electrical connections coupled to the at least one sensor and extending toward proximal end of the tubular casing to communicate, to electronic circuitry outside the channel, at least one sensor signal indicative of the one or more properties of the tissue.

(H9) In any of the catheter sleeves denoted as (H1) through (H8), the at least one sensor may include an active sensor, and the electrical connections may include a power connection to the active sensor from a power supply external to the channel.

(H10) In the catheter sleeve denoted as (H9), the tubular casing may include a pliable polymer casing, and the electrical connections may be formed in the pliable polymer casing.

(H11) In any of the catheter sleeves denoted as (H1) through (H8), each sensor may be a passive sensor.

(H12) In the catheter sleeve denoted as (H11), each sensor may be configured to wirelessly couple to a catheter placed in the sleeve, for readout of a respective sensor signal by the catheter.

(H13) In the catheter sleeve denoted as (H11), each sensor may include an electrical connection configured to electrically couple with an electrical connection of a catheter placed in the sleeve, for readout of a respective sensor signal by the catheter.

(I1) A system for ultrasound treatment with solid state cooling may include (1) ultrasound driving circuitry configured to generate drive signals to drive a capacitive micromachined ultrasonic transducer (CMUT) array, so as to expose target tissue to ultrasound, and (2) Peltier driving circuitry configured to drive at least one thermoelectric cooler, to cool non-target tissue heated by the ultrasound.

(I2) The system denoted as (I1) may further include ultrasound imaging circuitry configured to (a) generate a plurality of second signals to drive the CMUT array to image the target tissue and (b) produce an ultrasound image of the target tissue from electrical transducer signals received from the CMUT array.

(I3) The system denoted as (I2) may further include a control module configured to control generation of the drive signals by the ultrasound driving circuitry at least in part based upon the ultrasound image.

(I4) In the system denoted as (I3), the control module may be configured to control generation of the drive signals by the ultrasound driving circuitry at least in part based upon clutter signals and a predetermined correspondence between the clutter signals and efficacy of the ultrasound treatment.

(I5) In either of the systems denoted as (I3) through (I4), the ultrasound imaging circuitry may be configured to produce a Doppler image of the target tissue from the electrical transducer signals to evaluate degree of blood perfusion of the target tissue.

(I6) In any of the systems denoted as (I3) through (I5), the ultrasound imaging circuitry may be configured to produce a brightness image of the target tissue from the electrical transducer signals.

(I7) Any of the systems denoted as (I3) through (I6) may further include measurement circuitry configured to process signals from one or more sensors to determine a property of the non-target tissue, wherein the property being selected from the group consisting of temperature, pressure, and a combination thereof, and wherein the control module is configured to control generation of the drive signals by the ultrasound driving circuitry based upon the ultrasound image and the property.

(I8) Any of the systems denoted as (I1) through (I7) may further include temperature measurement circuitry configured to process signals from one or more temperature sensors to determine one or more respective temperatures of at least a portion of the non-target tissue.

(I9) Any of the systems denoted as (I1) through (I8) may further include pressure measurement circuitry configured to process signals from one or more pressure sensors to determine one or more respective pressures of the non-target tissue.

(I10) Any of the systems denoted as (I1) through (I9) may further include (i) measurement circuitry configured to process signals from one or more sensors to determine a property of the non-target tissue, the property being selected from the group consisting of temperature, pressure, and a combination thereof, and (ii) a control module configured to control generation of the drive signals by the ultrasound driving circuitry at least in part based upon the property.

(I11) Any of the systems denoted as (I1) through (I10) may further include (i) a catheter including the CMUT array and the at least one thermoelectric cooler, wherein the catheter is configured for insertion into a body channel, and (ii) a handle mechanically coupled with the catheter and containing the ultrasound driving circuitry and the Peltier driving circuitry, wherein the handle is configured for positioning outside the body channel.

(I12) In the system denoted as (I11), the catheter may include first electrical connections between the CMUT array and the ultrasound driving circuitry, and second electrical connections between the at least one thermoelectric cooler and the Peltier driving circuitry.

(I13) In the system denoted as (I12), the catheter may further include a solid thermal conductor thermally coupled to the at least one thermoelectric cooler and extending to the handle, for conducting heat from the at least one thermoelectric cooler out of the body channel.

(I14) In the system denoted as (I13), the handle may further include a heat exchanger for removing heat from the solid thermal conductor.

(I15) Any of the systems denoted as (I11) through (I14) may further include (I) one or more sensors positioned in the catheter and configured to sense a property of the non-target tissue, the property being selected from the group consisting of temperature, pressure, and a combination thereof, (II) measurement circuitry positioned in the handle and configured to process sensor signals from one or more sensors to determine the property from one or more sensor signals received from the one or more sensor, and (III) third electrical connections passing through the catheter and connecting the one or more sensors to the measurement circuitry to communicate the sensor signals.

(I16) In any of the systems denoted as (I11) through (I15), the catheter may be a urethral catheter configured for insertion into a urethra to position the CMUT array and the at least one thermoelectric cooler at the prostate to apply the ultrasound treatment to the prostate.

(J1) A method for ultrasound treatment with solid state cooling may include exposing target tissue to ultrasound generated by a capacitive micromachined ultrasonic transducer (CMUT) array, cooling non-target tissue using one or more thermoelectric coolers to prevent damage to the non-target tissue, and removing heat from the one or more thermoelectric coolers and away from the non-target tissue.

(J2) The method denoted as (J1) may include (a) in the step of exposing, generating the ultrasound from within a body channel, wherein the CMUT array has been advanced to the target tissue on a catheter through the body channel, (b) in the step of cooling, using the one or more thermoelectric coolers to cool wall of the body channel, wherein the one or more thermoelectric coolers are coupled to at least one of the CMUT array and the catheter, and (c) in the step of removing, removing the heat from the wall.

(J3) The method denoted as (J2) may include, in the step of exposing, exposing a prostate to the ultrasound from a urethra, and, in the step of cooling, cooling the wall of the urethra.

(J4) In either of the methods denoted as (J2) and (J3), the target tissue may be at least part of a prostrate, and the step of exposing may include inducing necrosis of the target tissue to treat benign prostatic hyperplasia.

(J5) In either of the methods denoted as (J2) and (J3), the target tissue may be a cancerous tumor of a prostrate, and the step of exposing may include inducing necrosis of the tissue of the cancerous tumor.

(J6) In any of the methods denoted as (J2) through (J5), the step of removing may include conducting the heat away from the one or more thermoelectric coolers through a solid thermal conductor coupled to the one or more thermoelectric coolers and extending through the catheter toward exit of the body channel.

(J7) In the method denoted as (J6), the step of removing may include conducting at least a portion of the heat through the solid thermal conductor to outside the exit.

(J8) The method denoted as (J7) may further include cooling the solid thermal conductor outside the exit.

(J9) In the method denoted as (J6), the step of removing may include redistributing the heat across at least a portion of the catheter.

(J10) Any of the methods denoted as (J1) through (J9) may further include monitoring temperature of the non-target tissue, and, in the step of exposing, adjusting exposure of the target tissue to the ultrasound according to the temperature.

(J11) In the method denoted as (J10), the step of adjusting may include at least temporarily ceasing said exposing when the temperature exceeds a threshold temperature.

(J12) Any of the methods denoted as (J1) through (J10) may further include monitoring pressure of the non-target tissue, and in the step of exposing, adjusting exposure of the target tissue to the ultrasound according to the pressure.

(J13) In the method denoted as (J12), the non-target tissue may be a wall of a body channel through which the CMUT array has been advanced to the target tissue.

(J14) Any of the methods denoted as (J1) through (J13) may further include imaging the target tissue using the CMUT array to obtain an ultrasound image indicating effect on the target tissue of the step of exposing, and, in the step of exposing, adjusting exposure of the target tissue to the ultrasound according to the effect.

(J15) The method denoted as (J14) may include alternatingly performing the steps of exposing and imaging.

(J16) Either of the methods denoted as (J14) and (J15) may further include, based upon the ultrasound image, comparing the effect as a function of position to a goal of the ultrasound treatment to identify a first portion of the target tissue in need of further ultrasound exposure, and, in the step of adjusting, redirecting ultrasound emission of the CMUT array to increase ultrasound exposure to the first portion.

(J17) In the method denoted as (J16), the step of redirecting may include applying beamforming to the CMUT array to focus at least a portion of the ultrasound on the first portion of the target tissue.

(J18) In either of the methods denoted as (J16) and (J17), the step of exposing may include generating the ultrasound from within a body channel, wherein the CMUT array has been advanced to the target tissue on a catheter through the body channel, and the step of redirecting may include rotating the CMUT array in the body channel to direct at least a portion of the ultrasound to the first portion of the target tissue.

(J19) Any of the methods denoted as (J14) through (J18) may include recording a spatially resolved clutter signal in the step of imaging, deducing instantaneous efficacy of the ultrasound treatment from the clutter signal, and, in the step of adjusting, adjusting the exposure according to the instantaneous efficacy.

(J20) In any of the methods denoted as (J1) through (J19), the step of exposing may include sequentially targeting different portions of the target tissue with the ultrasound.

(J21) In the method denoted as (J20), the step of sequentially targeting may include sequentially positioning the CMUT array in a plurality of positions along longitudinal axis of the catheter.

(J22) In either of the methods denoted as (J20) and (J21), the step of sequentially targeting may include rotating the CMUT array about longitudinal axis of the catheter.

(J23) In any of the methods denoted as (J20) through (J22), the step of sequentially targeting may include applying beamforming to the CMUT array to sequentially focus at least a portion of the ultrasound on the different portions.

(J24) Any of the methods denoted as (J1) through (J23) may further include heating a greater tissue region around and including the target tissue.

(J25) In any of the methods denoted as (J1) through (J23), the step of exposing may include exposing the target tissue to multifrequency ultrasound to focus the ultrasound on a localized region of the target tissue.

(J26) In the method denoted as (J25), the target tissue may be a cancerous prostate tumor.

(K1) A method for ultrasound treatment with ultrasound imaging feedback may include obtaining an image of target tissue from an ultrasound transducer array to determine a spatially resolved clutter signal for the target tissue, and, based upon the clutter signal and a predetermined correspondence between the clutter signal and treatment efficacy, determining one or more properties of subsequent generation of ultrasound by the ultrasound transducer array to treat the target tissue.

(K2) The method denoted as (K1) may include repeatedly performing the step of obtaining to update the spatially resolved clutter signal, and repeatedly revising the step of determining in accordance with the spatially resolved clutter signal as updated, to update the one or more properties.

(K3) Either of the methods denoted as (K1) and (K2) may further include commanding the ultrasound transducer array to generate the ultrasound having the one or more properties.

(K4) The method denoted as (K3) may include alternatingly performing the steps of obtaining and commanding.

(K5) In any of the methods denoted as (K1) through (K4), the step of determining may further include taking into account a measurement of temperature of non-target tissue heated by the ultrasound, to determine the one or more properties.

(K6) In the method denoted as (K5), the target tissue may be prostate tissue, the non-target tissue being a portion of a urethral wall.

(K7) Either of the methods denoted as (K5) and (K6) may include at least temporarily ceasing the generation of ultrasound when the temperature as measured exceeds a threshold temperature.

(K8) In any of the methods denoted as (K1) through (K4), the step of determining may further include taking into account measurement of one or both of temperature and pressure of non-target tissue heated by the ultrasound, to determine the one or more properties.

(K9) In the method denoted as (K8), the target tissue may be prostate tissue, and the non-target tissue may be a portion of a urethral wall.

(K10) In any of the methods denoted as (K1) through (K9), the step of determining may include determining intensity of the ultrasound to be subsequently generated by the ultrasound transducer array as a function of position within the target tissue.

(K11) The method denoted as (K10) may include commanding the ultrasound transducer array to beamform the ultrasound according to the intensity as a function of position as determined in the step of determining.

(K12) In the method denoted as (K11), the step of commanding may include commanding the ultrasound transducer array to focus the ultrasound on one or more localized regions of the target tissue.

(K13) Any of the methods denoted as (K1) through (K12) may include in the step of obtaining, obtaining an image of a prostate, and, in the step of determining, utilizing a prostate-tissue specific, predetermined correspondence between the clutter signal and treatment efficacy to determine the one or more properties applicable to prostate tissue, to enable ultrasound treatment of a prostate.

(K14) In any of the methods denoted as (K1) through (K13), the step of determining may include selecting the predetermined correspondence from a selection of blood-perfusion specific correspondences.

(K15) The method denoted as (K14) may further include evaluating degree of blood perfusion of the target tissue from a Doppler image of the target tissue generated by the ultrasound transducer array, and, in the step of determining, selecting the predetermined correspondence from the selection of blood-perfusion specific correspondences according to the degree of blood perfusion.

(L1) A product for controlling ultrasound treatment using ultrasound imaging feedback may include machine-readable instructions encoded in non-transitory memory, wherein the machine-readable instructions include (a) a correspondence between an ultrasound clutter signal and efficacy of the ultrasound treatment, and (b) treatment control instructions that, when executed by a processor, evaluate spatially resolved clutter signals obtained from ultrasound imaging of target tissue and utilize the correspondence to determine one or more properties of subsequent ultrasound exposure of the target tissue.

(L2) In the product denoted as (L1), the treatment control instructions may be configured to repeatedly determine the one or more properties, to adjust the ultrasound exposure according to updated spatially resolved clutter signals from repetitions of the ultrasound imaging.

(L3) In either of the products denoted as (L1) and (L2), the treatment control instructions may be configured to, when determining the one or more properties, further take into account a measurement of temperature of non-target tissue heated by the ultrasound exposure.

(L4) In the product denoted as (L3), the machine-readable instructions may further include a threshold temperature, and the treatment control instructions may be configured to at least temporarily cease the ultrasound exposure when the temperature, as measured, exceeds the threshold temperature.

(L5) In any of the products denoted as (L1) through (L4), at least one of the properties may be spatially resolved such that the ultrasound exposure is position sensitive.

(L6) In the product denoted as (L5), the treatment control instructions may include beamforming instructions that, when executed by the processor, generate a plurality of drive signals configured to drive an ultrasound transducer array to focus the ultrasound exposure on one or more localized regions of the target tissue, based upon the spatially resolved clutter signals and the correspondence.

(L7) In any of the products denoted as (L1) through (L6), the correspondence may be applicable to prostate tissue to enable ultrasound treatment of a prostate.

(L8) In any of the products denoted as (L1) through (L7), the correspondence may be sensitive to degree of blood perfusion in the target tissue.

(L9) In the product denoted as (L8), the machine-readable instructions may further include correspondence selection instructions that, when executed by the processor, select the correspondence from a plurality of blood-perfusion specific correspondences between the ultrasound clutter signal and the efficacy.

(L10) In the product denoted as (L9), the machine-readable instructions may further include perfusion evaluation instructions that, when executed by a processor, determine the degree of blood perfusion from an ultrasound Doppler image of the prostate tissue.

(L11) In any of the products denoted as (L1) through (L10), the efficacy may be characterized by one or more properties selected from the group consisting of elasticity and echogenicity of the target tissue.

(L12) In any of the products denoted as (L1) through (L10), the efficacy may be characterized by one or more properties selected from the group consisting of elasticity, necrosis, and temperature of the target tissue.

(M1) A method for manufacturing a capacitive micromachined ultrasonic transducer (CMUT) array with solid state cooling may include fabricating the CMUT array on a first thermal conductor of a thermoelectric cooler, wherein the thermoelectric cooler includes the first thermal conductor, a second thermal conductor, and, disposed between the first thermal conductor and the second thermal conductor, a plurality of n-type semiconductors and a plurality of p-type semiconductors electrically coupled in series such that the series alternates between the n-type semiconductors and the p-type semiconductors.

(M2) In the method denoted as (M1), each of the first thermal conductor and the second thermal conductor may be an electric insulator.

(M3) In either of the methods denoted as (M1) and (M2), the step of fabricating may include (a) depositing a plurality of first electrodes of the CMUT array on the first thermal conductor, (b) forming an electrically insulating layer on the first thermal conductor and covering the first electrodes, wherein the electrically insulating layer has a plurality of vacuum cavities therein, and wherein each of the vacuum cavities corresponds to a respective transducer of the CMUT array and is positioned above a respective one of the first electrodes, and (c) depositing a plurality of second electrodes of the CMUT array on the electrically insulating layer, each of the second electrodes being positioned above a respective one of the vacuum cavities.

(M4) The method denoted as (M3) may further include depositing a protective layer over the second electrodes.

Changes may be made in the above devices, systems, and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present devices, systems, and methods, which, as a matter of language, might be said to fall therebetween.

What is claimed is:

1. A catheter for ultrasound treatment with solid state cooling, comprising:
   a distal end configured to be disposed within a body channel during operation of the catheter;
   a proximal end configured to remain outside the body channel during said operation;
   a capacitive micromachined ultrasonic transducer (CMUT) array disposed at a distal end of the catheter and configured to emit ultrasound to target tissue;
   a thermoelectric cooler disposed at the distal end and having opposed first and second sides, wherein during operation of the catheter the first side of the thermoelectric cooler is in thermal contact with non-target tissue to cool the non-target tissue and
   a solid thermal conductor coupled to the second side of the thermoelectric cooler and extending along the catheter away from the distal end and toward the proximal end, to conduct heat away from the second side of the thermoelectric cooler during operation of the catheter.

2. The catheter of claim 1, the thermoelectric cooler being mechanically coupled with the CMUT array.

3. The catheter of claim 1, further comprising a temperature sensor for sensing temperature of the non-target tissue, the temperature sensor being disposed at the distal end.

4. The catheter of claim 1, further comprising a pressure sensor for sensing pressure of the non-target tissue, the pressure sensor being disposed at the distal end.

5. The catheter of claim 1, the catheter being configured for insertion into a urethra, the target tissue being a prostate, the non-target tissue being atleast a portion of wall of the urethra.

6. The catheter of claim 5, implementing the CMUT array and the thermoelectric cooler in a catheter tip, and further comprising a catheter jacket coupled to the catheter tip and having length to reach from the prostate to exit of the urethra.

7. The catheter of claim 6, the catheter jacket including a thermally insulating layer for preventing heat conducted by the solid thermal conductor from damaging the wall of the urethra.

8. The catheter of claim 6, further comprising a removable sleeve disposed about the catheter tip and the catheter jacket, the removable sleeve including an inflatable balloon for securing the removable sleeve to a bladder and having length to at least reach from the bladder to the exit of the urethra and being configured to remain in the urethra for a duration after extraction of the catheter tip from the urethra.

9. The catheter of claim 8, the removable sleeve further including a thermally insulating layer for preventing heat conducted by the solid thermal conductor from damaging the wall of the urethra.

10. A method for ultrasound treatment with solid state cooling, comprising:
    exposing target tissue to ultrasound generated by a capacitive micromachined ultrasonic transducer (CMUT) array, said exposing comprising generating the ultrasound from within a body channel, the CMUT array having been advanced to the target tissue on a catheter through the body channel;
    to prevent damage to a wall of the body channel, cooling the wall with one or more thermoelectric coolers disposed within the body channel coupled to at least one of the CMUT array and the catheter, a thermoelectric cooler of the one or more thermoelectric coolers having opposed first and second sides, wherein during operation of the catheter the first side of the thermoelectric cooler is in thermal contact with non-target tissue to cool the non-target tissue; and
    removing heat from the one or more thermoelectric coolers and away from the wall, said removing the heat comprising conducting the heat away from the second side of the thermoelectric cooler of the one or more thermoelectric coolers during operation of the catheter through a solid thermal conductor coupled to the second side of the thermoelectric cooler of the one or more thermoelectric coolers and extending through the catheter toward exit of the body channel.

11. The method of claim 10, comprising:
    in the step of exposing, exposing a prostate to the ultrasound from a urethra;
    and in the step of cooling, cooling wall of the urethra.

12. The method of claim 10, the step of removing comprising conducting at least a portion of the heat through the solid thermal conductor to outside the exit.

13. The method of claim 10, the step of removing comprising redistributing the heat across at least a portion of the catheter.

14. The method of claim 10, further comprising:
    monitoring temperature of the wall; and
    in the step of exposing, adjusting exposure of the target tissue to the ultrasound according to the temperature.

15. The method of claim 14, the step of adjusting comprising at least temporarily ceasing said exposing when the temperature exceeds a threshold temperature.

16. The method of claim 10, further comprising:
    monitoring pressure of the wall; and
    in the step of exposing, adjusting exposure of the target tissue to the ultrasound according to the pressure.

* * * * *

UNITED STATES PATENT AND TRADEMARK OFFICE
CERTIFICATE OF CORRECTION

PATENT NO. : 11,154,730 B2
APPLICATION NO. : 16/130896
DATED : October 26, 2021
INVENTOR(S) : Arif Sanli Ergün et al.

Page 1 of 1

It is certified that error appears in the above-identified patent and that said Letters Patent is hereby corrected as shown below:

In the Claims

Column 66, Line 54 delete "tissue and" and insert --tissue; and--
Column 67, Line 3 delete "atleast" and insert --at least--

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*